(12) United States Patent
Chen-Kiang et al.

(10) Patent No.: US 10,314,842 B2
(45) Date of Patent: Jun. 11, 2019

(54) METHODS FOR TREATING B CELL PROLIFERATIVE DISORDERS

(71) Applicant: Cornell University, Ithaca, NY (US)

(72) Inventors: Selina Chen-Kiang, New York, NY (US); Maurizio Di Liberto, Rivervale, NJ (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/101,240

(22) PCT Filed: Dec. 2, 2014

(86) PCT No.: PCT/US2014/068237
§ 371 (c)(1),
(2) Date: Jun. 2, 2016

(87) PCT Pub. No.: WO2015/084892
PCT Pub. Date: Jun. 11, 2015

(65) Prior Publication Data
US 2016/0303130 A1    Oct. 20, 2016

Related U.S. Application Data

(60) Provisional application No. 61/910,876, filed on Dec. 2, 2013.

(51) Int. Cl.
*A61K 31/519* (2006.01)
*A61K 31/35* (2006.01)
*A61K 31/351* (2006.01)
*A61K 45/06* (2006.01)

(52) U.S. Cl.
CPC ......... *A61K 31/519* (2013.01); *A61K 31/35* (2013.01); *A61K 31/351* (2013.01); *A61K 45/06* (2013.01)

(58) Field of Classification Search
CPC .................................................. A61K 31/444
USPC .................................................. 514/252.16
See application file for complete search history.

(56) References Cited

FOREIGN PATENT DOCUMENTS

| WO | WO-2013/059738 A2 | 4/2013 |
| WO | WO-2015/084892 A1 | 6/2015 |

OTHER PUBLICATIONS

Deng et al., Clinical Cancer Research;2012;18(13):3499-508.*
"International Application Serial No. PCT/US2014/068237, International Preliminary Report on Patentability dated Jun. 16, 2016", 8 pgs.
"International Application Serial No. PCT/US2014/068237, International Search Report dated Feb. 27, 2015", 4 pgs.
"International Application Serial No. PCT/US2014/068237, Written Opinion dated Feb. 27, 2015", 6 pgs.
Burger, Jan A., et al., "The Btk Inhibitor Ibrutinib (PCI-32765) in Combination with Rituximab is Well Tolerated and Displays Profound Activity in High-Risk Chronic Lymphocytic Leukemia (CLL) Patients", Abstract No. 187, *ASH Annual Meeting Abstracts, Blood*, 210, (2012), 4 pgs.

(Continued)

*Primary Examiner* — San Ming R Hui
(74) *Attorney, Agent, or Firm* — Schwegman Lundberg & Woessner, P.A.

(57) ABSTRACT

Described herein are methods for treating B cell proliferative disorders, in an individual in need thereof. The methods include administering to an individual in need thereof a Btk inhibitor (e.g., ibrutinib), in combination with a CDK4 inhibitor (e.g., palbociclib).

20 Claims, 20 Drawing Sheets

(56) References Cited

OTHER PUBLICATIONS

Leonard, John P., et al., "Selective CDK4/6 inhibition with tumor responses by PD0332991 in patients with mantle cell lymphoma", *Blood*, 119(20), (2012), 4597-4607.

Murawski, Niels, et al., "New drugs for aggressive B-cell and T-cell lymphomas", *The Lancet Oncology*, 11(11) (Nov. 2010), 1074-1085.

Shah, Bijal D., et al., "Mantle Cell Lymphoma: A Clinically Heterogeneous Disease in Need of Tailored Approaches", *Cancer Control*, 19(3), (Jul. 2012), 227-235.

\* cited by examiner

SEQ ID NO. 1

Met Ala Ala Val Ile Leu Glu Ser Ile Phe Leu Lys Arg Ser Gln Gln Lys Lys Lys Thr Ser Pro Leu Asn Phe Lys
Lys Arg Leu Phe Leu Leu Thr Val His Lys Leu Ser Tyr Tyr Glu Tyr Asp Phe Glu Arg Gly Arg Arg Gly Ser
Lys Lys Gly Ser Ile Asp Val Glu Lys Ile Thr Cys Val Glu Thr Val Val Pro Glu Lys Asn Pro Pro Pro Glu Arg
Gln Ile Pro Arg Arg Gly Glu Glu Ser Ser Glu Met Glu Gln Ile Ser Ile Ile Glu Arg Phe Pro Tyr Pro Phe Gln
Val Val Tyr Asp Glu Gly Pro Leu Tyr Val Phe Ser Pro Thr Glu Glu Leu Arg Lys Arg Trp Ile His Gln Leu Lys
Asn Val Ile Arg Tyr Asn Ser Asp Leu Val Gln Lys Tyr His Pro Cys Phe Trp Ile Asp Gly Gln Tyr Leu Cys
Cys Ser Gln Thr Ala Lys Asn Ala Met Gly Cys Gln Ile Leu Glu Asn Arg Asn Gly Ser Leu Lys Pro Gly Ser
Ser His Arg Lys Thr Lys Lys Pro Leu Pro Pro Thr Pro Glu Glu Asp Gln Ile Leu Lys Lys Pro Leu Pro Pro Glu
Pro Ala Ala Ala Pro Val Ser Thr Ser Glu Leu Lys Lys Val Val Ala Leu Tyr Asp Tyr Met Pro Met Asn Ala
Asn Asp Leu Gln Leu Arg Lys Gly Asp Glu Tyr Phe Ile Leu Glu Glu Ser Asn Leu Pro Trp Trp Arg Ala Arg
Asp Lys Asn Gly Gln Glu Gly Tyr Ile Pro Ser Asn Tyr Val Thr Glu Ala Glu Asp Ser Ile Glu Met Tyr Glu Trp
Tyr Ser Lys His Met Thr Arg Ser Gln Ala Glu Gln Leu Leu Lys Gln Glu Gly Lys Glu Gly Gly Phe Ile Val
Arg Asp Ser Ser Lys Ala Gly Lys Tyr Thr Val Ser Val Phe Ala Lys Ser Thr Gly Asp Pro Gln Gly Val Ile Arg
His Tyr Val Val Cys Ser Thr Pro Gln Ser Gln Tyr Tyr Leu Ala Glu Lys His Leu Phe Ser Thr Ile Pro Glu Leu
Ile Asn Tyr His Gln His Asn Ser Ala Gly Leu Ile Ser Arg Leu Lys Tyr Pro Val Ser Gln Gln Asn Lys Asn Ala
Pro Ser Thr Ala Gly Leu Gly Tyr Gly Ser Trp Glu Ile Asp Pro Lys Asp Leu Thr Phe Leu Lys Glu Leu Gly
Thr Gly Gln Phe Gly Val Val Lys Tyr Gly Lys Trp Arg Gly Gln Tyr Asp Val Ala Ile Lys Met Ile
Lys Glu Gly Ser Met Ser Glu Asp Glu Phe Ile Glu Glu Ala Lys Val
Met Met Asn Leu Ser His Glu Lys Leu Val Gln Leu Tyr Gly Val Cys
Thr Lys Gln Arg Pro Ile Phe Ile Ile Thr Glu Tyr Met Ala Asn Gly
Cys Leu Leu Asn Tyr Leu Arg Glu Met Arg His Arg Phe Gln Thr Gln
Gln Leu Leu Glu Met Cys Lys Asp Val Cys Glu Ala Met Glu Tyr Leu
Glu Ser Lys Gln Phe Leu His Arg Asp Leu Ala Ala Arg Asn Cys Leu
Val Asn Asp Gln Gly Val Val Lys Val Ser Asp Phe Gly Leu Ser Arg
Tyr Val Leu Asp Asp Glu Tyr Thr Ser Ser Val Gly Ser Lys Phe Pro
Val Arg Trp Ser Pro Pro Glu Val Leu Met Tyr Ser Lys Phe Ser Ser
Lys Ser Asp Ile Trp Ala Phe Gly Val Leu Met Trp Glu Ile Tyr Ser
Leu Gly Lys Met Pro Tyr Glu Arg Phe Thr Asn Ser Glu Thr Ala Glu
His Ile Ala Gln Gly Leu Arg Leu Tyr Arg Pro His Leu Ala Ser Glu
Lys Val Tyr Thr Ile Met Tyr Ser Cys Trp His Glu Lys Ala Asp Glu
Arg Pro Thr Phe Lys Ile Leu Leu Ser Asn Ile Leu Asp Val Met Asp
Glu Glu Ser

FIG. 10

METHODS FOR TREATING B CELL PROLIFERATIVE DISORDERS

CROSS-REFERENCE

This application is a U.S. National Stage Application filing under 35 U.S.C. 371 from International Application No. PCT/US2014/06823 lied on Dec. 2, 2014, and published as WO 2015/084892 A1 on Jun. 11, 2015, which claims the benefit of U.S. Provisional Application Ser. No. 61/910,876, filed Dec. 2, 2013, which applications and publication are incorporated herein by reference in their entireties.

SUMMARY OF THE INVENTION

Disclosed herein, in certain embodiments, are methods of treating a mantle cell lymphoma in an individual in need thereof, that comprises administering to the individual (a) a therapeutically-effective amount of Ibrutinib, and (b) a therapeutically-effective amount of a CDK4 inhibitor. In some embodiments, the mantle cell lymphoma is characterized by a plurality of cells having a C481S mutation in a BTK polypeptide. In some embodiments, the mantle cell lymphoma is characterized by a plurality of cells having elevation of CDK4. In some embodiments, the mantle cell lymphoma is characterized by a plurality of cell having a t(11; 14)(q13; q32) chromosomal translocation. In some embodiments, the mantle cell lymphoma is refractory to Ibrutinib. In some embodiments, the mantle cell lymphoma is relapsed following treatment with Ibrutinib. In some embodiments, Ibrutinib is administered at a daily dosage of about 560 mg per day. In some embodiments, the CDK4 inhibitor is selective for CDK4. In some embodiments, the CDK4 inhibitor is selective for CDK4 and CDK6. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib. In some embodiments, Ibrutinib and the CDK4 inhibitor are in a unified dosage form. In some embodiments, Ibrutinib and the CDK4 inhibitor are administered separately. In some embodiments, Ibrutinib and the CDK4 inhibitor are administered concurrently, simultaneously or substantially simultaneously. In some embodiments, the method further comprises administering an additional therapeutic agent.

Disclosed herein, in certain embodiments, are methods method of treating a mantle cell lymphoma in an individual in need thereof, that comprises administering to the individual (a) a therapeutically-effective amount of Ibrutinib, and (b) a therapeutically-effective amount of palbociclib. In some embodiments, the mantle cell lymphoma is characterized by a plurality of cells having a C481S mutation in a BTK polypeptide. In some embodiments, the mantle cell lymphoma is characterized by a plurality of cells having elevation of CDK4. In some embodiments, the mantle cell lymphoma is characterized by a plurality of cell having a t(11; 14)(q13; q32) chromosomal translocation. In some embodiments, the mantle cell lymphoma is refractory to Ibrutinib. In some embodiments, the mantle cell lymphoma is relapsed following treatment with Ibrutinib. In some embodiments, Ibrutinib is administered at a daily dosage of about 560 mg per day. In some embodiments, Ibrutinib and palbociclib are in a unified dosage form. In some embodiments, Ibrutinib and palbociclib are administered separately. In some embodiments, Ibrutinib and palbociclib are administered concurrently, simultaneously or substantially simultaneously. In some embodiments, the methods further comprise administering an additional therapeutic agent.

Disclosed herein, in certain embodiments, are methods method of treating a B cell proliferative disorder in an individual in need thereof, that comprises administering to the individual (a) a therapeutically-effective amount of Ibrutinib, and (b) a therapeutically-effective amount of a CDK4 inhibitor. In some embodiments, the B cell proliferative disorder is characterized by a plurality of cells having a C481S mutation in a BTK polypeptide. In some embodiments, the B cell proliferative disorder is characterized by a plurality of cells having elevation of CDK4. In some embodiments, the B cell proliferative disorder is characterized by a plurality of cell having a t(11; 14)(q13; q32) chromosomal translocation. In some embodiments, the B cell proliferative disorder is refractory to Ibrutinib. In some embodiments, the B cell proliferative disorder is relapsed following treatment with Ibrutinib. In some embodiments, the B cell proliferative disorder is a lymphoma. In some embodiments, the B cell proliferative disorder is a non-Hodgkins lymphoma. In some embodiments, the B cell proliferative disorder is mantle cell lymphoma. In some embodiments, the B cell proliferative disorder is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit (DH) DLBCL, primary mediastinal B-cell lymphoma (PMBL), Burkitt's lymphoma, follicular lymphoma, immunoblastic large cell lymphoma, precursor B-lymphoblastic lymphoma, precursor B-cell acute lymphoblastic leukemia, hairy cell leukemia B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, Ibrutinib is administered at a daily dosage of about 560 mg per day. In some embodiments, the CDK4 inhibitor is selective for CDK4. In some embodiments, the CDK4 inhibitor is selective for CDK4 and CDK6. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib. In some embodiments, Ibrutinib and the CDK4 inhibitor are in a unified dosage form. In some embodiments, Ibrutinib and the CDK4 inhibitor are administered separately. In some embodiments, Ibrutinib and the CDK4 inhibitor are administered concurrently, simultaneously or substantially simultaneously. In some embodiments, the methods further comprise administering an additional therapeutic agent.

Disclosed herein, in certain embodiments, are methods method of treating a B cell proliferative disorder in an individual in need thereof, that comprises administering to the individual (a) a therapeutically-effective amount of Ibrutinib, and (b) a therapeutically-effective amount of palbociclib. In some embodiments, the B cell proliferative disorder is characterized by a plurality of cells having a C481S mutation in a BTK polypeptide. In some embodiments, the B cell proliferative disorder is characterized by a plurality of cells having elevation of CDK4. In some embodiments, the B cell proliferative disorder is characterized by a plurality of cell having a t(11; 14)(q13; q32) chromosomal translocation. In some embodiments, the B cell proliferative disorder is refractory to Ibrutinib. In some embodiments, the B cell proliferative disorder is relapsed following treatment with Ibrutinib. In some embodiments, the B cell proliferative disorder is a lymphoma. In some embodiments, the B cell proliferative disorder is a non-Hodgkins lymphoma. In some embodiments, the B cell proliferative disorder is mantle cell lymphoma. In some embodiments, the B cell proliferative disorder is chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit (DH) DLBCL, primary mediastinal B-cell lymphoma (PMBL), Burkitt's lymphoma, follicular lymphoma, immunoblastic large cell lymphoma, precursor B-lymphoblastic lymphoma, precursor B-cell acute lymphoblastic leukemia, hairy cell leukemiaB cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, Ibrutinib is administered at a daily dosage of about 560 mg per day. In some embodiments, Ibrutinib and palbociclib are in a unified dosage form. In some embodiments, Ibrutinib and palbociclib are administered separately. In some embodiments, Ibrutinib and palbociclib are administered concurrently, simultaneously or substantially simultaneously. In some embodiments, the methods further comprise administering an additional therapeutic agent.

Disclosed herein, in certain embodiments, are pharmaceutical compositions that comprise (a) a therapeutically-effective amount of Ibrutinib, (b) a therapeutically-effective amount of a CDK4 inhibitor, and (c) a pharmaceutically-acceptable excipient. In some embodiments, the CDK4 inhibitor is a selective CDK4 inhibitor. In some embodiments, the CDK4 inhibitor is a selective CDK4/CDK6 inhibitor. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib.

Disclosed herein, in certain embodiments, are compositions that comprise (a) a therapeutically-effective amount of Ibrutinib, and (b) a therapeutically-effective amount of a CDK4 inhibitor. In some embodiments, the compositions further comprise a pharmaceutically-acceptable excipient. In some embodiments, the CDK4 inhibitor is a selective CDK4 inhibitor. In some embodiments, the CDK4 inhibitor is a selective CDK4/CDK6 inhibitor. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib. In some embodiments, Ibrutinib and the CDK4 inhibitor are in a unified dosage form. In some embodiments, Ibrutinib and the CDK4 inhibitor are in separate dosage forms.

Disclosed herein, in certain embodiments, is a pharmaceutical combination comprising: (a) a therapeutically-effective amount of Ibrutinib; (b) a therapeutically-effective amount of a CDK4 inhibitor; and (c) a pharmaceutically-acceptable excipient. In some embodiments, the CDK4 inhibitor is a selective CDK4 inhibitor or a selective CDK4/CDK6 inhibitor. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib.

Disclosed herein, in certain embodiments, is a composition comprising: (a) a therapeutically-effective amount of Ibrutinib; and (b) a therapeutically-effective amount of a CDK4 inhibitor. In some embodiments, the composition further comprises a pharmaceutically-acceptable excipient. In some embodiments, the CDK4 inhibitor is a selective CDK4 inhibitor or a selective CDK4/CDK6 inhibitor. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib. In some embodiments, Ibrutinib and the CDK4 inhibitor are in a unified dosage form or in separate dosage forms.

Disclosed herein, in certain embodiments, is a use of a combination of (a) a therapeutically-effective amount of Ibrutinib, and (b) a therapeutically-effective amount of a CDK4 inhibitor for treating a B cell proliferative disorder in an individual in need thereof. In some embodiments, the B cell proliferative disorder is characterized by a plurality of cells having a C481S mutation in a BTK polypeptide. In some embodiments, the B cell proliferative disorder is characterized by a plurality of cells having an elevated level of CDK4 expression. In some embodiments, the elevated level of CDK4 expression is an increased level of CDK4 expression. In some embodiments, the increased level of CDK4 expression is an increased protein expression. In some embodiments, the increased level of CDK4 expression in an increased gene expression. In some embodiments, the B cell proliferative disorder is characterized by a plurality of cell having a t(11; 14)(q13; q32) chromosomal translocation. In some embodiments, the B cell proliferative disorder is refractory to Ibrutinib or relapsed following treatment with Ibrutinib. In some embodiments, the B cell proliferative disorder is a lymphoma. In some embodiments, the B cell proliferative disorder is a non-Hodgkins lymphoma. In some embodiments, the B cell proliferative disorder is mantle cell lymphoma, chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit (DH) DLBCL, primary mediastinal B-cell lymphoma (PMBL), Burkitt's lymphoma, follicular lymphoma, immunoblastic large cell lymphoma, precursor B-lymphoblastic lymphoma, precursor B-cell acute lymphoblastic leukemia, hairy cell leukemiaB cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the B cell proliferative disorder is an ibrutinib-resistant B cell proliferative disorder. In some embodiments, the CDK4 inhibitor is selective for CDK4 or selective for CDK4 and CDK6. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib. In some embodiments, Ibrutinib and the CDK4 inhibitor are administered concurrently, simultaneously or separately. In some embodiments, the combination of (a) a therapeutically-effective amount of Ibrutinib, and (b) a therapeutically-effective amount of a CDK4 inhibitor further comprises administering an additional therapeutic agent.

Disclosed herein, in certain embodiments, is a use of a combination of (a) a therapeutically-effective amount of Ibrutinib, and (b) a therapeutically-effective amount of palbociclib for treating a B cell proliferative disorder in an individual in need thereof. In some embodiments, the B cell proliferative disorder is characterized by a plurality of cells having a C481S mutation in a BTK polypeptide. In some embodiments, the B cell proliferative disorder is characterized by a plurality of cells having an elevated level of CDK4 expression. In some embodiments, the elevated level of CDK4 expression is an increased level of CDK4 expression. In some embodiments, the increased level of CDK4 expression is an increased protein expression. In some embodiments, the increased level of CDK4 expression in an increased gene expression. In some embodiments, the B cell proliferative disorder is characterized by a plurality of cell having a t(11; 14)(q13; q32) chromosomal translocation. In some embodiments, the B cell proliferative disorder is refractory to Ibrutinib or relapsed following treatment with Ibrutinib. In some embodiments, the B cell proliferative disorder is a lymphoma. In some embodiments, the B cell proliferative disorder is a non-Hodgkins lymphoma. In some embodiments, the B cell proliferative disorder is mantle cell lymphoma, chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit (DH) DLBCL, primary mediastinal B-cell lymphoma (PMBL), Burkitt's lymphoma, follicular lymphoma, immunoblastic large cell lymphoma, precursor B-lymphoblastic lymphoma, precursor B-cell acute lymphoblastic leukemia, hairy cell leukemiaB cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis. In some embodiments, the B cell proliferative disorder is an ibrutinib-resistant B cell proliferative disorder. In some embodiments, Ibrutinib and palbociclib are administered concurrently, simultaneously or separately. In some embodiments, the combination further comprises administering an additional therapeutic agent.

Disclosed herein, in certain embodiments, is a use of a combination of (a) a therapeutically-effective amount of Ibrutinib, and (b) a therapeutically-effective amount of a CDK4 inhibitor for treating a mantle cell lymphoma in an individual in need thereof. In some embodiments, mantle cell lymphoma is characterized by a plurality of cells having an elevated level of CDK4 expression. In some embodiments, the elevated level of CDK4 expression is an increased level of CDK4 expression. In some embodiments, the increased level of CDK4 expression is an increased protein expression. In some embodiments, the increased level of CDK4 expression in an increased gene expression. In some embodiments, mantle cell lymphoma is characterized by a plurality of cell having a t(11; 14)(q13; q32) chromosomal translocation. In some embodiments, mantle cell lymphoma is refractory to Ibrutinib or relapsed following treatment with Ibrutinib. In some embodiments, mantle cell lymphoma is an ibrutinib-resistant mantle cell lymphoma. In some embodiments, the CDK4 inhibitor is selective for CDK4 or selective for CDK4 and CDK6. In some embodiments, the CDK4 inhibitor is selected from the group consisting of: Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is palbociclib. In some embodiments, Ibrutinib and the CDK4 inhibitor are administered concurrently, simultaneously or separately. In some embodiments, the combination further comprises administering an additional therapeutic agent.

Disclosed herein, in certain embodiments, is a use of a combination of (a) a therapeutically-effective amount of Ibrutinib, and (b) a therapeutically-effective amount of palbociclib for treating a mantle cell lymphoma in an individual in need thereof. In some embodiments, mantle cell lymphoma is characterized by a plurality of cells having an elevated level of CDK4 expression. In some embodiments, the elevated level of CDK4 expression is an increased level of CDK4 expression. In some embodiments, the increased level of CDK4 expression is an increased protein expression. In some embodiments, the increased level of CDK4 expression is an increased gene expression. In some embodiments, mantle cell lymphoma is characterized by a plurality of cell having a t(11; 14)(q13; q32) chromosomal translocation. In some embodiments, mantle cell lymphoma is refractory to Ibrutinib or relapsed following treatment with Ibrutinib. In some embodiments, mantle cell lymphoma is an ibrutinib-resistant mantle cell lymphoma. In some embodiments, Ibrutinib and palbociclib are administered concurrently, simultaneously or separately. In some embodiments, the combination further comprises administering an additional therapeutic agent.

BRIEF DESCRIPTION OF THE FIGURES

FIG. 1A exemplifies a WES analysis of single nucleotide variations (SNVs; % of alternative allele) in the DNA of cheek swab (CS) and in MCL cells from serial biopsies of Pt7, and schema of the C481S mutation in BTK. FIG. 1B exemplifies an integrative genomics viewer (IGV) visualization of nucleotide substitution and alignments of BTK on the chromosome X (ChrX):100611160-100611169. FIG. 1C exemplifies a WTS analysis of mRNA abundance (bars) and non-synonymous SNVs (% of alternative allele) in the coding regions of BTK, PLCG2 and AKT1. FIG. 1D exemplifies immunoblotting of indicated proteins in PBC and serial biopsies of Pt7. FIG. 1E exemplifies a WTS analysis of mRNA abundance of indicated genes in PBCs and serial biopsies of Pt7.

FIG. 2A exemplifies a representative image of immunohistochemical analysis of Ki67, pSRb and Rb in MCL cells (PAX5+) cells (left) and quantification (right). FIG. 2B exemplifies a representative image of fluorescence in situ hybridization using a LSI 13 (13q14) probe spanning the RB1 region, and an LSI TP53 probe as a control. FIG. 2C exemplifies a Copy Number Variation (CNV) analysis of chromosome 13 (Chr_13). FIG. 2D exemplifies WTS analysis of mRNA abundance of indicated proteins in PBC, serial biopsies of Pt7. MCL JEKO-1 cells are treated with PD 0332991 for 72 h or left untreated as a control in E. FIG. 2E exemplifies immunoblotting of indicated proteins in PBC, serial biopsies of Pt7. MCL JEKO-1 cells are treated with PD 0332991 for 72 h or left untreated as a control in E. * indicates a lower exposure.

FIG. 3A exemplifies cells from 4 MCL cell lines cultured with Ibrutinib at indicated concentrations for 72 h. Viability is determined by Trypan blue exclusion staining in triplicate and DNA fragmentation by ToPro-3 staining and FACS analysis. FIG. 3B exemplifies cell cycle analysis (BrdU/PI double staining) of MCL cells cultured with Ibrutinib for 72 h (1 µM). The number in the FACS profile indicates the percentage of cells in sub-G1 and S phase. FIG. 3C exemplifies a schema for sequential treatment with PD 0332991 (PD) and Ibrutinib (Left), and FACS analysis of apoptosis by AnnexinV-FITC (A-V) and PI double staining at 96 h after Ibrutinib addition (1 µM for JEKO-1, MAVER-1 and MINO and 0.1 µM for SP53), with or without prior incubation with PD (Middle). Number of total live cells. *p<0.05 (Right). FIG. 3D exemplifies a WTS analysis of PIK3IP1 in PBCs and serial biopsies of Pt7. FIG. 3E exemplifies a q-RT-PCR analysis of PIK3IP1 mRNA expression in MCL cells cultured sequentially with PD (30 h) or Ibrutinib (24 h) or both, or left untreated. FIG. 3F exemplifies cell viability as the percentage of control (absence of Ibrutinib) in MCL cell lines infected with PIK3IP1 shRNA or LacZ shRNA lentivirus and treated with PD (72 h) and Ibrutinib (48 h, 1 µM). *p<0.05

FIG. 4A exemplifies a model of cell signaling upon administration of a CDK4 inhibitor (PD 0332991). FIG. 4B exemplifies a model of cell signaling upon administration of a PI3K inhibitor.

FIG. 7A exemplifies a complex karyotype with multiple numerical and structural abnormalities in nine of 10 evaluated metaphase cells from the spleen at relapse (r_IbSP). The clonal abnormalities include additional chromosomal material of unknown origin on 1q, 2q, 8p, and 21q, interstitial deletion of 6q, monosomy of chromosomes 2, 10, 11, 13, 14, 15, and 3~7 marker chromosomes. FIG. 7B exemplifies a representative image of a fluorescence in situ hybridization assay using spectrum labeled LSI CCND1 probe and spectrum labeled LSI IGH probe. The two fusion signals exemplify the presence of a reciprocal t(11; 14) translocation. The signals exemplify the normal CCND1 and IGH alleles respectively.

FIG. 8A exemplifies a Copy Number Variation (CNV) of WES data before Ibrutinib treatment (p_Ib1). FIG. 8B exemplifies a Copy Number Variation (CNV) of WES data after Ibrutinib relapse (r_IbBM). FIG. 8C exemplifies a Copy Number Variation (CNV) of WES data after Ibrutinib relapse (r_IbBM) of Chr21q22.3.

FIG. 10 exemplifies a wild type BTK sequence as SEQ ID NO:1.

DETAILED DESCRIPTION OF THE INVENTION

Certain Terminology

Figure 1A:
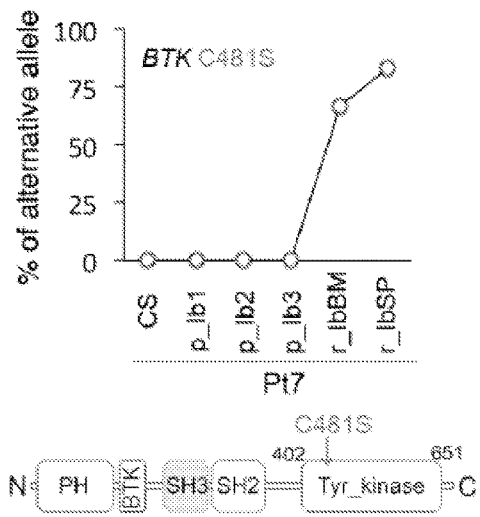
FIG. 1A-FIG. 1E exemplify characteristics of the C481S mutation.
Figure 1B:
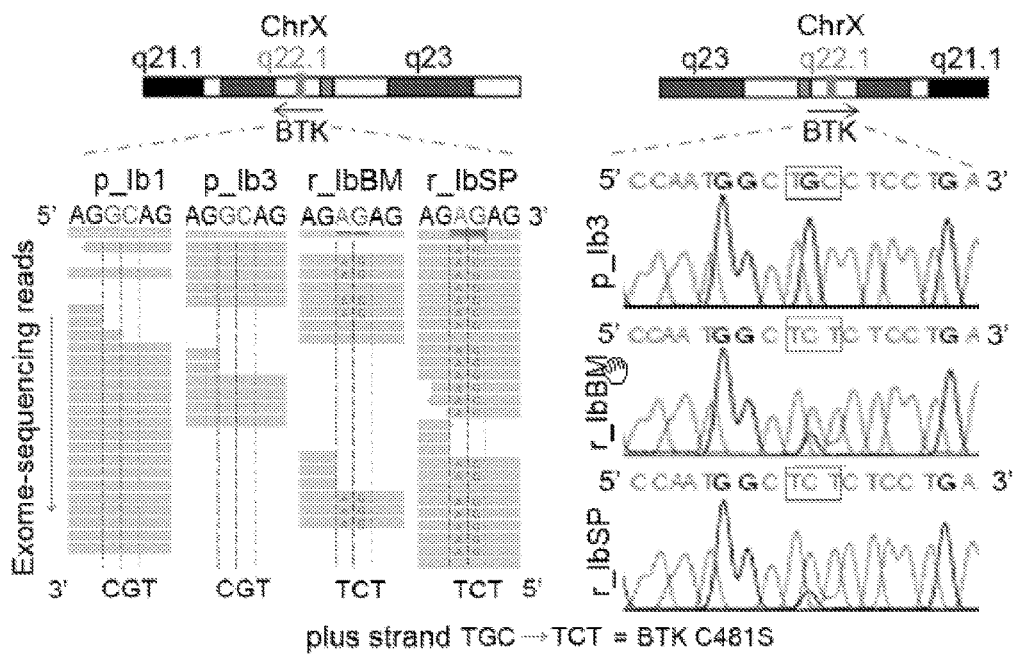

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, "amelioration" includes, but is not limited to, lessening of the severity of a B cell proliferative disorders (e.g., mantle cell lymphoma), whether permanent or temporary, lasting or transient, that can be attributed to or associated with administration of the compound or composition.

The term "Bruton's tyrosine kinase," or BTK, as used herein, refers to Bruton's tyrosine kinase from *Homo sapiens*, as disclosed in, e.g., U.S. Pat. No. 6,326,469 (GenBank Accession No. NP 000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEEL-YSSARQ").

The term "homologous cysteine," as used herein refers to a cysteine residue found within a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

The term "covalent BTK inhibitor", as used herein, refers to an inhibitor that reacts with Btk to form a covalent complex. In some embodiments, the covalent Btk inhibitor is an irreversible Btk inhibitor.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase, as shown in FIG. 7.

The terms "individual", "patient" and "subject" are used interchangeable. They refer to a mammal (e.g., a human) which is the object of treatment, or observation. The term is not to be construed as requiring the supervision of a medical practitioner (e.g., a physician, physician's assistant, nurse, orderly, hospice care worker).

The terms "treat," "treating" or "treatment", as used herein, include lessening the severity of a B cell proliferative disorders (e.g., mantle cell lymphoma), delaying the onset of a B cell proliferative disorders (e.g., mantle cell lymphoma), slowing the development of a B cell proliferative disorders (e.g., mantle cell lymphoma), causing regression/remission of a B cell proliferative disorders (e.g., mantle cell lymphoma), relieving a condition caused by a B cell proliferative disorders (e.g., mantle cell lymphoma), or stopping symptoms which result from a B cell proliferative disorders (e.g., mantle cell lymphoma). The terms "treat," "treating" or "treatment", include, but are not limited to, prophylactic and/or therapeutic treatments.

B Cell Lymphomas

Disclosed herein, in certain embodiments, are methods of treating a B cell proliferative disorder in an individual in need thereof comprising administering to the individual a TEC inhibitor and a CDK4 inhibitor (e.g., a selective CDK4 inhibitor, e.g., palbociclib). In some embodiments, the TEC inhibitor comprises a BTK inhibitor or an ITK inhibitor. In some embodiments, the TEC inhibitor is an ITK inhibitor. In some embodiments, disclosed herein are methods of treating a B cell proliferative disorder in an individual in need thereof comprising administering to the individual an ITK inhibitor and a CDK4 inhibitor (e.g., a selective CDK4 inhibitor, e.g., palbociclib).

In some embodiments, the TEC inhibitor is a BTK inhibitor. In some embodiments, the BTK inhibitor is a covalent BTK inhibitor. In some embodiments, described herein are methods of treating a B cell proliferative disorder in an individual in need thereof comprising administering to the individual a covalent Btk inhibitor (e.g., an irreversible covalent Btk inhibitor) and a CDK4 inhibitor (e.g., a selective CDK4 inhibitor, e.g., palbociclib). In some embodiments, the covalent Btk inhibitor is PCI-32765 (Ibrutinib), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the covalent BTK inhibitor is ibrutinib. In some instances, described herein are methods of treating a B cell proliferative disorder in an individual in need thereof comprising administering to the individual an ITK inhibitor and a CDK4 inhibitor (e.g., a selective CDK4 inhibitor, e.g., palbociclib). In some embodiments, the B cell proliferative disorder is refractory to the covalent Btk inhibitor (e.g., an irreversible covalent Btk inhibitor, e.g., ibrutinib). In some embodiments, the B cell proliferative disorder is relapsed. In some embodiments, the B cell proliferative disorder is an ibrutinib-resistant B cell proliferative disorder. In some embodiments, the B cell proliferative disorder is an ibrutinib-sensitive B cell proliferative disorder. In some embodiments, the B cell proliferative disorder is mantle cell lymphoma.

In some embodiments, the B cell proliferative disorder is mantle cell lymphoma (MCL). In some embodiments, the mantle cell lymphoma is relapsed or refractory to a covalent Btk inhibitor (e.g., ibrutinib). In some embodiments, the MCL is an ibrutinib-resistant MCL. In some embodiments, the MCL is an ibrutinib-sensitive MCL.

In some embodiments, the B cell proliferative disorder is a chronic lymphocytic leukemia (CLL), small lymphocytic lymphoma (SLL), high risk CLL, or a non-CLL/SLL lymphoma. In some embodiments, the B cell proliferative disorder is follicular lymphoma, diffuse large B-cell lymphoma (DLBCL), mantle cell lymphoma, Waldenstrom's macroglobulinemia, multiple myeloma, marginal zone lymphoma, Burkitt's lymphoma, non-Burkitt high grade B cell lymphoma, or extranodal marginal zone B cell lymphoma. In some embodiments, the B cell proliferative disorder is acute or chronic myelogenous (or myeloid) leukemia, myelodysplastic syndrome, or acute lymphoblastic leukemia. In some embodiments, the B cell proliferative disorder is relapsed or refractory diffuse large B-cell lymphoma (DLBCL), relapsed or refractory mantle cell lymphoma, relapsed or refractory follicular lymphoma, relapsed or refractory CLL; relapsed or refractory SLL; relapsed or refractory multiple myeloma. In some embodiments, the B cell proliferative disorder is a B cell proliferative disorder that is classified as high-risk. In some embodiments, the B cell proliferative disorder is high risk CLL or high risk SLL.

B-cell proliferative disorders are neoplasms of the blood and encompass, inter alia, non-Hodgkin lymphoma, multiple myeloma, and leukemia. They can originate either in the lymphatic tissues (as in the case of lymphoma) or in the bone marrow (as in the case of leukemia and myeloma), and they all are involved with the uncontrolled growth of lymphocytes or white blood cells. There are many subtypes of B cell proliferative disorders. The disease course and treatment of B cell proliferative disorder is dependent on the B cell proliferative disorder subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment.

Disclosed herein, in certain embodiments, are methods of treating a non-Hodgkin lymphoma in an individual in need thereof, comprising administering to the individual a TEC inhibitor (e.g., an ITK inhibitor, a BTK inhibitor, e.g. a covalent BTK inhibitor) and a CDK4 inhibitor (e.g., a selective CDK4 inhibitor, e.g., palbociclib). Disclosed herein, in certain embodiments, are methods of treating a non-Hodgkin lymphoma in an individual in need thereof, comprising administering to the individual a covalent BTK inhibitor (e.g., an irreversible covalent Btk inhibitor, e.g., ibrutinib) and a CDK4 inhibitor (e.g., a selective CDK4 inhibitor, e.g., palbociclib). In some embodiments, the non-Hodgkin lymphoma is refractory to the covalent Btk inhibitor (e.g., an irreversible covalent Btk inhibitor, e.g., ibrutinib). In some embodiments, the non-Hodgkin lymphoma is relapsed. In some embodiments, the non-Hodgkin lymphoma is an ibrutinib-resistant non-Hodgkin lymphoma. In some embodiments, the non-Hodgkin lymphoma is an ibrutinib-sensitive non-Hodgkin lymphoma. In some embodiments, the non-Hodgkin lymphoma is mantle cell lymphoma.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lympoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

Disclosed herein, in certain embodiments, is a method for treating a mantle cell lymphoma (MCL) in an individual in need thereof, comprising administering to the individual a TEC inhibitor and a CDK4 inhibitor (e.g., a selective CDK4 inhibitor, e.g., palbociclib). In some embodiments, the TEC inhibitor comprises a BTK inhibitor or an ITK inhibitor. In some embodiments, the TEC inhibitor is an ITK inhibitor. In some instances, described herein is a method for treating a mantle cell lymphoma (MCL) in an individual in need thereof, comprising administering to the individual an ITK inhibitor and a CDK4 inhibitor (e.g., a selective CDK4 inhibitor, e.g., palbociclib).

In some embodiments, the TEC inhibitor is a BTK inhibitor. In some embodiments, the BTK inhibitor is a covalent BTK inhibitor. In some embodiments, described herein is a method for treating a mantle cell lymphoma (MCL) in an individual in need thereof, comprising administering to the individual a covalent Btk inhibitor (e.g., an irreversible covalent Btk inhibitor) and a CDK4 inhibitor (e.g., a selective CDK4 inhibitor, e.g., palbociclib). In some embodiments, the covalent Btk inhibitor is PCI-32765 (Ibrutinib), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the covalent BTK inhibitor is ibrutinib. In some instances, described herein is a method for treating a mantle cell lymphoma (MCL) in an individual in need thereof, comprising administering to the individual ibrutinib and a CDK4 inhibitor (e.g., a selective CDK4 inhibitor, e.g., palbociclib). In some embodiments, the mantle cell lymphoma (MCL) is refractory to the covalent Btk inhibitor (e.g., an irreversible covalent Btk inhibitor, e.g., ibrutinib). In some embodiments, the mantle cell lymphoma (MCL) is relapsed. In some embodiments, the MCL is an ibrutinib-resistant MCL. In some embodiments, the MCL is an ibrutinib-sensitive MCL As used herein, the term, "Mantle cell lymphoma" refers to a subtype of B-cell lymphoma with a poor prognosis. The overall survival for MCL patients is about 30 to 43 months and fewer than 15% of the patients are long-term survivors. The average age of patients is in the early 60s. In some instances, men are often affected. The lymphoma is usually widespread when it is diagnosed, involving lymph nodes, bone marrow, and, very often, the spleen. Mantle cell lymphoma is not a very fast growing lymphoma, but is difficult to treat.

Only about 5% of lymphomas are of the MCL type. In some instances, MCL is further stratified based on its clinical course such as an indolent clinical course which is characterized by non-nodal leukemia disease, or blastoid and pleomorphic MCLs which are associated with advanced and aggressive disease.

MCL is characterized by a CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11; 14)(q13; q32). In some instances, the translocation at t(11; 14)(q13; q32) leads to activation of cyclin-dependent kinase 4 (CDK4). CDK4 is an enzyme of the cyclin-dependent kinase family, and is involved in the cell cycle G1 phase progression.

In some instances, the activation of CDK4 leads to an elevated expression level of CDK4. In some instances, the elevated expression level of CDK4 is an increased expression level. In some instances, the increased expression level is an increased protein expression level. In some instances, the increased expression level is an increased gene expression level. In some instances, the elevated expression level is compared to the expression level of a control. In some cases, the elevated expression level is at most 1, 2, 3, 4, 5, 6, 7, 8, 9, 10, 15, 20, 30, 40, 50, 60, 70, 80, 90, 100, 500, 1000, 5000 fold or higher compared to the expression level of a control. In some cases, the elevated expression level is at least 1, 2, 3, 4, 5, 6, 7, 8, 9, 10, 15, 20, 30, 40, 50, 60, 70, 80, 90, 100, 500, 1000, 5000 fold or lower compared to the expression level of a control.

In some instances, the expression level of CDK4 is used to stratify patients having MCL for a therapeutic treatment. In some instances, the expression level of CDK4 is used to monitor the progression of a therapeutic regiment, or to modulate a therapeutic regiment. In some instances, the expression level of CDK4 in combination with one or more additional cytogenetic abnormalities is used for patient selection or therapeutic regiment optimization.

In some instances, the additional cytogenetic abnormalities include mutations associated with BTK; MYC translocation and/or gene amplification; inactivation of cell cycle inhibitors p16/INK4A and p14/ARF; gains of 3q, 12q and losses of 9p, 9q, 17p, 19p, and 6q24/25; mutations in TP53; truncation or missense mutations of within the PI3K domain of the ATM gene; and mutations within the NOTCH1 gene, which produces a C-terminal truncated protein with increased oncogenic activity; and/or mutations associated with CD79A, CD79B, SYK, LYN, PLCG2, PRKCB, UBR5, CCND1, NOTCH2, BIRC3, WHSC1 (also known as MMSET or NSD2), MEF2B, TLR2, MLL2, TRAPPC10, BRAP, C14ORF159, RC3H1, GTSE1, DNMT1, BYSL, RSF1, TAP2, BDH1, KHDRBS2, RLP28, and PPP1R2. As used herein, a mutation refers to an insertion, a substitution, a deletion, a missense mutation, or a combination thereof.

In some embodiments, a mutation within the BTK gene includes a mutation at amino acid positions L11, K12, S14, K19, F25, K27, R28, R33, Y39, Y40, E41, I61, V64, R82, Q103, V113, S115, T117, Q127, C154, C155, T184, P189, P190, Y223, W251, R288, L295, G302, R307, D308, V319, Y334, L358, Y361, H362, H364, N365, S366, L369, I370M, R372, L408, G414, Y418, I429, K430, E445, G462, Y476, M477, C481, C502, C506, A508, M509, L512, L518, R520, D521, A523, R525, N526, V535, L542, R544, Y551, F559, R562, W563, E567, 5578, W581, A582, F583, M587, E589, S592, G594, Y598, A607, G613, Y617, P619, A622, V626, M630, C633, R641, F644, L647, L652, V1065, and/or A1185, as set forth in SEQ ID NO:1 (FIG. 10). In some embodiments, a mutation within the BTK gene is selected from among L11P, K12R, S14F, K19E, F25S, K27R, R28H, R28C, R28P, T33P, Y3S9, Y40C, Y40N, E41K, I61N, V64F, V64D, R82K, Q103Q5FSSVR, V113D, S115F, T117P, Q127H, C1545, C155G, T184P, P189A, Y223F, W251L, R288W, R288Q, L295P, G302E, R307K, R307G, R307T, D308E, V319A, Y334S, L358F, Y361C, H362Q, H364P, N365Y, S366F, L369F, I370M, R372G, L408P, G414R, Y418H, I429N, K430E, E445D, G462D, G462V, Y476D, M477R, C481S, C502F, C502W, C506Y, C506R, A508D, M5091, M509V, L512P, L512Q, L518R, R520Q, D521G, D521H, D521N, A523E, R525G, R525P, R525Q, N526K, V535F, L542P, R544G, R544K, Y551F, F559S, R562W, R562P, W563L, E567K, S578Y, W581R, A582V, F583S, M587L, E589D, E589K, E589G, S592P, G594E, Y598C, A607D, G613Y, Y617E, P619A, P619S, A622P, V626G, M630I, M630K, M630T, C633Y, R641C, F644L, F644S, L647P, L652P, V10651, and A1185V, as set forth in SEQ ID NO:1 (FIG. 10). In some embodiments, the mutation in BTK is at amino acid position 481. In some embodiments, the mutation in BTK is C481S. In some embodiments, the mutations in BTK confer resistance in a B cell proliferative disorder to a TEC inhibitor (e.g. ITK inhibitor, BTK inhibitor such as ibrutinib). In some embodiments, C481S mutation in BTK confers resistance in a B cell proliferative disorder to a TEC inhibitor (e.g. ITK inhibitor, BTK inhibitor such as ibrutinib).

In some embodiments, a mutation within PLCγ2 is a mutation at amino acid residue 665, 707, or a combination thereof. In some embodiments, the mutation is R665W and 5707F.

In some embodiments, a mutation within Cyclin D1 (CCND1) includes a mutation at amino acid residue positions 47, 44, 290, 46, 42, and/or 41. In some embodiments, a mutation within CCND1 includes C47S, Y44S, Y44Q, Y44D, V290G, K46E, V42E, or S41T.

Wolf-Hischhorn syndrome candidate 1 (WHSC1) encodes a histone 3 methyltransferase of lysine-36 (H3K36). In some embodiments, WHSC1 protein contains mutations at amino acid residue position 1099 and/or 1150. In some embodiments, WHSC1 protein contains mutations E1099K and/or T1150A.

Myeloid/lymphoid or mixed-lineage leukemia protein 2 (MLL2) is a histone methyltransferase and in some instances, contains mutations in its FYRN and FYRC domains. In some embodiments, MLL2 protein contains mutations at amino acid residue position 5272, 2771, 1724, 3604, 5225, and/or 2839. In some embodiments, MLL2 protein contains mutations A5272P, R2771, D1724fs (frame shift), Q3604, R5225C, and/or S2839.

Myocyte enhancer factor 2B (MEF2B) is a member of the MADS/MEF2 family of DNA binding proteins. In some embodiments, MEF2B protein contains mutations at amino acid residue position 23 and/or 49. In some embodiments, MEF2B protein contains mutations K23R and/or N49S.

The ATM serine/threonine kinase gene is involved in cellular development and DNA repair. In some embodiments, ATM protein contains mutations at amino acid residue position 1338, 323, 2730, 3008, 2526, 2437, 2727, 1959, 2104, 2427, 2308, 2297, 2694, 148, 593, 1618, and/or 2489. In some embodiments, ATM protein contains mutations Q1448A, I323V, Q2730R, R3008C, R2526S, Y2437S, V2727A, E1959K, W2104, L2427L, A2308T, Q2297, G2694K, R248Q, T593fs (frame shift), R1618, and/or S2489F.

Baculoviral IAP repeat containing 3 (BIRC3) gene encodes a member of the IAP family of proteins that inhibit apoptosis by interaction with tumor necrosis factor receptor-associated factors TRAF1 and TRAF2. In some embodiments, BIRC3 protein contains mutations at amino acid residue position 552, 560, 550, 575, 563, 591, 556, 600, and/or 557. In some embodiments, BIRC3 protein contains mutations Q552, C560Y, R550, L575V, K563, R591fs (frame shift), T556fs, R600G, and/or C557G.

Neurogenic locus notch homolog protein 2 (NOTCH2) is a type 1 transmembrane protein that is involved in cellular development. In some embodiments, NOTCH2 protein contains mutations at amino acid residue position 2400, 2360, 2293, 2292, 2391, and/or 2285. In some embodiments, NOTCH2 protein contains mutations 82400, Q2360, H2293fs (frame shift), K2292fs, S2391fs, and/or Q2285.

In some embodiments, NOTCH1 protein contains mutations at amino acid residue position 2515, 2504, 2281, 2487, and/or 2428. In some embodiments, NOTCH1 protein contains mutations P2515fs (frame shift), V2504fs, G2281fs, Q2487, and/or H2428fs.

In some embodiments, the Toll-like receptor 2 (TLR2) protein contains mutations at amino acid residue position 327 and/or 298. In some embodiments, TLR2 protein contains mutations D327V and/or Y298S. In some embodiments, the TLR2 protein has the accession number AAH33756. In some embodiments, the TLR2 gene has the GeneID: 7097.

In some embodiments, the BRCA1 associated protein (BRAP) protein contains a mutation at amino acid residue position 80. In some embodiments, the BRAP protein contains mutation N80Y. In some embodiments, the BRAP protein has the accession number Q7Z569. In some embodiments, the BRAP gene has the GeneID: 8315.

In some embodiments, the UPF0317 protein C14orf159, mitochondrial (C14orf159) protein contains a mutation at amino acid residue position 310. In some embodiments, the C14orf159 protein contains mutation D310H. In some embodiments, the C14orf159 protein has the accession number CAG33570. In some embodiments, the C14orf159 gene has the GeneID: 80017.

In some embodiments, the Ring Finger and CCCH-type domains 1 (RC3H1) protein contains a mutation at amino acid residue position 1116. In some embodiments, the RC3H1 protein contains mutation G1116V. In some embodiments, the RC3H1 protein has the accession number AAI44409. In some embodiments, the RC3H1 gene has the GeneID: 149041.

In some embodiments, the tumor protein p50 (TP53) protein contains a mutation at amino acid residue position 273. In some embodiments, the TP53 protein contains mutation R273C. In some embodiments, the TP53 protein has the accession number AEX20383. In some embodiments, the TP53 gene has the GeneID: 7157.

In some embodiments, the G-2 and S-phase expressed 1 (GTSE1) protein contains a mutation at amino acid residue position 295. In some embodiments, the GTSE1 protein contains mutation S295N. In some embodiments, the GTSE1 protein has the accession number CAJ86449. In some embodiments, the GTSE1 gene has the GeneID: 51512.

In some embodiments, the DNA (cytosine-5_-methyltransferase 1 (DNMT1) protein contains a mutation at amino acid residue position 101. In some embodiments, the DNMT1 protein contains mutation R101 W. In some embodiments, the DNMT1 protein has the accession number AAI44094. In some embodiments, the DNMT1 gene has the GeneID: 1786.

In some embodiments, the myocyte enhancer factor 2B (MEF2B) protein contains a mutation at amino acid residue position 23. In some embodiments, the MEF2B protein contains mutation K23R. In some embodiments, the MEF2B protein has the accession number NP_001139257. In some embodiments, the MEF2B gene has the GeneID: 100271849.

In some embodiments, the bystin-like (BYSL) protein contains a mutation at amino acid residue position 85. In some embodiments, the BYSL protein contains mutation R85C. In some embodiments, the BYSL protein has the accession number Q13895. In some embodiments, the BYSL gene has the GeneID: 705.

In some embodiments, the remodeling and spacing factor 1 (RSF1) protein contains a mutation at amino acid residue position 72. In some embodiments, the RSF1 protein contains mutation L72F. In some embodiments, the RSF1 protein has the accession number Q96T23. In some embodiments, the RSF1 gene has the GeneID: 51773.

In some embodiments, the transporter 2, ATP-binding cassette, sub-family B (MDR/TAP) (TAP2) protein contains a mutation at amino acid residue position 313. In some embodiments, the TAP2 protein contains mutation R313H. In some embodiments, the TAP2 protein has the accession number AHW47975. In some embodiments, the TAP2 gene has the GeneID: 6891.

In some embodiments, the 3-hydroxybutyrate dehydrogenase, type 1(BDH1) protein contains a mutation at amino acid residue position 130. In some embodiments, the BDH1 protein contains mutation N130Y. In some embodiments, the BDH1 protein has the accession number Q02338. In some embodiments, the BDH1 gene has the GeneID: 622.

In some embodiments, the KHDRBS2 protein contains a mutation at amino acid residue position 333. In some embodiments, the KH domain containing, RNA binding, signal transduction associated 2 (KHDRBS2) protein contains mutation P333L. In some embodiments, the G KHDRBS2 TSE1 protein has the accession number Q5VWX1. In some embodiments, the KHDRBS2 gene has the GeneID: 202559.

In some embodiments, the putative leucine-rich repeat disease resistance protein (RLP28) protein contains a mutation at amino acid residue position 115. In some embodiments, the RLP28 protein contains mutation G115E.

In some embodiments, the protein phosphatase 1, regulatory (inhibitor) subunit 2 (PPP1R2) protein contains a mutation at amino acid residue position 44. In some embodiments, the PPP1R2 protein contains mutation S44F. In some embodiments, the GTSE1 protein has the accession number P41236. In some embodiments, the GTSE1 gene has the GeneID: 5504.

In some instances, the expression level of CDK4 and an additional cytogenetic abnormality selected from mutations associated with BTK; MYC translocation and/or gene amplification; inactivation of cell cycle inhibitors p16/INK4A and p14/ARF; gains of 3q, 12q and losses of 9p, 9q, 17p, 19p, and 6q24/25; mutations in TP53; truncation or missense mutations of within the PI3K domain of the ATM gene; and mutations within the NOTCH1 gene; and/or mutations associated with CD79A, CD79B, SYK, LYN, PLCG2, PRKCB, UBR5, CCND1, NOTCH2, BIRC3, WHSC1 (also known as MMSET or NSD2), MEF2B, TLR2, MLL2, TRAPPC10, BRAP, C14ORF159, RC3H1, GTSE1, DNMT1, BYSL, RSF1, TAP2, BDH1, KHDRBS2, RLP28, and PPP1R2 are used to stratify patients having MCL for a therapeutic treatment. In some instances, the expression level of CDK4 and an additional cytogenetic abnormality selected from mutations associated with BTK; MYC translocation and/or gene amplification; inactivation of cell cycle inhibitors p16/INK4A and p14/ARF; gains of 3q, 12q and losses of 9p, 9q, 17p, 19p, and 6q24/25; mutations in TP53; truncation or missense mutations of within the PI3K domain of the ATM gene; and mutations within the NOTCH1 gene; and/or mutations associated with CD79A, CD79B, SYK, LYN, PLCG2, PRKCB, UBR5, CCND1, NOTCH2, BIRC3, WHSC1 (also known as MMSET or NSD2), MEF2B, TLR2, MLL2, TRAPPC10, BRAP, C14ORF159, RC3H1, GTSE1, DNMT1, BYSL, RSF1, TAP2, BDH1, KHDRBS2, RLP28, and PPP1R2 are used to monitor the progression of a therapeutic regiment, or to modulate a therapeutic regiment.

In some instances, the expression level of CDK4 and a mutation selected from BTK C481 S, TRAPPC10 V600F, BRAP N80Y, C14orf159 D310H, RC3H1 G1116V, TP53 R273C, GTSE1 S295N, DNMT1 R101W, MEF2B K23R, BYSL R85C, RSF1 L72F, TAP2 R313H, BDH1 N130Y, KHDRBS2 P333L, RLP28 G115E, and PPP1R2 S44F are used to stratify patients having MCL for a therapeutic treatment. In some instances, the expression level of CDK4 and a mutation selected from BTK C481S, TRAPPC10 V600F, BRAP N80Y, C14orf159 D310H, RC3H1 G1116V, TP53 R273C, GTSE1 S295N, DNMT1 R101W, MEF2B K23R, BYSL R85C, RSF1 L72F, TAP2 R313H, BDH1 N130Y, KHDRBS2 P333L, RLP28 G115E, and PPP1R2 S44F are used to monitor the progression of a therapeutic regiment, or to modulate a therapeutic regiment.

In some instances, MCL is characterized with the translocation at t(11; 14)(q13; q32) and with one or more of the additional cytogenetic abnormalities. In some instances, MCL is characterized with one or more of the additional cytogenetic abnormalities but without the translocation at t(11; 14)(q13; q32).

In certain instances, MCL patients relapse following treatment with ibrutinib in approximately one year, sometimes with a more aggressive disease than initial presentation. In certain instances, relapsed MCL is associated with increased splenomegaly and mild lymphadenopathy, possibly attributable to differential proliferation of MCL cells in the spleen and not in the bone marrow at relapse. In certain instances, relapsed MCL is characterized by enhanced CDK4 expression and phosphorylation of Rb that accelerates progression through G1 in coordination with spleen-specific increases in Cyclin A to promote S phase entry, and Cyclin B and CDK1 for progression through G2/M.

In some embodiments, inhibiting the activity of CDK4 inhibits proliferation of MCL cells. In some embodiments, inhibiting the activity of CDK4 resensitized MCL cells refractory to ibrutinib for ibrutinib killing.

C481S Mutation

In some embodiments, the B cell lymphoma is characterized by a plurality of cells having a mutant BTK polypeptide. In some embodiments, the mutant BTK polypeptides contain one or more amino acid substitutions that confers resistance to inhibition by a covalent and/or irreversible BTK inhibitor. In some embodiments, the mutant BTK polypeptides contain one or more amino acid substitutions that confers resistance to inhibition by a covalent and/or irreversible BTK inhibitor that covalently binds to cysteine at amino acid position 481 of a wild-type BTK set forth in SEQ ID NO.: 1 (FIG. 10). In some embodiments, the mutant BTK polypeptides contain one or more amino acid substitutions that confers resistance to inhibition by a covalent and/or irreversible BTK inhibitor selected from PCI-32765 (Ibrutinib), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the mutant BTK polypeptides contain one or more amino acid substitutions that confers resistance to inhibition by ibrutinib. In some instances, the plurality of cells comprises at least two cells.

As described above in some embodiments, the modification comprises a substitution or a deletion of the amino acid at amino acid position 481 compared to a wild type BTK set forth in SEQ ID NO: 1 (FIG. 10). In some embodiments, the modification comprises substitution of the amino acid at position 481 compared to a wild type BTK set forth in SEQ ID NO: 1 (FIG. 10). In some embodiments, the modification is a substitution of cysteine to an amino acid selected from among leucine, isoleucine, valine, alanine, glycine, methionine, serine, threonine, phenylalanine, tryptophan, lysine, arginine, histidine, proline, tyrosine, asparagine, glutamine, aspartic acid and glutamic acid at amino acid position 481 of the BTK polypeptide. In some embodiments, the modification is a substitution of cysteine to an amino acid selected from among serine, methionine, or threonine at amino acid position 481 of the BTK polypeptide. In some embodiments, the modification is a substitution of cysteine to serine at amino acid position 481 of the BTK polypeptide ("C481S").

Compounds

Disclosed herein, in certain embodiments, are methods of treating a B cell proliferative disorder in an individual in need thereof comprising administering to the individual a covalent TEC inhibitor and a CDK4 inhibitor (e.g., a selective CDK4 inhibitor, e.g., palbociclib). In some embodiments, the TEC inhibitor is a BTK, ITK, TEC, RLK, or BMX inhibitor. In some embodiments, the TEC inhibitor is a BTK inhibitor or an ITK inhibitor. In some embodiments, the TEC inhibitor is a BTK inhibitor. In some embodiments, the BTK is a covalent BTK inhibitor. In some embodiments, the covalent BTK inhibitor is ibrutinib. In some embodiments, the B cell proliferative disorder is refractory to the covalent BTK inhibitor (e.g., an irreversible covalent BTK inhibitor, e.g., ibrutinib). In some embodiments, the B cell proliferative disorder is relapsed. In some embodiments, the B cell proliferative disorder is mantle cell lymphoma (MCL). In some embodiments, the MCL is an ibrutinib-resistant MCL. In some embodiments, the MCL is an ibrutinib-sensitive MCL.

Definition of standard chemistry terms are found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Unless stated otherwise, the terms used for complex moieties (i.e., multiple chains of moieties) are to be read equivalently either from left to right or right to left. For example, the group alkylenecycloalkylene refers both to an alkylene group followed by a cycloalkylene group or as a cycloalkylene group followed by an alkylene group.

The suffix "ene" appended to a group indicates that such a group is a diradical. By way of example only, a methylene is a diradical of a methyl group, that is, it is a —CH$_2$— group; and an ethylene is a diradical of an ethyl group, i.e., —CH$_2$CH$_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=CH$_2$, —C(CH$_3$)=CH$_2$, —CH=CHCH$_3$, —C(CH$_3$)=CHCH$_3$. Alkenylene groups include, but are not limited to, —CH=CH—, —C(CH$_3$)=CH—, —CH=CHCH$_2$—, —CH=CHCH$_2$CH$_2$— and —C(CH$_3$)=CHCH$_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkylhydroxy, as defined herein.

"Alkoxyalkylaminoalkyl" refers to an alkyl radical, as defined herein, substituted with an alkylamine and substituted with an alkylalkoxy, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, $3^{rd}$ Ed., John Wiley & Sons, New York, N.Y., 1999, which is incorporated herein by reference for this disclosure.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, $3^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e. a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic")

groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)2-, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Illustrative examples of cycloalkyl groups include the following moieties:

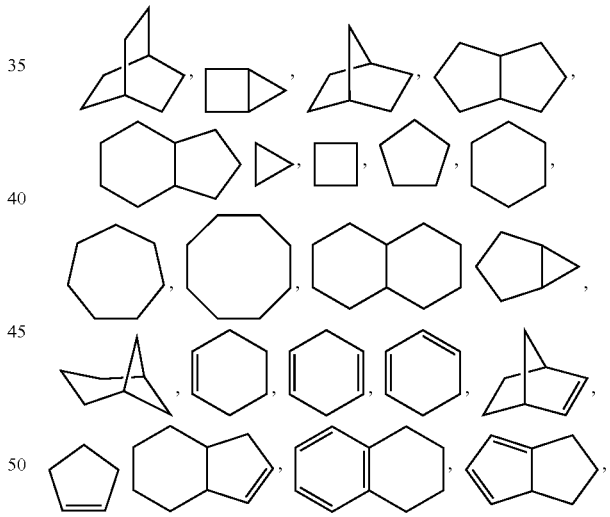

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

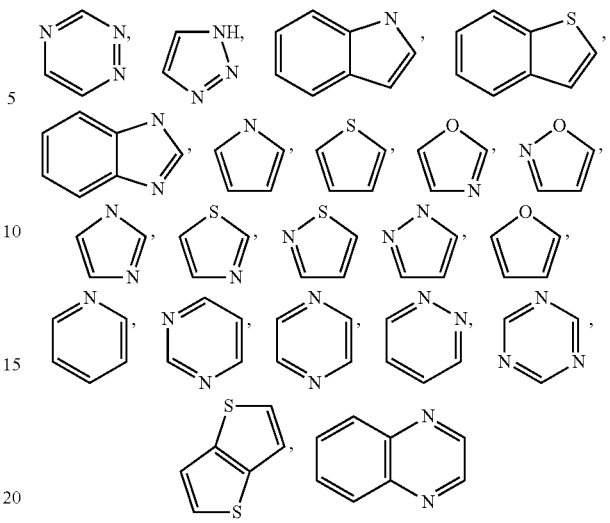

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. In some embodiments, the radicals are fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

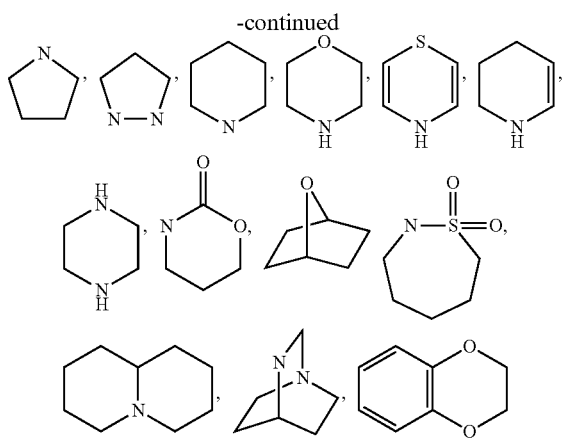

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —$CF_3$, —$CH_2CF_3$, —$CF_2CF_3$, —$CH_2CH_2CF_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, in some embodiments, up to two heteroatoms are consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O) O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$ alkyl), (substituted or unsubstituted $C_3$-$C_6$ cycloalkyl), heteroaryl, or heteroalkyl. The protecting groups that form the protective derivatives of the above substituents include those found in sources such as Greene and Wuts, above.

Covalent BTK Inhibitor Compounds

Disclosed herein, in certain embodiments, are methods of treating a B cell proliferative disorder in an individual in need thereof comprising administering to the individual a covalent Btk inhibitor (e.g., an irreversible covalent Btk inhibitor, e.g., ibrutinib) and a CDK4 inhibitor (e.g., a selective CDK4 inhibitor, e.g., palbociclib). In some embodiments, the B cell proliferative disorder is refractory to the covalent Btk inhibitor (e.g., an irreversible covalent Btk inhibitor, e.g., ibrutinib). In some embodiments, the B cell proliferative disorder is relapsed. In some embodiments, the B cell proliferative disorder is mantle cell lymphoma.

In some embodiments, the covalent Btk inhibitor is a compound of Formula (A):

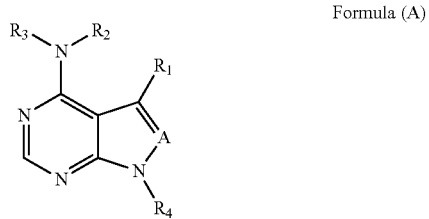

Formula (A)

wherein
  A is independently selected from N or $CR_5$;
  $R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkylene), or -(substituted or unsubstituted $C_2$-$C_6$ alkenylene);
  $R_2$ and $R_3$ are independently selected from H, lower alkyl and substituted lower alkyl;

$R_4$ is $L_3$-X-$L_4$-G, wherein,
  $L_3$ is optional, and when present is a bond, optionally substituted or unsubstituted alkylene, optionally substituted or unsubstituted cycloalkylene, optionally substituted or unsubstituted alkenylene, optionally substituted or unsubstituted alkynylene;
  X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroarylene, arylene, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
  $L_4$ is optional, and when present is a bond, substituted or unsubstituted alkylene, substituted or unsubstituted cycloalkylene, substituted or unsubstituted alkenylene, substituted or unsubstituted alkynylene, substituted or unsubstituted arylene, substituted or unsubstituted heteroarylene, substituted or unsubstituted heterocycle;
  or $L_3$, X and $L_4$ taken together form a nitrogen containing heterocyclic ring;
  G is

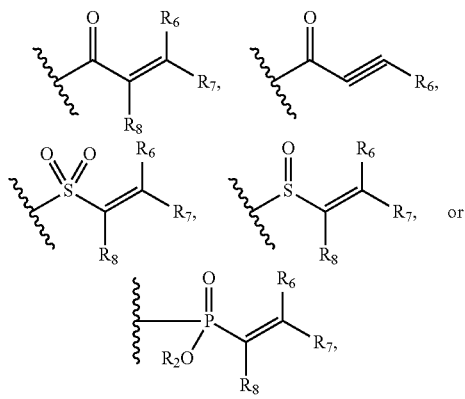

wherein,
  $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;
$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(=O), S(=O)$_2$, NH, C(O), —NHC(O)O, —OC(O)NH, —NHC(O), or —C(O)NH;
$R_9$ is selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or
$R_{11}$ is selected from H or alkyl; and
pharmaceutically active metabolites, pharmaceutically acceptable solvates, pharmaceutically acceptable salts, or pharmaceutically acceptable prodrugs thereof.

In one embodiment, the compound of Formula (A) has the structure:

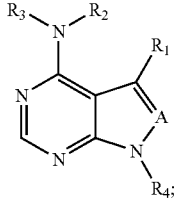

Formula (A)

wherein:
A is N;
$R_2$ and $R_3$ are each H;
$R_1$ is phenyl-O-phenyl or phenyl-S-phenyl; and
$R_4$ is $L_3$-X-$L_4$-G, wherein,
  $L_3$ is optional, and when present is a bond, optionally substituted or unsubstituted alkylene, optionally substituted or unsubstituted cycloalkylene, optionally substituted or unsubstituted alkenylene, optionally substituted or unsubstituted alkynylene;
  X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroarylene, arylene, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
  $L_4$ is optional, and when present is a bond, substituted or unsubstituted alkylene, substituted or unsubstituted cycloalkylene, substituted or unsubstituted alkenylene, substituted or unsubstituted alkynylene, substituted or unsubstituted arylene, substituted or unsubstituted heteroarylene, substituted or unsubstituted heterocycle;
  or $L_3$, X and $L_4$ taken together form a nitrogen containing heterocyclic ring;
  G is

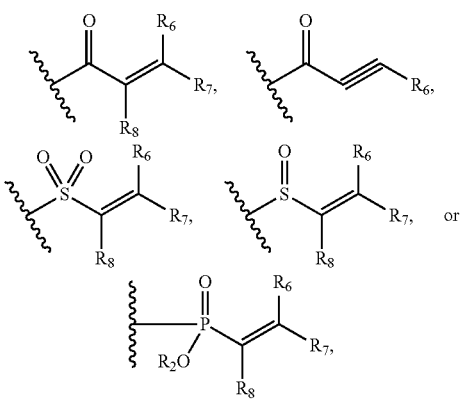

wherein,
  $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl.

In some embodiments, the covalent BTK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

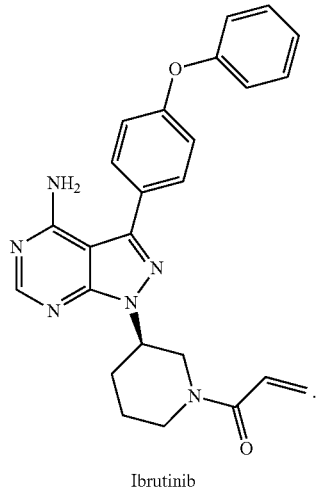 [SMILES: C=CC(=O)N1CCC[C@@H](n2nc(-c3ccc(Oc4ccccc4)cc3)c3c(N)ncnc32)C1]

Ibrutinib

Further examples of covalent Btk inhibitors may be found in the following patents and patent applications, all of which are incorporated herein in their entirety by reference: U.S. Pat. Nos. 7,514,444; 7,960,396; 8,236,812; 8,497,277; 8,563,563; 8,399,470; 8,088,781; 8,501,751; 8,008,309; 8,552,010; 7,732,454; 7,825,118; 8,377,946; 8,501,724; US Patent Pub. No. 2011-0039868; U.S. Pat. Nos. 8,232,280; 8,158,786; US Patent Pub. No. 2011-0281322; US Patent Pub. No. 2012-0088912; US Patent Pub. No. 2012-0108612; US Patent Pub. No. 2012-0115889; US Patent Pub. No. 2013-0005745; US Patent Pub. No. 2012-0122894; US Patent Pub. No. 2012-0135944; US Patent Pub. No. 2012-0214826; US Patent Pub. No. 2012-0252821; US Patent Pub. No. 2012-0252822; US Patent Pub. No. 2012-0277254; US Patent Pub. No. 2010-0022561; US Patent Pub. No. 2010-0324050; US Patent Pub. No. 2012-0283276; US Patent Pub. No. 2012-0065201; US Patent Pub. No. 2012-0178753; US Patent Pub. No. 2012-0101113; US Patent Pub. No. 2012-0101114; US Patent Pub. No. 2012-0165328; US Patent Pub. No. 2012-0184013; US Patent Pub. No. 2012-0184567; US Patent Pub. No. 2012-0202264; US Patent Pub. No. 2012-0277225; US Patent Pub. No. 2012-0277255; US Patent Pub. No. 2012-0296089; US Patent Pub. No. 2013-0035334; US Patent Pub. No. 2012-0329130; US Patent Pub. No. 2013-0018060; US Patent Pub. No. 2010-0254905; U.S. Patent App. No. 60/826,720; U.S. Patent App. No. 60/828,590; U.S. patent application Ser. No. 13/654,173; U.S. patent application Ser. No. 13/849,399; U.S. patent application Ser. No. 13/890,498; U.S. patent application Ser. No. 13/952,531; U.S. patent application Ser. No. 14/033,344; U.S. patent application Ser. No. 14/073,543; U.S. patent application Ser. No. 14/073,594; U.S. patent application Ser. No. 14/079,508; U.S. patent application Ser. No. 14/080,640; U.S. patent application Ser. No. 14/080,649; U.S. patent application Ser. No. 14/069,222; PCT App. No. PCT/US2008/58528; PCT App. No. PCT/US2012/046779; U.S. Patent App. No. 61/582,199; U.S. patent application Ser. No. 13/619,466; PCT App. No. PCT/US2012/72043; U.S. Patent App. No. 61/593,146; U.S. Patent App. No. 61/637,765; PCT App. No. PCT/US2013/23918; U.S. Patent App. No. 61/781,975; U.S. Patent App. No. 61/727,031; PCT App. No. PCT/US2013/7016; U.S. Patent App. No. 61/647,956; PCT App. No. PCT/US2013/41242; U.S. Patent App. No. 61/769,103; U.S. Patent App. No. 61/842,321; and U.S. Patent App. No. 61/884,888.

In some embodiments, the covalent Btk inhibitor is PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc).

In some embodiments, the covalent Btk inhibitor is 4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6(5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4-methoxy-2-methylphenyl]sulfanyl-1,3-thiazol-2-yl]-4-[(3,3-dimethylbutan-2-ylamino)methyl]benzamide (BMS-509744, HY-11092); or N-(5-((5-(4-Acetylpiperazine-1-carbonyl)-4-methoxy-2-methylphenyl)thio)thiazol-2-yl)-4-(((3-methylbutan-2-yl)amino)methyl)benzamide (HY11066).

In some embodiments, the covalent Btk inhibitor is:

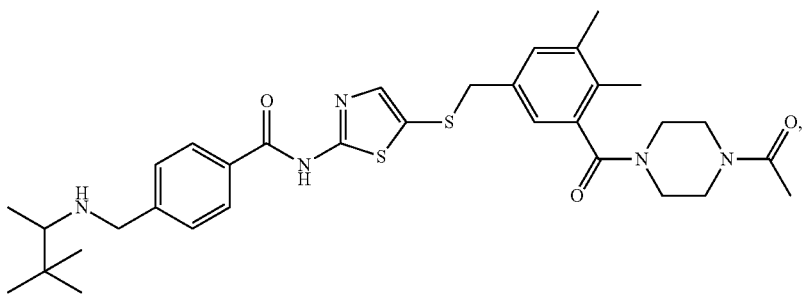

-continued
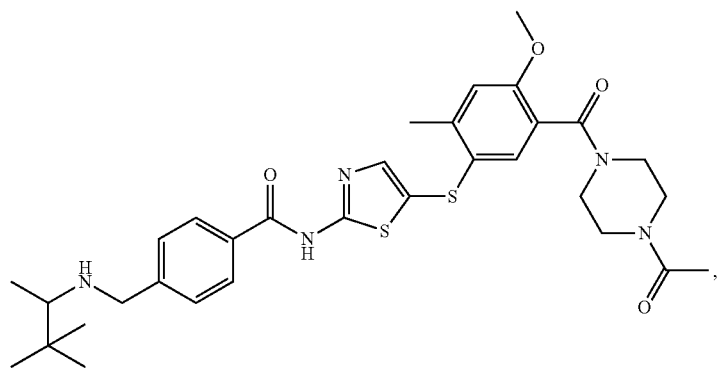
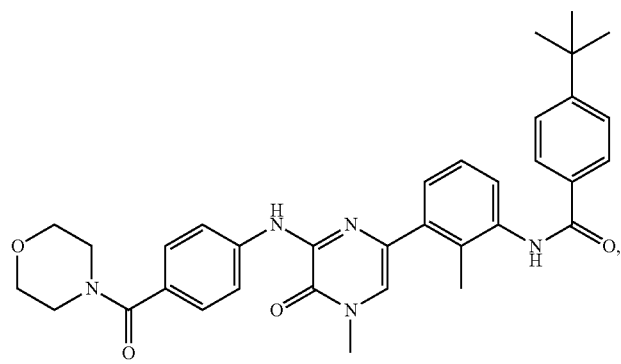
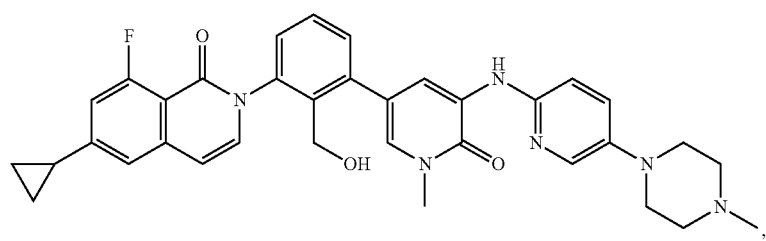
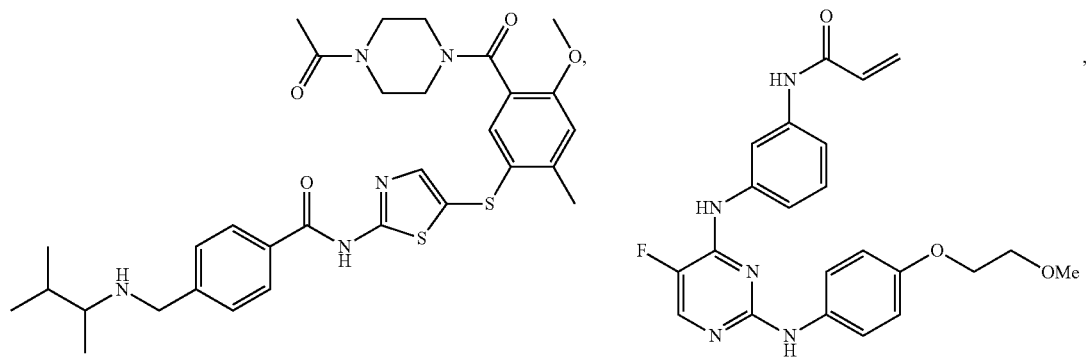

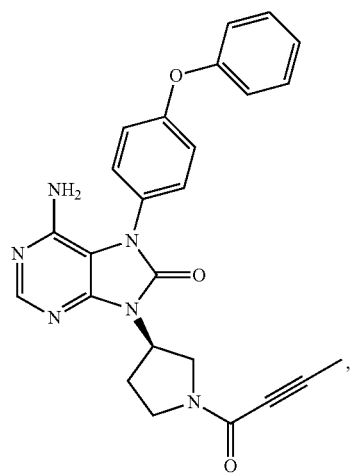
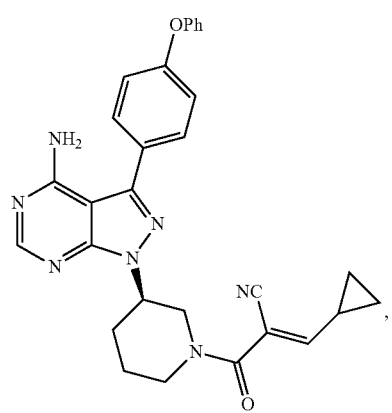
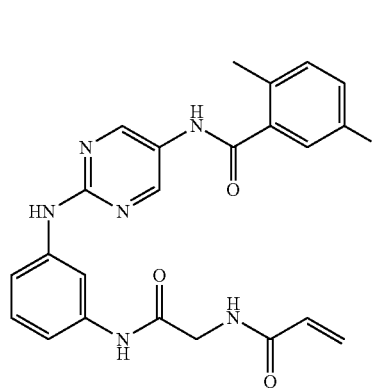
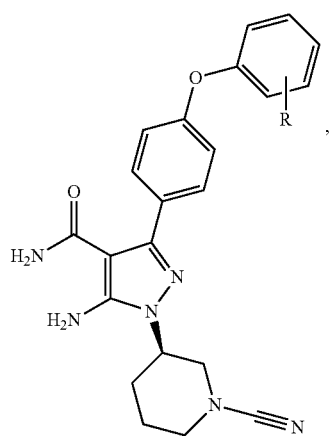
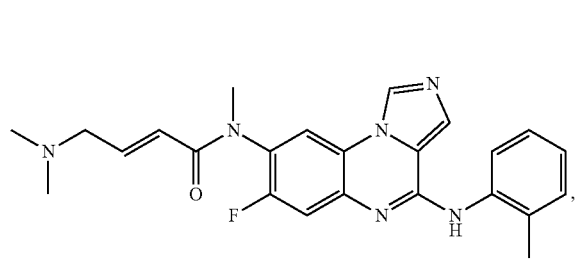
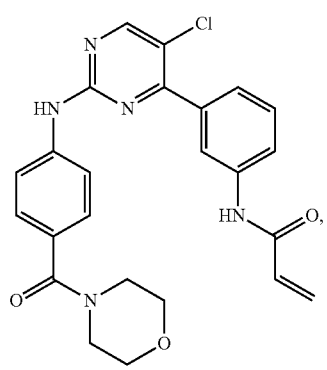

-continued
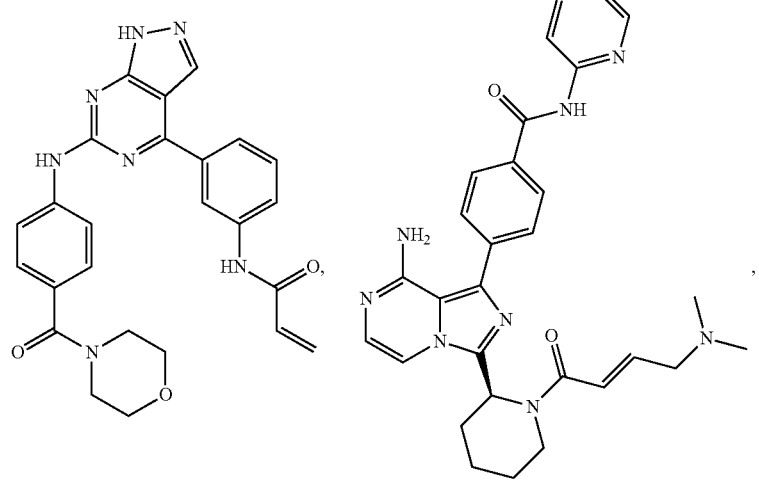
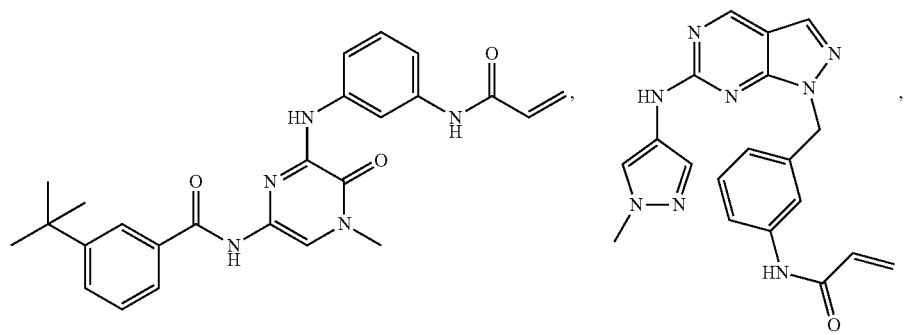
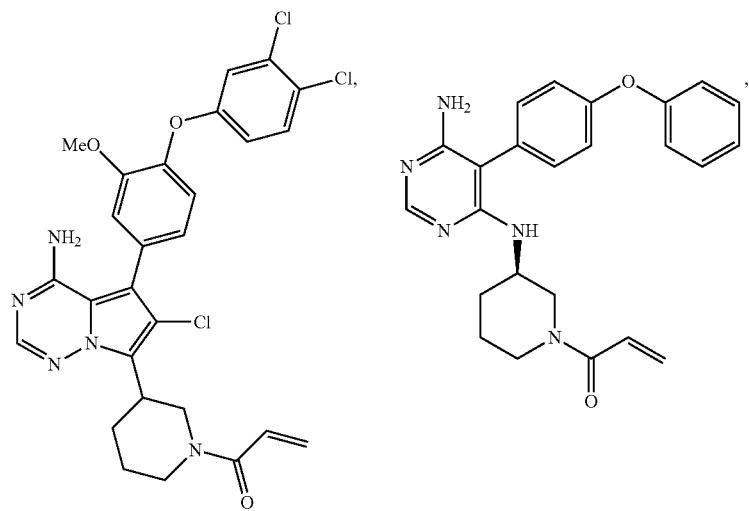

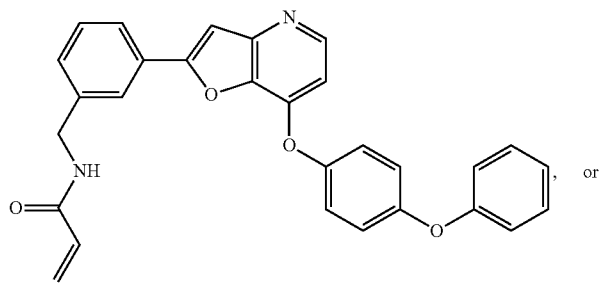 or 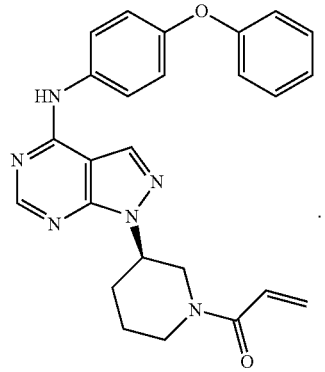

Additional TEC Family Kinase Inhibitors

BTK is a member of the Tyrosine-protein kinase (TEC) family of kinases. In some embodiments, the TEC family comprises BTK, ITK, TEC, RLK and BMX. In some embodiments, a TEC family kinase inhibitor inhibits the kinase activity of BTK, ITK, TEC, RLK and BMX. In some embodiments, a TEC family kinase inhibitor is a BTK inhibitor, which is disclosed elsewhere herein. In some embodiments, a TEC family kinase inhibitor is an ITK inhibitor. In some embodiments, a TEC family kinase inhibitor is a TEC inhibitor. In some embodiments, a TEC family kinase inhibitor is a RLK inhibitor. In some embodiments, a TEC family kinase inhibitor is a BMK inhibitor.

In some embodiments, the ITK inhibitor covalently binds to Cysteine 442 of ITK. In some embodiments, the Itk inhibitor is an Itk inhibitor compound described in WO2002/0500071, which is incorporated by reference in its entirety. In some embodiments, the Itk inhibitor is an Itk inhibitor compound described in WO2005/070420, which is incorporated by reference in its entirety. In some embodiments, the Itk inhibitor is an Itk inhibitor compound described in WO2005/079791, which is incorporated by reference in its entirety. In some embodiments, the Itk inhibitor is an Itk inhibitor compound described in WO2007/076228, which is incorporated by reference in its entirety. In some embodiments, the Itk inhibitor is an Itk inhibitor compound described in WO2007/058832, which is incorporated by reference in its entirety. In some embodiments, the Itk inhibitor is an Itk inhibitor compound described in WO2004/016610, which is incorporated by reference in its entirety. In some embodiments, the Itk inhibitor is an Itk inhibitor compound described in WO2004/016611, which is incorporated by reference in its entirety. In some embodiments, the Itk inhibitor is an Itk inhibitor compound described in WO2004/016600, which is incorporated by reference in its entirety. In some embodiments, the Itk inhibitor is an Itk inhibitor compound described in WO2004/016615, which is incorporated by reference in its entirety. In some embodiments, the Itk inhibitor is an Itk inhibitor compound described in WO2005/026175, which is incorporated by reference in its entirety. In some embodiments, the Itk inhibitor is an Itk inhibitor compound described in WO2006/065946, which is incorporated by reference in its entirety. In some embodiments, the Itk inhibitor is an Itk inhibitor compound described in WO2007/027594, which is incorporated by reference in its entirety. In some embodiments, the Itk inhibitor is an Itk inhibitor compound described in WO2007/017455, which is incorporated by reference in its entirety. In some embodiments, the Itk inhibitor is an Itk inhibitor compound described in WO2008/025820, which is incorporated by reference in its entirety. In some embodiments, the Itk inhibitor is an Itk inhibitor compound described in WO2008/025821, which is incorporated by reference in its entirety. In some embodiments, the Itk inhibitor is an Itk inhibitor compound described in WO2008/025822, which is incorporated by reference in its entirety. In some embodiments, the Itk inhibitor is an Itk inhibitor compound described in WO2011/017219, which is incorporated by reference in its entirety. In some embodiments, the Itk inhibitor is an Itk inhibitor compound described in WO2011/090760, which is incorporated by reference in its entirety. In some embodiments, the Itk inhibitor is an Itk inhibitor compound described in WO2009/158571, which is incorporated by reference in its entirety. In some embodiments, the Itk inhibitor is an Itk inhibitor compound described in WO2009/051822, which is incorporated by reference in its entirety. In some embodiments, the Itk inhibitor is an Itk inhibitor compound described in US20110281850, which is incorporated by reference in its entirety. In some embodiments, the Itk inhibitor is an Itk inhibitor compound described in WO2014/082085, which is incorporated by reference in its entirety. In some embodiments, the Itk inhibitor is an Itk inhibitor compound described in WO2014/093383, which is incorporated by reference in its entirety. In some embodiments, the Itk inhibitor is an Itk inhibitor compound described in U.S. Pat. No. 8,759,358, which is incorporated by reference in its entirety. In some embodiments, the Itk inhibitor is an Itk inhibitor compound described in WO2014/105958, which is incorporated by reference in its entirety. In some embodiments, the Itk inhibitor is an Itk inhibitor compound described in US2014/0256704, which is incorporated by reference in its entirety. In some embodiments, the Itk inhibitor is an Itk inhibitor compound described in US20140315909, which is incorporated by reference in its entirety. In some embodiments, the Itk inhibitor is an Itk inhibitor compound described in US20140303161, which is incorporated by reference in its entirety. In some embodiments, the Itk inhibitor is an Itk inhibitor compound described in WO2014/145403, which is incorporated by reference in its entirety.

In some embodiments, the Itk inhibitor has a structure selected from:

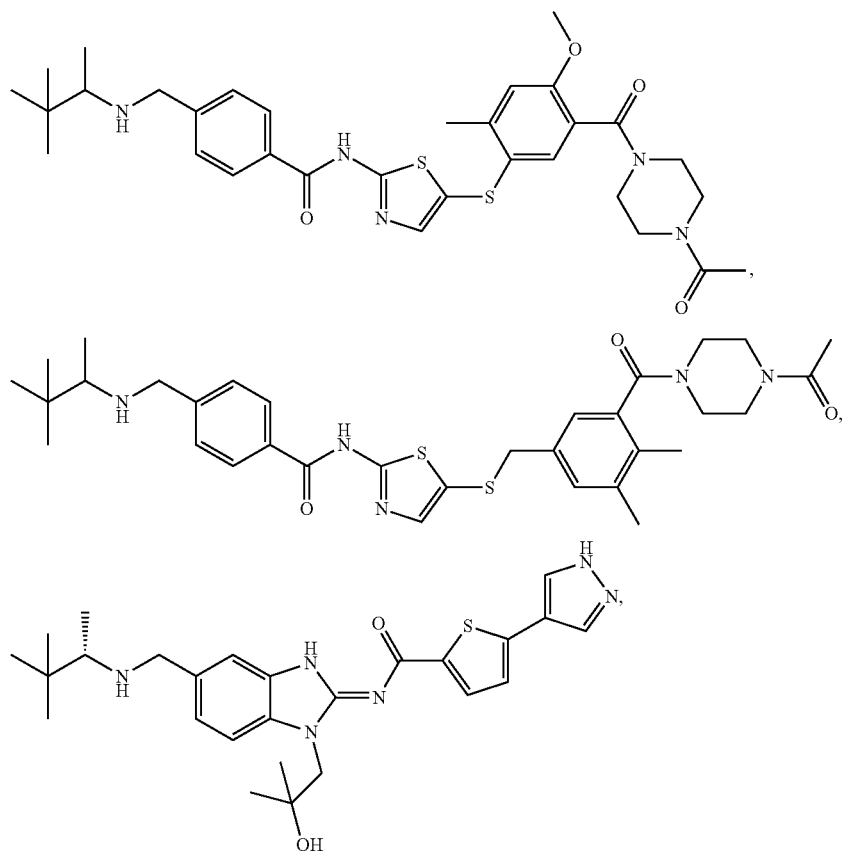
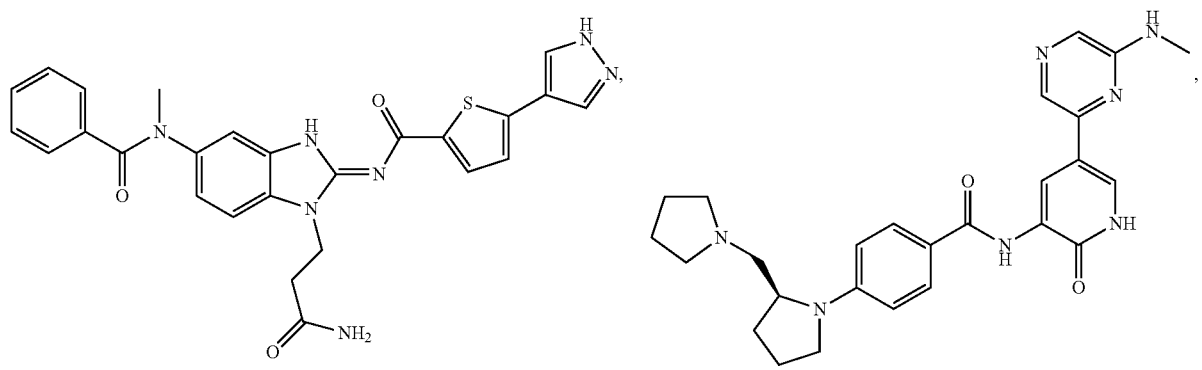
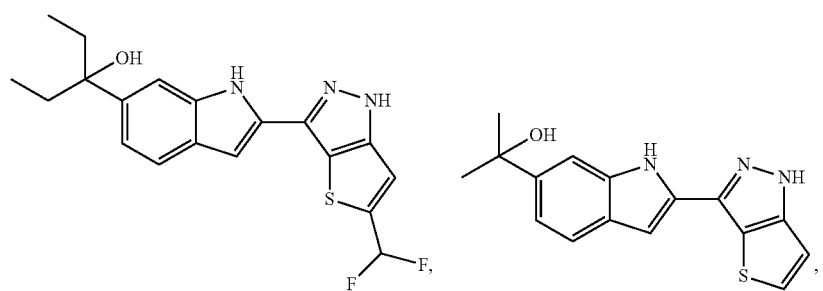

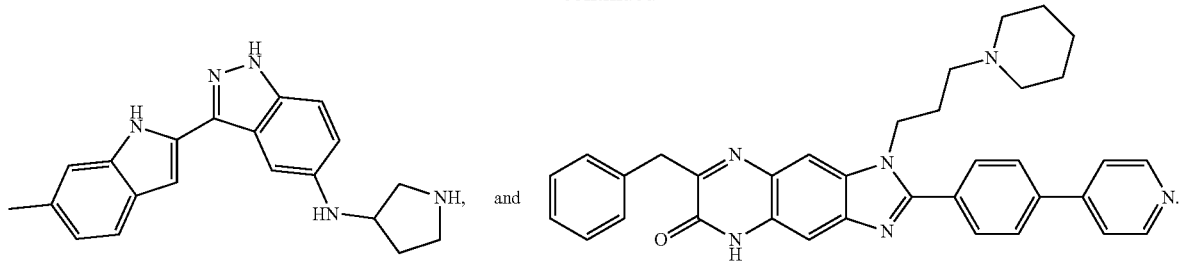 [SMILES: Cc1ccc2cc(-c3n[nH]c4ccc(NC5CCNC5)cc34)[nH]c2c1 ; O=c1[nH]c2cc3nc(-c4ccc(-c5ccncc5)cc4)n(CCCN4CCCCC4)c3cc2nc1Cc1ccccc1]

CDK4 Inhibitors

Disclosed herein, in certain embodiments, are methods of treating a B cell proliferative disorder in an individual in need thereof comprising administering to the individual a TEC inhibitor and a CDK4 inhibitor (e.g., a selective CDK4 inhibitor, e.g., palbociclib). In some instances, the TEC inhibitor is an ITK inhibitor or a BTK inhibitor. In some instances, the TEC inhibitor is an ITK inhibitor. In some instances, described herein are methods of treating a B cell proliferative disorder in an individual in need thereof comprising administering to the individual an ITK inhibitor and a CDK4 inhibitor (e.g., a selective CDK4 inhibitor, e.g., palbociclib).

In some instances, the TEC inhibitor is a BTK inhibitor. In some instances, the BTK inhibitor is a covalent BTK inhibitor. In some instances, disclosed herein are methods of treating a B cell proliferative disorder in an individual in need thereof comprising administering to the individual a covalent Btk inhibitor (e.g., an irreversible covalent Btk inhibitor) and a CDK4 inhibitor (e.g., a selective CDK4 inhibitor, e.g., palbociclib). In some embodiments, the covalent Btk inhibitor is PCI-32765 (Ibrutinib), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some instances, the BTK inhibitor is ibrutinib. In some instances, disclosed herein are methods of treating a B cell proliferative disorder in an individual in need thereof comprising administering to the individual ibrutinib and a CDK4 inhibitor (e.g., a selective CDK4 inhibitor, e.g., palbociclib). In some embodiments, the B cell proliferative disorder is refractory to the covalent Btk inhibitor (e.g., an irreversible covalent Btk inhibitor, e.g., ibrutinib). In some embodiments, the B cell proliferative disorder is relapsed. In some instances, the B cell proliferative disorder is an ibrutinib-resistant B cell proliferative disorder. In some instances, the B cell proliferative disorder is an ibrutinib-sensitive B cell proliferative disorder. In some embodiments, the B cell proliferative disorder is mantle cell lymphoma. In some embodiments, the MCL is an ibrutinib-resistant MCL. In some embodiments, the MCL is an ibrutinib-sensitive MCL.

As described above, cyclin-dependent kinase 4 (CDK4) is a Ser/Thr protein kinase. CDK4 is a catalytic subunit of a protein kinase complex that is important for cell cycle G1 phase progression. CDK4 (and CDK6) associate with D-type cyclins. The complex promotes cell cycle progression through $G_1$ by inactiviation of Rb protein. In some embodiments, inhibiting the activity of CDK4 inhibits cell cycle progression. In some embodiments, inhibiting the activity of CDK4 arrests the cell cycle in early $G_1$.

In some embodiments, the CDK4 inhibitor is a broad CDK inhibitor, or an inhibitor that targets a broad spectrum of CDK inhibitors. In some embodiments, the CDK4 inhibitor is a multiple target inhibitor, or an inhibitor that targets a CDK and an additional protein, such as for example kinases (e.g. VEGFR, PDGFR).

In some embodiments, the CDK4 inhibitor is a selective CDK4 inhibitor. In some embodiments, the CDK4 inhibitor is selective for CDK4 and CDK6. In some embodiments, the CDK4 inhibitor does not inhibit the activity of kinases other than CDK4 and/or CDK6. In some embodiments, the CDK4 inhibitor does not inhibit the activity of CDK2. In some embodiments, the CDK4 inhibitor is irreversible. In some embodiments, the CDK4 inhibitor is reversible.

In some embodiments, the CDK4 inhibitor is selected from: Palbociclib (also known as PD0332991), LY2835219, BAY 1000394 (also known as Roniciclib), CDK4 Inhibitor V (also known as 4-(((4-Hydroxy-5-propoxy-pyridin-2-yl-methyl)-amino)-methylene)-6-iodo-4H-isoquinoline-1,3-dione), Flavopiridol hydrochloride (also known as L868275, HMR-1275, or Alvocidib), Arcyriaflavin A, P276-00, CDK4 Inhibitor (also known as 2-Bromo-12,13-dihydro-5H-indolo[2,3-a]pyrrolo[3,4-c]carbazole-5,7(6H)-dione), AT7519, PHA-848125, NSC 625987 (also known as Cdk4 Inhibitor II), SU 9516, BMS-265246, indirubin-5-sulfonic acid sodium, Fascaplysin, NU6140 (also known as Cdk2 Inhibitor IV), Purvalanol A, Indirubin (also known as Isoindogotin), CINK4 (also known as Cdk4/6 Inhibitor IV), BS-181 HCl, 3-ATA, Oxindole I, Ryuvidine (also known as Cdk4 Inhibitor III), Purvalanol B (also known as NG 95), CAN508 (also known as Cdk9 Inhibitor II), R547, Hygrolidin, P1446A-05, G1T28-1, LEE011 (also known as 7-cyclopentyl-N,N-dimethyl-2-45-(piperazin-1-yl)pyridin-2-yl) amino)-7H-pyrrolo[2,3-d]pyrimidine-6-carboxamide), AG-024322 (also known as N-((5-(3-(4,6-difluoro-1H-benzo[d]imidazol-2-yl)-1H-indazol-4-yl)-4-methylpyridin-3-yl)methyl)ethanamine), SNS-032 (also known as BMS-387032 or N-[5-[[[5-(1,1-Dimethylethyl)-2-oxazolyl]methyl]thio]-2-thiazolyl]-4-piperidinecarboxamide), or ZK 304709 (also known as ZK-CDK or (Z)-3,3-dimethyl-2'-oxo-[2,3'-biindolinylidene]-5'-sulfonamide).

In some embodiments, the CDK4 inhibitor is palbociclib.

Combination Therapies

Disclosed herein, in certain embodiments, are methods of treating a B cell proliferative disorder in an individual in need thereof comprising administering to the individual a covalent TEC inhibitor and a CDK4 inhibitor (e.g., a selective CDK4 inhibitor, e.g., palbociclib). In some embodiments, the TEC inhibitor is a BTK, ITK, TEC, RLK, or BMX inhibitor. In some embodiments, the TEC inhibitor is a BTK inhibitor or an ITK inhibitor. In some embodiments, the TEC inhibitor is a BTK inhibitor. In some embodiments, the BTK inhibitor is a covalent BTK inhibitor. In some embodiments, the covalent Btk inhibitor is PCI-32765 (Ibrutinib), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the covalent BTK inhibitor is ibrutinib. In some embodiments, the B cell proliferative disorder is refractory to the covalent BTK inhibitor (e.g., an irreversible covalent Btk inhibitor, e.g., ibrutinib). In some embodiments, the B cell proliferative disorder is relapsed. In some instances, the B cell proliferative disorder is an ibrutinib-resistant B cell proliferative disorder. In some instances, the B cell proliferative disorder is an ibrutinib-sensitive B cell proliferative disorder. In some embodiments, the B cell proliferative disorder is mantle cell lymphoma. In some embodiments, the MCL is an ibrutinib-resistant MCL. In some embodiments, the MCL is an ibrutinib-sensitive MCL.

When a covalent BTK inhibitor (e.g., an irreversible covalent Btk inhibitor, e.g., ibrutinib) and a CDK4 inhibitor (e.g., a selective CDK4 inhibitor, e.g., palbociclib) are administered together, they do not have to be administered in the same pharmaceutical composition, and are optionally, because of different physical and chemical characteristics, administered by different routes. The initial administration is made, for example, according to established protocols, and then, based upon the observed effects, the dosage, modes of administration and times of administration are modified.

The compounds are optionally administered concurrently (e.g., simultaneously, essentially simultaneously or within the same treatment protocol) or sequentially, depending upon the nature of the disorder, the condition of the patient, and the actual choice of compounds used. The determination of the order of administration, and the number of repetitions of administration of each therapeutic agent during a treatment protocol, is based on an evaluation of the disease being treated and the condition of the patient. If administered sequentially, the attending physician will decide on the appropriate sequence of administering protein in combination with the biologically active agent(s).

In some embodiments, therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disorder being treated and so forth.

If the covalent Btk inhibitor (e.g., an irreversible covalent Btk inhibitor, e.g., ibrutinib) and the CDK4 inhibitor (e.g., a selective CDK4 inhibitor; e.g., palbociclib) are administered simultaneously, the multiple therapeutic agents are optionally provided in a single, unified form, or in multiple forms (by way of example only, either as a single pill or as two separate pills). In some embodiments, one of the therapeutic agents is given in multiple doses, or both are given as multiple doses. If not simultaneous, the timing between the multiple doses is from about more than zero weeks to less than about four weeks. In addition, the combination methods, compositions and formulations are not to be limited to the use of only two agents; the use of multiple therapeutic combinations is also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

In some embodiments, the pharmaceutical agents which make up the combination therapy disclosed herein are administered in a combined dosage form, or in separate dosage forms intended for substantially simultaneous administration. In some embodiments, the pharmaceutical agents that make up the combination therapy are administered sequentially, with either therapeutic compound being administered by a regimen calling for two-step administration. In some embodiments, the two-step administration regimen calls for sequential administration of the active agents or spaced-apart administration of the separate active agents. The time period between the multiple administration steps ranges from a few minutes to several hours, depending upon the properties of each pharmaceutical agent, such as potency, solubility, bioavailability, plasma half-life and kinetic profile of the pharmaceutical agent. In some embodiments, circadian variation of the target molecule concentration determines the optimal dose interval.

In some embodiments, the covalent Btk inhibitor (e.g., an irreversible covalent Btk inhibitor, e.g., ibrutinib) and the CDK4 inhibitor (e.g., a selective CDK4 inhibitor; e.g., palbociclib) are administered in a unified dosage form. In some embodiments, the covalent Btk inhibitor (e.g., an irreversible covalent Btk inhibitor, e.g., ibrutinib) and the CDK4 inhibitor (e.g., a selective CDK4 inhibitor; e.g., palbociclib) are administered in separate dosage forms. In some embodiments, the covalent Btk inhibitor (e.g., an irreversible covalent Btk inhibitor, e.g., ibrutinib) and the CDK4 inhibitor (e.g., a selective CDK4 inhibitor; e.g., palbociclib) are administered simultaneously or sequentially.

In some embodiments, the covalent Btk inhibitor (e.g., an irreversible covalent Btk inhibitor, e.g., ibrutinib) and the CDK4 inhibitor (e.g., a selective CDK4 inhibitor; e.g., palbociclib) are administered in combination with an additional therapeutic agent. The particular choice of compounds used will depend upon the diagnosis of the attending physicians and their judgment of the condition of the patient and the appropriate treatment protocol.

Additional Therapeutic Agents

In some embodiments, the additional therapeutic agent is a chemotherapeutic agent, a steroid, an immunotherapeutic agent, a targeted therapy, or a combination thereof. In some embodiments, the additional therapeutic agent is a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the additional therapeutic agent is an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In some embodiments, the additional therapeutic agent comprises an agent selected from: an inhibitor of LYN, SYK, JAK, PI3K, PLCγ, MAPK, MEK or NFκB.

In some embodiments, the additional therapeutic agent comprises an agent selected from: bendamustine, bortezomib, lenalidomide, idelalisib (GS-1101), vorinostat, ofatumumab, everolimus, panobinostat, temsirolimus, romidepsin, vorinostat, fludarabine, cyclophosphamide, mitoxantrone, pentostatine, prednisone, etopside, procarbazine, and thalidomide.

In some embodiments, the additional therapeutic agent is rituximab. In some embodiments, rituximab is further administered as a maintenance therapy.

In some embodiments the additional therapeutic agent is bendamustine. In some embodiments, bortezomib is administered in combination with rituximab.

In some embodiments, the additional therapeutic agent is bortezomib. In some embodiments, bendamustine is administered in combination with rituximab.

In some embodiments, the additional therapeutic agent is lenalidomide. In some embodiments, lenalidomide is administered in combination with rituximab.

In some embodiments, the additional therapeutic agent is a multi-agent therapeutic regimen. In some embodiments the additional therapeutic agent comprises the HyperCVAD regimen (cyclophosphamide, vincristine, doxorubicin, dexamethasone alternating with methotrexate and cytarabine). In some embodiments, the HyperCVAD regimen is administered in combination with rituximab.

In some embodiments the additional therapeutic agent comprises the R-CHOP regiment (rituximab, cyclophosphamide, doxorubicin, vincristine, and prednisone).

In some embodiments the additional therapeutic agent comprises bortezomib and rituximab.

In some embodiments the additional therapeutic agent comprises cladribine and rituximab.

In some embodiments the additional therapeutic agent comprises the FCR regiment (FCR (fludarabine, cyclophosphamide, rituximab).

In some embodiments the additional therapeutic agent comprises the FCMR regiment (fludarabine, cyclophosphamide, mitoxantrone, rituximab).

In some embodiments the additional therapeutic agent comprises the FMR regimen (fludarabine, mitoxantrone, rituximab).

In some embodiments the additional therapeutic agent comprises the PCR regimen (pentostatin, cyclophosphamide, rituximab).

In some embodiments the additional therapeutic agent comprises the PEPC regimen (prednisone, etoposide, procarbazine, cyclophosphamide).

In some embodiments the additional therapeutic agent comprises radioimmunotherapy with $^{90}$Y-ibritumomab tiuxetan or $^{131}$I-tositumomab.

In some embodiments, the additional therapeutic agent is an autologous stem cell transplant.

In some embodiments, the additional therapeutic agent is selected from: Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; Other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

In some embodiments, the additional therapeutic agent is selected from: interferons, interleukins, Tumor Necrosis Factors, Growth Factors, or the like.

In some embodiments, the additional therapeutic agent is selected from: ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-nl, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

In some embodiments, the additional therapeutic agent is selected from: Adalimumab, Alemtuzumab, Basiliximab, Bevacizumab, Cetuximab, Certolizumab pegol, Daclizumab, Eculizumab, Efalizumab, Gemtuzumab, Ibritumomab tiuxetan, Infliximab, Muromonab-CD3, Natalizumab, Panitumumab, Ranibizumab, Rituximab, Tositumomab, Trastuzumab, or the like, or a combination thereof.

In some embodiments, the additional therapeutic agent is selected from: Monoclonal Antibodies such as for example alemtuzumab, bevacizumab, catumaxomab, cetuximab, edrecolomab, gemtuzumab, ofatumumab, panitumumab, rituximab, trastuzumab; Immunosuppressants, eculizumab, efalizumab, muromab-CD3, natalizumab; TNF alpha Inhibitors such as for example adalimumab, afelimomab, certolizumab pegol, golimumab, infliximab; Interleukin Inhibitors, basiliximab, canakinumab, daclizumab, mepolizumab, tocilizumab, ustekinumab; Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

In some embodiments, the additional therapeutic agent is selected from: agents that affect the tumor micro-enviroment such as cellular signaling network (e.g. phosphatidylinositol 3-kinase (PI3K) signaling pathway, signaling from the B-cell receptor and the IgE receptor). In some embodiments, the additional therapeutic agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Arry-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, RO5185426, SAR103168, SCH 727965, SGI-1176, SGX523, SNS-314, TAK-593, TAK-901, TKI258, TLN-232, TTP607, XL147, XL228, XL281RO5126766, XL418, XL765.

In some embodiments, the additional therapeutic agent is selected from inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In some embodiments, the additional therapeutic agent is selected from: Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride;

estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-nl; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In some embodiments, the additional therapeutic agent is selected from: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the additional therapeutic agent is selected from: alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

In some embodiments, the additional therapeutic agent is selected from: nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

In some embodiments, the additional therapeutic agent is selected from: agents which act by arresting cells in the G2-M phases due to stabilized microtubules, e.g., Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Administration

Disclosed herein, in certain embodiments, are methods of treating a B cell proliferative disorder in an individual in need thereof comprising administering to the individual a TEC inhibitor (e.g., an ITK inhibitor or a BTK inhibitor) and a CDK4 inhibitor (e.g., a selective CDK4 inhibitor, e.g., palbociclib). Disclosed herein, in certain embodiments, are methods of treating a B cell proliferative disorder in an individual in need thereof comprising administering to the individual a covalent Btk inhibitor (e.g., an irreversible covalent Btk inhibitor) and a CDK4 inhibitor (e.g., a selective CDK4 inhibitor, e.g., palbociclib). In some embodiments, the covalent Btk inhibitor is PCI-32765 (Ibrutinib), PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the covalent Btk inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, described herein are methods of treating a B cell proliferative disorder in an individual in need thereof comprising administering to the individual ibrutinib and a CDK4 inhibitor (e.g., a selective CDK4 inhibitor, e.g., palbociclib). In some embodiments, the CDK4 inhibitor is palbociclib. In some embodiments, the B cell proliferative disorder is refractory to the covalent Btk inhibitor (e.g., an irreversible covalent Btk inhibitor, e.g., ibrutinib). In some embodiments, the B cell proliferative disorder is relapsed. In some instances, the B cell proliferative disorder is an ibrutinib-resistant B cell proliferative disorder. In some instances, the B cell proliferative disorder is an ibrutinib-sensitive B cell proliferative disorder. In some embodiments, the B cell proliferative disorder is mantle cell lymphoma. In some embodiments, the MCL is an ibrutinib-resistant MCL. In some embodiments, the MCL is an ibrutinib-sensitive MCL.

The covalent Btk inhibitor (e.g., an irreversible covalent Btk inhibitor, e.g., ibrutinib) and the CDK4 inhibitor (e.g., a selective CDK4 inhibitor, e.g., palbociclib) are administered before, during or after the development of a B cell proliferative disorder (e.g., mantle cell lymphoma). In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered before development of a B cell proliferative disorders (e.g., mantle cell lymphoma) which is refractory to Ibrutinib. In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered after development of a B cell proliferative disorders (e.g., mantle cell lymphoma) which is refractory to Ibrutinib. In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are used as a prophylactic and is administered continuously to subjects with a propensity to develop a B cell proliferative disorder (e.g., MCL). In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered to an individual during or as soon as possible after the development of a B cell proliferative disorder (e.g., MCL).

In some embodiments, the initial administration of the covalent Btk inhibitor (e.g., an irreversible covalent Btk inhibitor, e.g., ibrutinib) and the CDK4 inhibitor (e.g., a selective CDK4 inhibitor, e.g., palbociclib) are via any route practical, such as, for example, an intravenous injection, a bolus injection, infusion over 5 minutes to about 5 hours, a pill, a capsule, transdermal patch, buccal delivery, and the like, or combination thereof.

The covalent Btk inhibitor (e.g., an irreversible covalent Btk inhibitor, e.g., ibrutinib) and the CDK4 inhibitor (e.g., a selective CDK4 inhibitor, e.g., palbociclib) should be administered as soon as is practicable after the onset of a disorder is detected or suspected, and for a length of time necessary for the treatment of the disease, such as, for example, from about 1 month to about 3 months, or continuously throughout the individual's life. The length of treatment can vary for each subject, and the length can be determined using the known criteria. In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered for at least 2 weeks, between about 1 month to about 5 years, or from about 1 month to about 3 years. In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered throughout the individual's life.

Therapeutically effective amounts will depend on the severity and course of the disorder, previous therapy, the patient's health status, weight, and response to the drugs, and the judgment of the treating physician. Prophylactically effective amounts depend on the patient's state of health, weight, the severity and course of the disease, previous therapy, response to the drugs, and the judgment of the treating physician.

In some embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered to the patient on a regular basis, e.g., three times a day, two times a day, once a day, every other day or every 3 days. In other embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the covalent Btk inhibitor (e.g., an irreversible covalent Btk inhibitor, e.g., ibrutinib) and the CDK4 inhibitor (e.g., a selective CDK4 inhibitor, e.g., palbociclib) are administered only when the patient exhibits a particular symptom, e.g., the onset of pain, or the onset of a fever, or the onset of an inflammation, or the onset of a skin disorder. Dosing schedules of each compound may depend on the other or may be independent of the other.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance regimen is administered if necessary. Subsequently, the dosage or the frequency of administration, or both, of the covalent Btk inhibitor (e.g., an irreversible covalent Btk inhibitor, e.g., ibrutinib) and the CDK4 inhibitor (e.g., a selective CDK4 inhibitor, e.g., palbociclib) can be reduced, as a function of the symptoms, to a level at which the individual's improved condition is retained. Individuals can, however, require intermittent treatment on a long-term basis upon any recurrence of symptoms.

The amount of the covalent Btk inhibitor (e.g., an irreversible covalent Btk inhibitor, e.g., ibrutinib) and the CDK4 inhibitor (e.g., a selective CDK4 inhibitor, e.g., palbociclib) are will vary depending upon factors such as the particular compound, disorder and its severity, the identity (e.g., weight) of the subject or host in need of treatment, and is determined according to the particular circumstances surrounding the case, including, e.g., the specific agents being administered, the routes of administration, and the subject or host being treated. In general, however, doses employed for adult human treatment will typically be in the range of 0.02-5000 mg per day, or from about 1-1500 mg per day. The desired dose may be presented in a single dose or as divided doses administered simultaneously (or over a short period of time) or at appropriate intervals, for example as two, three, four or more sub-doses per day.

In some embodiments, the therapeutic amount of the covalent Btk inhibitor (e.g., an irreversible covalent Btk inhibitor, e.g., ibrutinib) is from 100 mg/day up to, and including, 2000 mg/day. In some embodiments, the amount of the covalent Btk inhibitor (e.g., an irreversible covalent Btk inhibitor, e.g., ibrutinib) is from 140 mg/day up to, and including, 840 mg/day. In some embodiments, the amount of the covalent Btk inhibitor (e.g., an irreversible covalent Btk inhibitor, e.g., ibrutinib) is from 420 mg/day up to, and including, 840 mg/day. In some embodiments, the amount of the covalent Btk inhibitor (e.g., an irreversible covalent Btk inhibitor, e.g., ibrutinib) is about 140 mg/day. In some embodiments, the amount of the covalent Btk inhibitor (e.g., an irreversible covalent Btk inhibitor, e.g., ibrutinib) is about 280 mg/day. In some embodiments, the amount of the covalent Btk inhibitor (e.g., an irreversible covalent Btk inhibitor, e.g., ibrutinib) is about 420 mg/day. In some embodiments, the amount of the covalent Btk inhibitor (e.g., an irreversible covalent Btk inhibitor, e.g., ibrutinib) is about 560 mg/day. In some embodiments, the amount of the covalent Btk inhibitor (e.g., an irreversible covalent Btk inhibitor, e.g., ibrutinib) is about 700 mg/day. In some embodiments, the amount of the covalent Btk inhibitor (e.g., an irreversible covalent Btk inhibitor, e.g., ibrutinib) is about 840 mg/day. In some embodiments, the amount of the covalent Btk inhibitor (e.g., an irreversible covalent Btk inhibitor, e.g., ibrutinib) is about 980 mg/day. In some embodiments, the amount of the covalent Btk inhibitor (e.g., an irreversible covalent Btk inhibitor, e.g., ibrutinib) is about 1120 mg/day. In some embodiments, the amount of the covalent Btk inhibitor (e.g., an irreversible covalent Btk inhibitor, e.g., ibrutinib) is about 1260 mg/day. In some embodiments, the amount of the covalent Btk inhibitor (e.g., an irreversible covalent Btk inhibitor, e.g., ibrutinib) is about 1400 mg/day.

In some embodiments, the dosage of the covalent Btk inhibitor (e.g., an irreversible covalent Btk inhibitor, e.g., ibrutinib) is escalated over time. In some embodiments, the dosage of the covalent Btk inhibitor (e.g., an irreversible covalent Btk inhibitor, e.g., ibrutinib) is escalated from at or about 1.25 mg/kg/day to at or about 12.5 mg/kg/day over a predetermined period of time. In some embodiments the predetermined period of time is over 1 month, over 2 months, over 3 months, over 4 months, over 5 months, over 6 months, over 7 months, over 8 months, over 9 months, over 10 months, over 11 months, over 12 months, over 18 months, over 24 months or longer.

The covalent Btk inhibitor (e.g., an irreversible covalent Btk inhibitor, e.g., ibrutinib) and the CDK4 inhibitor (e.g., a selective CDK4 inhibitor, e.g., palbociclib) may be formulated into unit dosage forms suitable for single administration of precise dosages. In unit dosage form, the formulation is divided into unit doses containing appropriate quantities of one or both compounds. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

It is understood that a medical professional will determine the dosage regimen in accordance with a variety of factors. These factors include the solid tumor from which the subject suffers, the degree of metastasis, as well as the age, weight, sex, diet, and medical condition of the subject.

Pharmaceutical Compositions/Formulations

Disclosed herein, in certain embodiments, are compositions for treating a B cell proliferative disorder in an individual in need thereof comprising a TEC inhibitor (e.g., an ITK inhibitor, a BTK inhibitor, e.g. a covalent BTK inhibitor,) and/or a CDK4 inhibitor (e.g., a selective CDK4 inhibitor, e.g., palbociclib). Disclosed herein, in certain embodiments, are compositions for treating a B cell proliferative disorder in an individual in need thereof comprising a covalent Btk inhibitor (e.g., an irreversible covalent BTK inhibitor, e.g., ibrutinib) and/or a CDK4 inhibitor (e.g., a selective CDK4 inhibitor, e.g., palbociclib). In some embodiments, the B cell proliferative disorder is refractory to the covalent BTK inhibitor (e.g., an irreversible covalent BTK inhibitor, e.g., ibrutinib). In some embodiments, the B cell proliferative disorder is relapsed. In some embodiments, the B cell proliferative disorder is mantle cell lymphoma.

In some embodiments, the covalent BTK inhibitor is a compound of Formula (A). In some embodiments, the covalent Btk inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib). In some embodiments, the CDK4 inhibitor is palbociclib.

Pharmaceutical compositions of covalent Btk inhibitors (e.g., an irreversible covalent Btk inhibitor, e.g., ibrutinib) and/or CDK4 inhibitors are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A pharmaceutical composition, as used herein, refers to a mixture of a covalent Btk inhibitor (e.g., an irreversible covalent Btk inhibitor, e.g., ibrutinib) and/or a CDK4 inhibitor (e.g., a selective CDK4 inhibitor; e.g., palbociclib) with other chemical components, such as carriers, stabilizers, diluents, dispersing agents, suspending agents, thickening agents, and/or excipients.

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein are administered by any suitable administration route, including but not limited to, oral, parenteral (e.g., intravenous, subcutaneous, intramuscular), intranasal, buccal, topical, rectal, or transdermal administration routes.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for IV administration).

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per mL, dL, or L of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. In some embodiments, the composition is formulated for administration in a combined dosage form. In some embodiments, the composition is formulated for administration in a separate dosage forms. As used herein, the term "subject" is used to mean an animal, preferably a mammal, including a human or non-human. The terms "individual(s)", "subject(s)" and "patient(s)" are used interchangeably herein, and mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

Moreover, the pharmaceutical compositions described herein, which include ibrutinib and/or an anticancer agent can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of ibrutinib and/or an anticancer agent, with one or more pharmaceutical excipients to form a bulk blend composition. When referring to these bulk blend compositions as homogeneous, it is meant that the particles of ibrutinib and/or an anticancer agent, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of ibrutinib and/or an anticancer agent. In another embodiment, some or all of the particles of ibrutinib and/or an anticancer agent, are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of ibrutinib and/or an anticancer agent, from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of ibrutinib or the second agent, from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of ibrutinib or the second agent, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of ibrutinib and/or an anticancer agent, and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with ibrutinib and/or an anticancer agent, which sufficiently isolate the compound of any of ibrutinib or an anticancer agent, from other non-compatible excipients. Materials compatible with compounds of any of ibrutinib or an anticancer agent, are those that delay the release of the compounds of any of ibrutinib or an anticancer agent, in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of ibrutinib or an anticancer agent may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/ spheronization, coacervation, or nanoparticle coating may also be used.

In one embodiment, the particles of compounds of any of ibrutinib or an anticancer agent are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of the compounds of any of ibrutinib and/or an anticancer agent are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of ibrutinib and/or an anticancer agent, described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include ibrutinib and/or an anticancer agent, are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

In some embodiments, pharmaceutical formulations are provided that include particles of ibrutinib and/or an anticancer agent, described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, $2^{nd}$ Ed., pp. 754-757 (2002). In addition the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as) Plasdone®, and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations that include ibrutinib and/or An anticancer agent, which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation described herein may be in a form as an aerosol, a mist or a powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with ibrutinib and/or An anticancer agent, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of ibrutinib and An anticancer agent; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of ibrutinib and An anticancer agent. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of ibrutinib and/or An anticancer agent, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In some embodiments, the pharmaceutical compositions are formulated such that the amount of the covalent Btk inhibitor (e.g., an irreversible covalent Btk inhibitor, e.g., ibrutinib) in each unit dosage form is about 140 mg per.

Diagnosis Methods

Methods for determining the expression or presence of biomarkers described supra are well known in the art, and can be measured, for example, by flow cytometry, immunohistochemistry, Western Blot, immunoprecipitation, magnetic bead selection, and quantification of cells expressing either of these cell surface markers. Biomarker RNA expression levels could be measured by RT-PCR, Qt-PCR, microarray, Northern blot, or other similar technologies.

By "detecting expression" or detecting "expression levels" is intended for determining the expression level or presence of a biomarker protein or gene in the biological sample. Thus, "detecting expression" encompasses instances where a biomarker is determined not to be expressed, not to be detectably expressed, expressed at a low level, expressed at a normal level, or overexpressed.

In some embodiments, the expression or presence of a biomarker described herein is determined at a nucleic acid level, using, for example, immunohistochemistry techniques or nucleic acid-based techniques such as in situ hybridization and RT-PCR. In one embodiments, the expression or presence of one or more biomarkers is carried out by a means for nucleic acid amplification, a means for nucleic acid sequencing, a means utilizing a nucleic acid microarray (DNA and RNA), or a means for in situ hybridization using specifically labeled probes.

In other embodiments, the determining the expression or presence of a biomarker is carried out through gel electrophoresis. In one embodiment, the determination is carried out through transfer to a membrane and hybridization with a specific probe.

In other embodiments, the determining the expression or presence of a biomarker is carried out by a diagnostic imaging technique.

In still other embodiments, the determining the expression or presence of a biomarker is carried out by a detectable solid substrate. In one embodiment, the detectable solid substrate is paramagnetic nanoparticles functionalized with antibodies.

In some embodiments, the expression or presence of a biomarker is at an RNA (e.g. mRNA) level. In some embodiments, techniques that detect RNA (e.g. mRNA) level include, but are not limited to, Southern or Northern analyses, polymerase chain reaction analyses and probe arrays.

One method for the detection of mRNA levels involves contacting the isolated mRNA with a nucleic acid molecule (probe) that hybridize to the mRNA encoded by the gene being detected. The nucleic acid probe comprises of, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker described herein. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan readily adapts known mRNA detection methods for use in detecting the level of mRNA encoding the biomarkers or other proteins of interest.

An alternative method for determining the level of an mRNA of interest in a sample involves the process of nucleic acid amplification, e.g., by RT-PCR (see, for example, U.S. Pat. No. 4,683,202), ligase chain reaction (Barany (1991) Proc. Natl. Acad. Sci. USA 88:189 193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression is assessed by quantitative fluorogenic RT-PCR (i.e., the TaqMan0 System).

Expression levels of an RNA of interest are monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression also comprises using nucleic acid probes in solution.

In one embodiment of the invention, microarrays are used to determine expression or presence of one or more biomarkers. Nucleic acid microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. In some embodiments, an array is fabricated on a surface of virtually any shape or even a multiplicity of surfaces. In some embodiments, an array is a planar array surface. In some embodiments, arrays include peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. In some embodiments, arrays are packaged in such a manner as to allow for diagnostics or other manipulation of an all-inclusive device.

In some embodiments, the expression or presence of a biomarker described herein is determined at a protein level, using, for example, antibodies that are directed against specific biomarker proteins. These antibodies are used in various methods such as Western blot, ELISA, multiplexing technologies, immunoprecipitation, or immunohistochemistry techniques. In some embodiments, detection of biomarkers is accomplished by ELISA. In some embodiments, detection of biomarkers is accomplished by electrochemiluminescence (ECL).

Any means for specifically identifying and quantifying a biomarker in the biological sample is contemplated. Thus, in some embodiments, expression level of a biomarker protein of interest in a biological sample is detected by means of a binding protein capable of interacting specifically with that biomarker protein or a biologically active variant thereof. In some embodiments, labeled antibodies, binding portions thereof, or other binding partners are used. The word "label" when used herein refers to a detectable compound or composition that is conjugated directly or indirectly to the antibody so as to generate a "labeled" antibody. In some embodiments, the label is detectable by itself (e.g., radioisotope labels or fluorescent labels) or, in the case of an enzymatic label, catalyzes chemical alteration of a substrate compound or composition that is detectable.

The antibodies for detection of a biomarker protein are either monoclonal or polyclonal in origin, or are synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols are found in numerous texts in the art (see, for example, Ausubel et al., eds. (1995) Current Protocols in Molecular Biology) (Greene Publishing and Wiley-Interscience, NY)); Coligan et al., eds. (1994) Current Protocols in Immunology (John Wiley & Sons, Inc., New York, N.Y.).

The choice of marker used to label the antibodies will vary depending upon the application. However, the choice of the marker is readily determinable to one skilled in the art. These labeled antibodies are used in immunoassays as well as in histological applications to detect the presence of any biomarker or protein of interest. The labeled antibodies are either polyclonal or monoclonal. Further, the antibodies for use in detecting a protein of interest are labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that serve as detectable labels include, for example, 1-131, 1-123, 1-125, Y-90, Re-188, Re-186, At-211, Cu-67, Bi-212, and Pd-109. Examples of enzymes that serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies are conjugated to these labels by methods known in the art. For example, enzymes and chromophoric molecules are conjugated to the antibodies by means of coupling agents, such as dialdehydes, carbodiimides, dimaleimides, and the like. Alternatively, conjugation occurs through a ligand-receptor pair. Examples of suitable ligand-receptor pairs are biotin-avidin or biotin-streptavidin, and antibody-antigen.

In certain embodiments, expression or presence of one or more biomarkers or other proteins of interest within a biological sample is determined by radioimmunoassays or enzyme-linked immunoassays (ELISAs), competitive binding enzyme-linked immunoassays, dot blot (see, for example, Promega Protocols and Applications Guide, Promega Corporation (1991), Western blot (see, for example, Sambrook et al. (1989) Molecular Cloning, A Laboratory Manual, Vol. 3, Chapter 18 (Cold Spring Harbor Laboratory Press, Plainview, N.Y.), chromatography such as high performance liquid chromatography (HPLC), or other assays known in the art. Thus, the detection assays involve steps such as, but not limited to, immunoblotting, immunodiffusion, immunoelectrophoresis, or immunoprecipitation.

Samples

In some embodiments, the sample for use in the methods is obtained from cells of a B cell proliferative disorder cell line. In some embodiments, the sample is obtained from cells of an acute lymphoblastic leukemia (ALL), acute myelogenous leukemia (AML), chronic myelogenous leukemia (CML), acute monocytic leukemia (AMoL), chronic lymphocytic leukemia (CLL), high risk CLL, small lymphocytic lymphoma (SLL), high risk SLL, follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis cell line. In some embodiments, the sample is obtained from cells of a MCL cell line.

In some embodiments, the sample is a MCL cell or population of MCL cells. In some embodiments, the MCL cell line is Jeko (JeKo-1), MAVER-1, MINO, SP-53, Granta 519, or REC-1. In some embodiments, the sample is chicken DT40 lymphoid cells deficient in BTK. In some embodiments, the MCL cell line that is sensitive to treatment with a BTK inhibitor includes Jeko (JeKo-1), MAVER-1, and MINO.

In some embodiments, the sample for use in the methods is from any tissue or fluid from a patient. Samples include, but are not limited, to whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In particular embodiments, the sample is a blood serum sample. In particular embodiments, the sample is from a fluid or tissue that is part of, or associated with, the lymphatic system or circulatory system. In some embodiments, the sample is a blood sample that is a venous, arterial, peripheral, tissue, cord blood sample. In some embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

In some embodiments, the samples are obtained from the individual by any suitable means of obtaining the sample using well-known and routine clinical methods. Procedures for obtaining fluid samples from an individual are well known. For example, procedures for drawing and processing whole blood and lymph are well-known and can be employed to obtain a sample for use in the methods provided. Typically, for collection of a blood sample, an anticoagulation agent (e.g., EDTA, or citrate and heparin or CPD (citrate, phosphate, dextrose) or comparable substances) is added to the sample to prevent coagulation of the blood. In some examples, the blood sample is collected in a collection tube that contains an amount of EDTA to prevent coagulation of the blood sample.

In some embodiments, the collection of a sample from the individual is performed at regular intervals, such as, for example, one day, two days, three days, four days, five days, six days, one week, two weeks, weeks, four weeks, one month, two months, three months, four months, five months, six months, one year, daily, weekly, bimonthly, quarterly, biyearly or yearly.

In some embodiments, the collection of a sample is performed at a predetermined time or at regular intervals relative to treatment with a combination of a TEC inhibitor and a CDK4 inhibitor. In some embodiments, the TEC inhibitor is a BTK inhibitor, an ITK inhibitor, a TEC inhibitor, a RLK inhibitor, or a BMX inhibitor. In some embodiments, the TEC inhibitor is an ITK inhibitor. In some embodiments, the TEC inhibitor is a BTK inhibitor. In some embodiments, the BTK inhibitor is a covalent BTK inhibitor.

In some embodiments, the collection of a sample is performed at a predetermined time or at regular intervals relative to treatment with a combination of an ITK inhibitor and a CDK4 inhibitor. For example, a sample is collected from a patient at a predetermined time or at regular intervals prior to, during, or following treatment or between successive treatments with a combination of an ITK inhibitor and a CDK4 inhibitor. In particular examples, a sample is obtained from a patient prior to administration of a combination of an ITK inhibitor and a CDK4 inhibitor, and then again at regular intervals after treatment with the combination of the ITK inhibitor and the CDK4 inhibitor has been affected. In some embodiments, the patient is administered a combination of an ITK inhibitor and a CDK4 inhibitor and one or more additional therapeutic agents. In some embodiments, the ITK inhibitor is an irreversible ITK inhibitor. In some embodiments, the ITK inhibitor is a reversible ITK inhibitor. In some embodiments, the CDK4 inhibitor is selected from Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is Palbociclib.

In some embodiments, the collection of a sample is performed at a predetermined time or at regular intervals relative to treatment with a combination of a BTK inhibitor and a CDK4 inhibitor. For example, a sample is collected from a patient at a predetermined time or at regular intervals prior to, during, or following treatment or between successive treatments with a combination of a BTK inhibitor and a CDK4 inhibitor. In particular examples, a sample is obtained from a patient prior to administration of a combination of a BTK inhibitor and a CDK4 inhibitor, and then again at regular intervals after treatment with the combination of the BTK inhibitor and the CDK4 inhibitor has been affected. In some embodiments, the patient is administered a combination of a BTK inhibitor and a CDK4 inhibitor and one or more additional therapeutic agents. In some embodiments, the BTK inhibitor is an irreversible BTK inhibitor. In some embodiments, the BTK inhibitor is a reversible BTK inhibitor. In some embodiments, the BTK inhibitor is a covalent BTK inhibitor. In some embodiments, the covalent Btk inhibitor is PCI-32765 (Ibrutinib), PCI-45292, PCI- 45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc). In some embodiments, the covalent BTK inhibitor is ibrutinib. In some embodiments, the CDK4 inhibitor is selected from Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is Palbociclib.

In some embodiments, the collection of a sample is performed at a predetermined time or at regular intervals relative to treatment with a combination of ibrutinib and a CDK4 inhibitor. For example, a sample is collected from a patient at a predetermined time or at regular intervals prior to, during, or following treatment or between successive treatments with a combination of ibrutinib and a CDK4 inhibitor. In particular examples, a sample is obtained from a patient prior to administration of a combination of ibrutinib and a CDK4 inhibitor, and then again at regular intervals after treatment with the combination of ibrutinib and the CDK4 inhibitor has been affected. In some embodiments, the patient is administered a combination of ibrutinib and a CDK4 inhibitor and one or more additional therapeutic agents. In some embodiments, the CDK4 inhibitor is selected from Palbociclib, Hygrolidin, P276-00, Dinaciclib, AT7519, Flavopiridol hydrochloride, indirubin-5-sulfonic acid sodium, Fascaplysin, NSC 625987, Purvalanol A, Purvalanol B, Oxindole I, R547, BAY 1000394 LY2835219, CDK Inhibitor V, CDK Inhibitor, Arcyriaflavin A, PHA-848125, BMS-265246, Fascaplysin, NU6140, Indirubin, CINK4, BS-181 HCl, 3-ATA, Ryuvidine, CAN508, P1446A-05, G1T28-1, LEE011, AG-024322, SNS-032, ZK 304709, and SU 9516. In some embodiments, the CDK4 inhibitor is Palbociclib.

Kits/Articles of Manufacture

Described herein are kits for treating a B cell proliferative disorder, in an individual in need thereof comprising a therapeutically-effective amount of a covalent Btk inhibitor (e.g., an irreversible covalent Btk inhibitor, e.g., ibrutinib) and a therapeutically-effective amount of a CDK4 inhibitor (e.g., a selective CDK4 inhibitor, e.g., palbociclib). In some embodiments, the B cell proliferative disorder is refractory to the covalent Btk inhibitor (e.g., an irreversible covalent Btk inhibitor, e.g., ibrutinib). In some embodiments, the B cell proliferative disorder is relapsed. In some embodiments, the B cell proliferative disorder is mantle cell lymphoma.

For use in the therapeutic applications described herein, kits and articles of manufacture are also described herein. In some embodiments, such kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder that benefit by inhibition of Btk, or in which Btk is a mediator or contributor to the symptoms or cause.

The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

In some embodiments, a label is on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a pharmaceutical composition comprising the covalent Btk inhibitor (e.g., an irreversible covalent Btk inhibitor, e.g., ibrutinib) is presented in a pack or dispenser device which can contain one or more unit dosage forms. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.

Example 1

Primary Cells Isolation

Mantle cell lymphoma (MCL) biopsies were obtained from patients at the New York-Presbyterian Hospital after informed consent as part of a study approved by the Institutional Review Board. Primary MCL cells were purified using MACS CD19 MicroBeads (Miltenyi Biotec). The percentage of MCL tumor cells (CD19+, CD5+) was determined to be >90% by flow cytometry. B cells from healthy volunteers were isolated from peripheral blood (PBC)s using the same protocol.

Whole Transcriptome Sequencing (WTS)

For each experimental condition, 100 ng of high quality total RNA (RIN>0.8 on the Agilent BioAnalyzer 2100) was isolated using the RNAEasy kit according to the manufacturer's instructions (QIAGEN). All RNAs were converted to cDNA, isolated with magnetic beads from the TruSeq mRNA prep kit (v2), and then ligated to Illumina adapters, as per the standard TruSeq Illumina protocol. Using these multi-plexed cDNA libraries, we generated clusters on the Illumina cBot station and paired-end sequenced each sample to 50×50 bp on the Illumina HiSeq2000 at the Weill Cornell Medical College (WCMC) Genomics Core. Cluster generation, sequencing, and processing of the images were done using the Real-Time Analysis (RTA) software on the HiSeq2000 and post-processing with CASAVA (v.1.8.2). To optimize library preparation we used a TACON high-throughput RNA prep-station. Raw data were filtered for high median quality (Q-value>20) and then sent to Cornell's High Performance Computing (HPC) cluster, to be run through our RNA-seq analysis pipeline. The RNA-seq data presented in this study, which include libraries from serial biopsies of MCL tumors before Ibrutinib treatment (p_Ib1, p_Ib2, p_Ib3) and after Ibrutinib relapse (r_IbBM, r_IbSP) and PBCs from 3 healthy volunteers have been deposited in the Gene Expression Omnibus (GEO).

Whole Exome Sequencing (WES)

DNA were isolated from purified MCL cells of 5 serial biopsies before Ibrutinib treatment (p_Ib1, p_Ib2, p_Ib3) and after Ibrutinib relapse (r_IbBM, r_IbSP) and a cheek swab (CS) of Pt7, captured with Nextera Rapid Exome Capture Kit (62 MB) and libraries were created according to the manufacturer's protocol. Briefly, purified DNA was fragmented and a sequencing library was created with the Illumina TruSeq (v3) DNA Preparation kits (FC-121-1031). Following isothermal cluster generation (PE-401-3001) and 75×75 paired-end (PE) sequencing on the HiSeq2500 (FC-401-3001), the samples underwent primary analysis with the Illumina base calling and primary analysis software (HCS 1.4, CASAVA 1.8.2, and RTA 1.2).

Immunoblotting

Proteins were analyzed with the following antibodies: CDK4 (#2906), cyclinD1 (#2926), AKT (#9272), p-AKT-S473 (#9271), p-AKT-T308 (#4056), p-BTK-Y223 (#5082), p-PLCg2-Y759 (#3874), PLCg2 (#3872), Cyclin B (#4135), CDK1 (#9112), c-Myc (#9402 N-term) (all from Cell Signaling Technology); actin (sc-1615) Cyclin A (sc-751) and p27 (sc-528) from Santa Cruz Biotechnology, BTK (Y440) from Abcam.

shRNA Knockdown

Cells were infected with lentiviruses containing shRNA specific for PIK3IP1 (#1: TRCN0000135363; #2: TRCN0000135429), or LacZ (TRCN0000072229) (The RNAi Consortium at Broad Institute, Cambridge, Mass.). Knockdown was confirmed by quantitative RT-PCR at 60-72 h post-transduction.

Cell Lines

The MCL cell lines used in this study were: JEKO-1 obtained from DSMZ (Braunschweig, Germany); MAVER-1 and MINO from ATCC (Manassas, Va.); and SP53 by Dr. Jiangao Tao (Moffit Cancer Center, Tampa Fla.). The MCL cells were cultured in the presence of PD 0332991 (Sellek Chemical) or Ibrutinib (Pharmacyclics), or both, at concentrations and for times indicated. PD 0332991 was added daily (0.25 µM) to maintain prolonged G1 arrest (pG1).

Immunohistochemistry

Immunohistochemistry was done on 4-µm sections of paraffin-embedded bone marrow, lymph node or spleen tissues using a TechMate500 BioTek automated immunostainer and reagents (Ventana Medical Systems, Inc., Tucson, Ariz.) according to manufacturer's specifications. Pax 5 was detected using an anti-Pax 5 (mAb; Serotec, Oxford, England) and a red chromogen. The nuclei were visualized by counterstaining with hematoxylin (blue). Simultaneous expression of other proteins was detected with mAbs to Ki67 (Zymed, San Francisco, Calif.); cyclin D1, Rb; and polyclonal rabbit antibodies to phospho-Ser807/811 and phospho-Ser780 of human Rb (Cell Signaling).

As a control for immunoglobulin synthesis, serial sections were stained with rabbit antibodies for IgM, IgD, IgG, IgA, Igk, and Igl (DakoCytomation, Carpinteria, Calif.). The frequency of MCL (Pax 5+) cells expressing a specific protein was scored by image analysis, using the Leica Biosystems, Ariol SL50 system. Ps<0.05 were considered statistically significant.

Mutation Validation by Sanger Sequencing

Sanger sequencing was conducted in serial biopsies of Pt7 taken immediately before Ibrutinib treatment (p_Ib3) and after Ibrutinib relapse (r_IbBM, r_IbSP), and in cells from the MCL MINO cell line. The primers used for the sequencing (Sigma-Aldrich) have the following sequence: 5'-AGT-TGTATGGCGTCTGCACCAA-3' (forward) and 5'-AG-GTCTCGGTGAAGGAACTGCT-3' (reverse). Sanger sequencing was performed at the Institute of Biotechnology of Cornell University.

Computational Analysis of the WES and WTS Data:

For the computational analysis of the somatic SNPs both present in WES and WTS datasets, we developed our own scripts in Ruby and Awk. We used ONCOTATOR (http://www.broadinstitute.org/oncotator/) for their corresponding annotation and we further characterized the relevant mutations using SIFT, POLYPHEN2 and PROVEAN. For the Copy Number Variations analysis, we correspondingly developed our own Python scripts.

Quality Check of WES Data.

The freely available software FASTQC (http://www.bioinformatics.bbsrc.ac.uk/projects/fastqc) was used to make a quality check of the WES data. While the per base Quality scores of the 75 bps reads were above 30 on average, it was observed that there were non random fluctuations in the per base content of the reads in the first 15 bases of the 5' end (due to the use of primers in the exome capture technique). For this reason, it was decided to create an alternative and rather conservative WES data set. For comparison, it was performed trimming of 15 bases at the 5' end and 2 bases at the 3' end. For the trimming, the freely available software FASTX-Toolkit (http://hannonlab.cshl.edu/fastx_toolkit/) was used.

Quality Check of WTS Data.

The freely available software FASTQC was also used to make a quality check of the WTS data. While the per base Quality scores of the 50 bps reads were above 30 on average, it was also observed there were non-random fluctuations in the per base content of the reads in the first 12 bases of the 5' end (due to the use of primers in the RNA-seq process). It was then also decided to create an alternative and rather conservative WTS data set, for comparison, where the trimming of 12 bases at the 5' end and 2 bases at the 3' end were preformed. The trimming was done simultaneously with the alignment using STAR.

WES Data Alignment.

The corresponding raw fastq files from DNA-seq (from both untrimmed and trimmed sets) were aligned to the GRCh37 hg19 human genome. BWA was used, which in our experience outperforms other common aligners for WES data.

WES Data Variant Calling.

The subsequent variant calling of the aligned data was done with the latest GATK version 2.5 with base quality score recalibration, indel realignment, duplicate removal, and performing SNP and INDEL discovery and genotyping across all the 5 samples simultaneously, using standard hard filtering parameters and variant quality score recalibration.

WTS Data Alignment.

The raw fastq files from RNA-seq were aligned also to the GRCh37 hg19 human genome. We aligned the data using two different aligners: BWA, for the untrimmed data, and STAR, for the trimmed data. The first one was performed within the pipeline of the commercially available software GeneSifter (Geospiza) and the second one as part of our own pipeline.

WTS Data Variant Calling.

The variants of the un-trimmed aligned data (BWA) were called, within the pipeline of GeneSifter, with GATK version 2.2. For the trimmed aligned data (STAR) we used Samtools to call the variants. The reason why in the latter case we did not use GATK was that the per base map quality scores given by STAR are in a different scale as required from GATK. While these scores could be fixed to fulfill GATK's requirements, we would have introduced bias and therefore loss precision in the posterior variant calling process.

Analysis and Filtering.

From the recalibrated variant calling file (vcf), we kept only those variants that fulfilled the following criteria:

The variants in the tumor samples should not be in the control samples (PBCs).

The variants in the tumor samples should have Read Depth different than 0 in the Alternate Allele allowing, thus, for very low frequencies.

Further impose Phred Score of the called variant (Q) bigger or equal than 20 and passing all the filters; total read depth of the called variant (RD) bigger or equal than 10 and genotype quality of the called variant (GQ) bigger or equal than 20.

Gene Expression Analysis by WTS

To determine mRNA abundance, we used the bioinformatic program Genesifter (Geospiza) which used BWA and mapped read normalization. Mapped normalization takes the raw count for the number of exons and splices mapped reads per gene and divides it by the total number of mapped reads. In addition, all values represented were normalized to the expression of actin (ActB).

Identifying Copy Number Variations

XHMM (eXome-Hidden Markov Model) version 1.0 was used with default parameters, as per the software's manual, for all samples simultaneously. This involved using GATK to calculate depth of coverage and GC content, and PLINK/SEQ to get the fraction of repeat-masked bases. From GATK's depth of coverage output, we calculated the average autosomal coverage of all samples, shown in Table 1:

TABLE 1

| SAMPLE | average autosomal coverage |
|---|---|
| CS | 29.84 |
| p_Ib1 | 72.35 |
| p_Ib2 | 128.83 |
| p_Ib3 | 49.97 |
| r_IbBM | 65.48 |
| r_IbSP | 100.48 |

Log R ratios of read depth were calculated as follows for the normal sample:

$$\log_2(\text{mean RD within target}_{normal}/\text{mean RD overall}_{normal})$$

And as follows for all tumor samples:

$$\log_2((\text{mean RD within target}_{tumor}/\text{mean RD overall}_{tumor})/(\text{mean RD within target}_{tumor}/\text{mean RD overall}_{tumor}))$$

Alternate allele frequencies were calculated from genotype calls of exome data, after filtering out loci with fewer than 10 reads. The final list of CNVs consisted of those consistent across XHMM calls, read depth ratios, and allele frequencies. Downstream analysis of these CNVs, such as identifying genes in the regions, was performed with PLINK software.

Relapse-Specific C481S BTK Mutation in MCL

To elucidate the mechanism of resistance to targeting BTK with Ibrutinib, we investigated the dynamic tumor evolution and discerned mutations that were expressed in MCL tumors by integrative WES and WTS analysis of 5 serial biopsies in the course of two years of a representative MCL patient (Pt 7). This patient had four prior therapies before the Ibrutinib regimen (560 mg daily), and achieved a partial response for 14 months before progression with mild lymphadenopathy and massive splenomegaly.

Single nucleotide variant (SNV) analysis of serial WES and Sanger sequencing detected a non-synonymous substitution of C for G at nucleotide 1442 (G1442C) and a synonymous C1443T substitution in the same codon of BTK at relapse in MCL cells in both the bone marrow (r_IbBM, 74% of the reads) and the spleen (r_IbSP, 83% of the reads). This resulted in a conservative change of cysteine to serine in amino acid residue 481 (C481 S) localized in the tyrosine kinase domain of BTK (FIGS. 1A-B, 5-6). Importantly, the C481S mutation was not detected in any of the 3 serial lymph node biopsies taken 8-7 months (p_Ib1 and p_Ib2) or immediately (p_Ib3) before the start of the ibrutinib therapy, or in the cheek swab (CS) (FIGS. 1A-B and 5-6). The C481S BTK mutation is unlikely to be a rare occurrence because it was the same as 4 out of 5 SNVs detected in CLL patients relapsed from ibrutinib. The presence of two identical nucleotide substitutions in the same codon of BTK in bone marrow and splenic MCL cells is highly uncommon, further implicating a clonal origin for the resistant MCL cells.

Figure 1C:
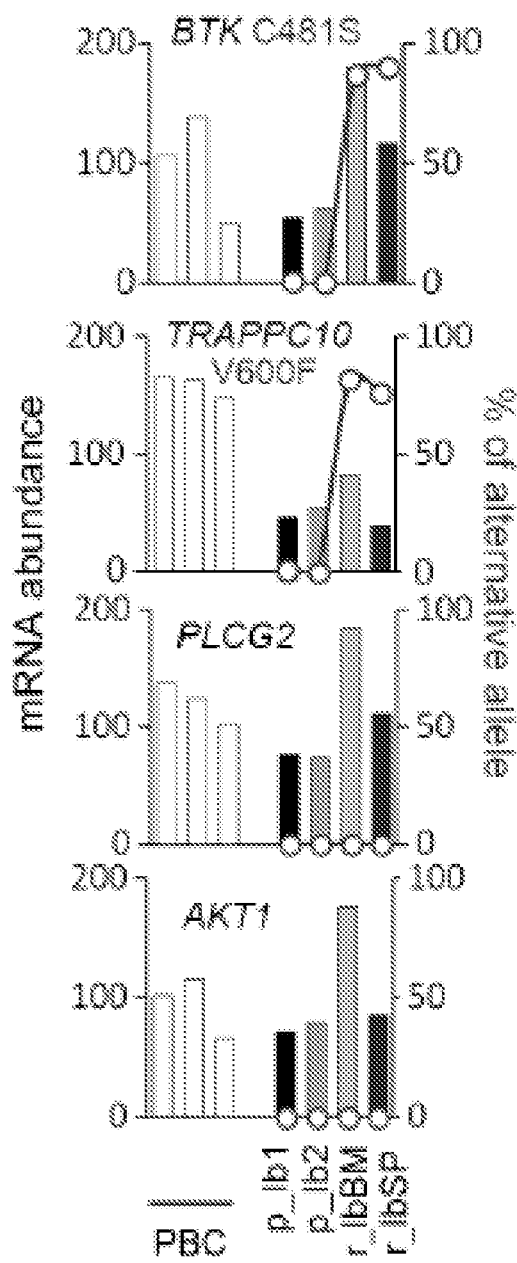
Figure 5:
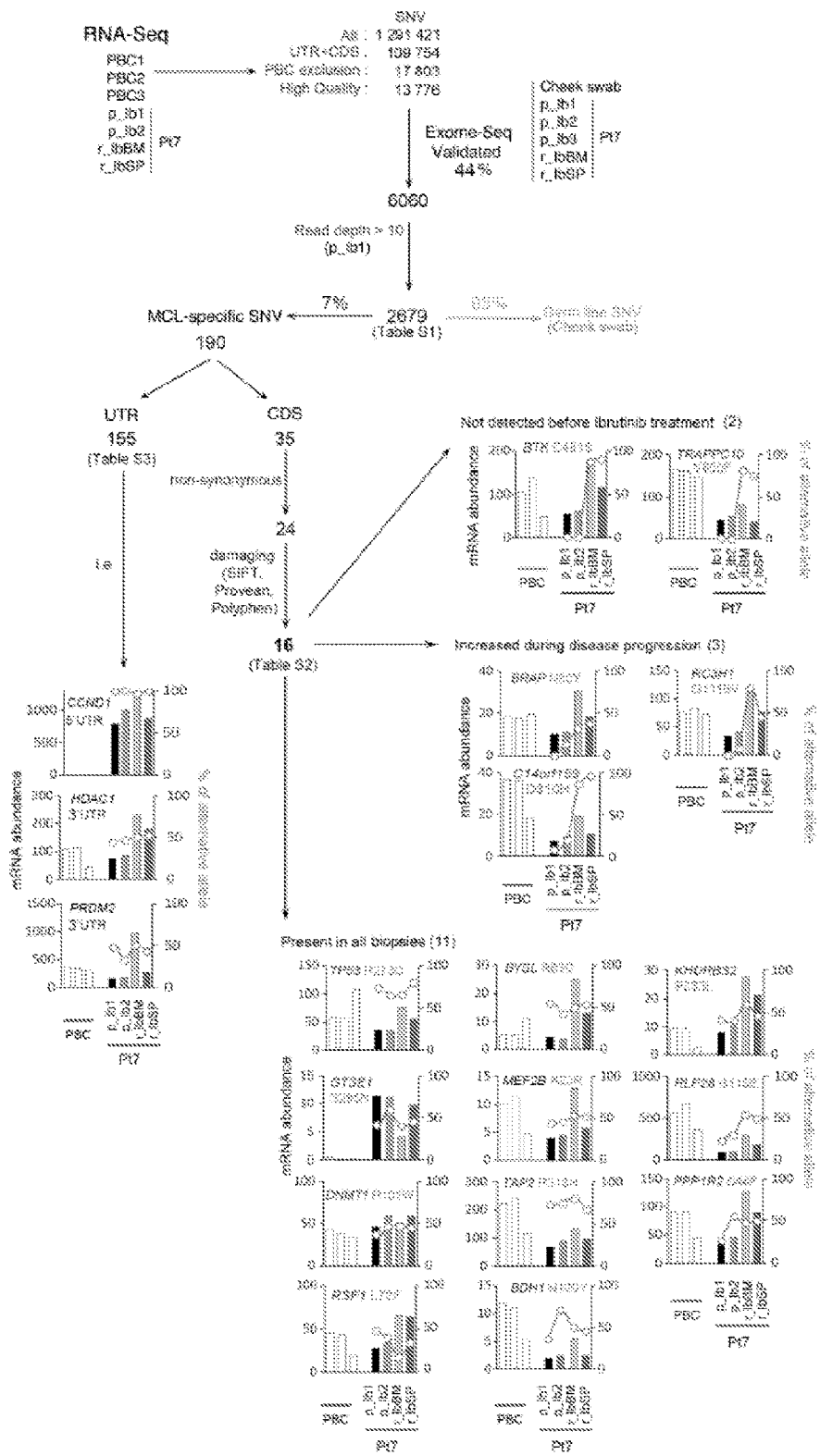
FIG. 5 exemplifies single nucleotide variants (SNV; 1, 291, 421) identified in MCL cells from serial biopsies of Pt7 before Ibrutinib treatment (p_Ib1, p_Ib2) and after relapse from Ibrutinib (r_IbBM, r_IbSP) by RNA-sequencing using the Illumina platform and Genesifter (Geospiza®), which uses the Genome Analysis Toolkit (GATK) for base quality score recalibration and local realignment for indels. SNVs detected in PBC libraries are removed, resulting in 13,776 confident SNVs. Among these, 44% (n=6060) are also detected by WES analysis. A threshold of 10× coverage is applied, which reduces the number of mutations to 2679. The germline SNVs present in the cheek swab (CS) are then excluded to deduce 190 mutations that are specific to the MCL cells of this patient: 155 significant SNVs present in untranslated regions (UTRs) and 35 non-synonymous SNVs present in the coding regions (CDSs). Among them 16 are predicted to be damaging by SIFT, PROVEAN or PolyPhen-2, 5 being detected at varying frequencies in serial biopsies.

Longitudinal integrative WES and WTS analysis revealed 190 MCL-specific SNVs that were not presented in the germline (FIG. 5): 35 non-synonymous SNVs in the coding sequences (CDS) of which 16 were predicted to be damaging at the protein level and 155 SNVs in the untranslated regions (UTR). Five of the non-synonymous mutations were present in BRAP, RG3H1, C14orf159, BTK and TRAPPC10 at increasing frequencies in disease progression, but only C481S in BTK and V600F in TRAPPC10 were not detected before ibrutinib treatment (FIG. 5). The high frequency of C481S mutation at relapse determined by WES was confirmed by WTS in 87% of the reads in the bone marrow MCL cells (depth=129) and 90% in the spleen MCL cells (depth=372) (FIG. 1C), as was the high frequency of V600F mutation (FIG. 5). TRAPPC10 (Trs130) is a component of the TRAPPII (transport protein particle II) complex with no known function in BCR signaling or oncogenic transformation. The significance of V600F TRAPPC10 mutation in MCL progression is thus unclear. Nonetheless, its unique association with the C481S BTK mutation at relapse in both bone marrow and splenic MCL cells supports a clonal origin for ibrutinib resistant MCL cells. No mutations in other genes of the BCR or PI3K signaling pathway were identified, including the activating R665W mutation in PLCγ2 downstream of BTK that was detected in ibrutinib resistance in CLL (FIGS. 1C and 5), further highlighting the remarkable specificity of C481S BTK mutation in ibrutinib resistance in MCL.

Figure 1D:
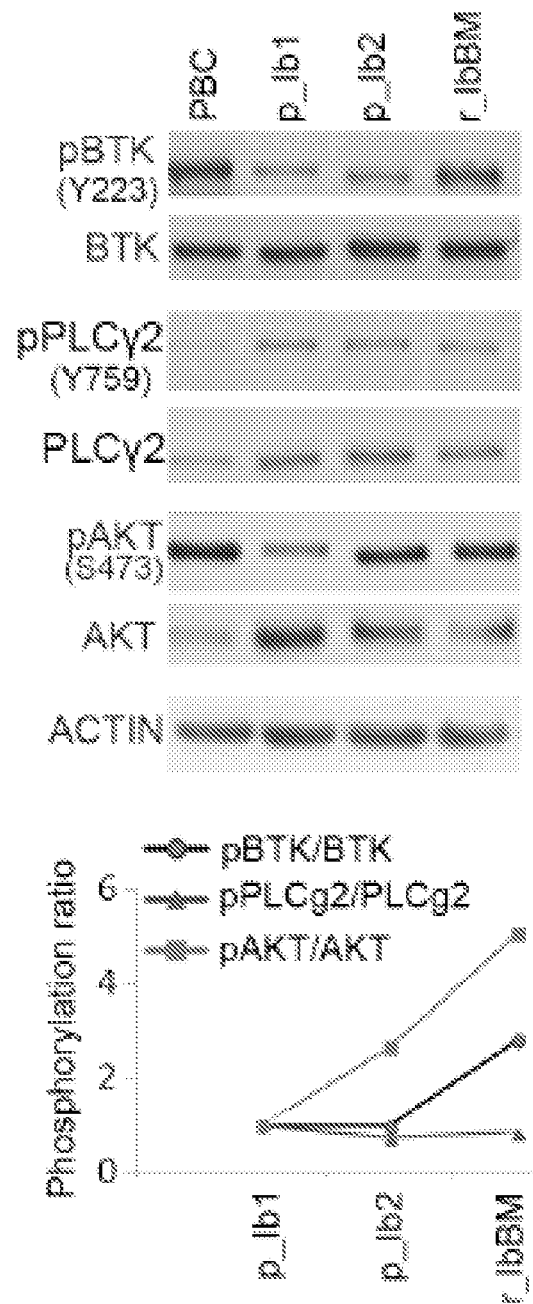

BTK Activation and Induction of Chemokines and the CXCR4-CXCL12 Autocrine Loop at Relapse Ibrutinib inhibits the BTK activity irreversibly by covalent binding to cysteine 481 in vivo and in vitro. The C481S mutation in BTK markedly reduced the affinity for ibrutinib (~25-fold) and conferred resistance to ibrutinib in a model chicken lymphoma DL40 cell line. We found that activation of BTK (Y223) was constitutive in MCL cells before ibrutinib therapy as expected for the survival of MCL cells, and in PBCs in tonic BCR signaling for their maintenance (FIG. 1D). Consistent with relief from ibrutinib inhibition, pBTK (Y223) was enhanced at relapse in MCL cells in the bone marrow, where nearly 90% of the MCL cells harbored the C481S mutation (FIG. 1D). Activation of ATK (S473) by mTORC2 also increased in disease progression even before relapse as shown by the ratio of pATK/AKT, whereas PLCγ2 activation did not vary (Y759) (FIG. 1D). These data suggest that the C481S mutation relieves BTK from ibrutinib inhibition in vivo, leading to heightened activation of BTK and ATK to promote the survival and proliferation of resistant MCL cells.

Figure 1E:
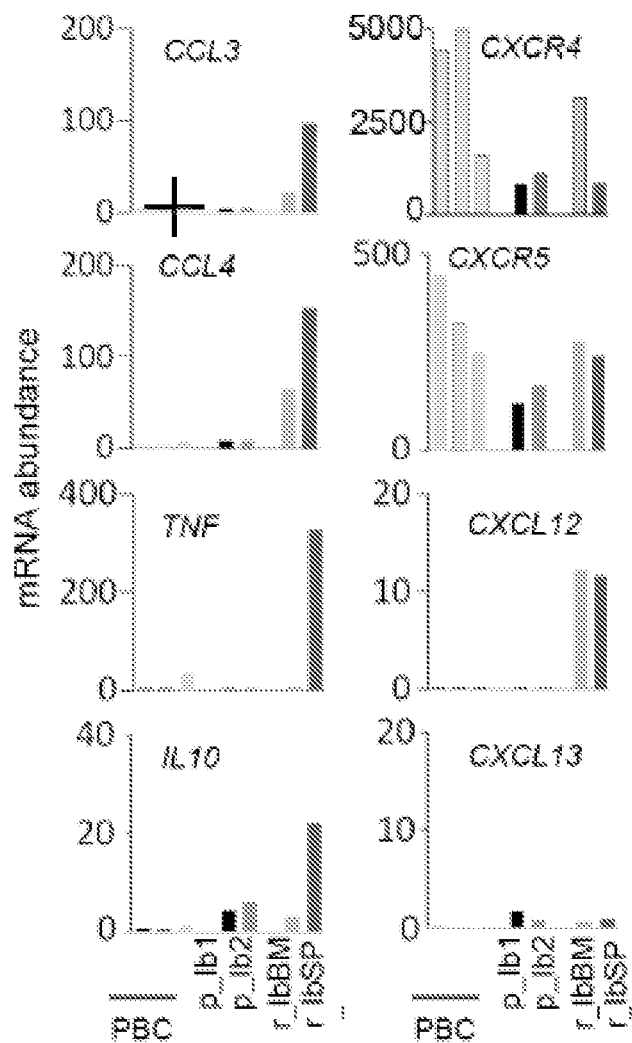

Ibrutinib has also been shown to suppress the expression of CCL3, CCL4, TNF and IL10 that promote proliferation and survival of MCL cells ex vivo. Providing a functional evidence for ibrutinib resistance in humans, the expression of CCL3, CCL4, TNF and IL10 was coordinately and prominently elevated at relapse, primarily in MCL cells in the spleen (FIG. 1E). CXCR4, but not CXCR5, mRNA was also markedly increased in the bone marrow MCL cells at relapse, concomitant with induction of CXCL12, but not CXCL13, in MCL cells in both the bone marrow and the spleen (FIG. 1E). Since CXCL12-CXCR4 signaling is known to activate BTK via PI3K signaling, induction of the CXCR4-CXCL12 autocrine loop may fuel BTK activation (FIG. 1D) unopposed by ibrutinib in resistant MCL cells, especially in the bone marrow.

Exacerbated genomic instability and tissue-specific proliferation of MCL cells at relapse.

Figure 2A:
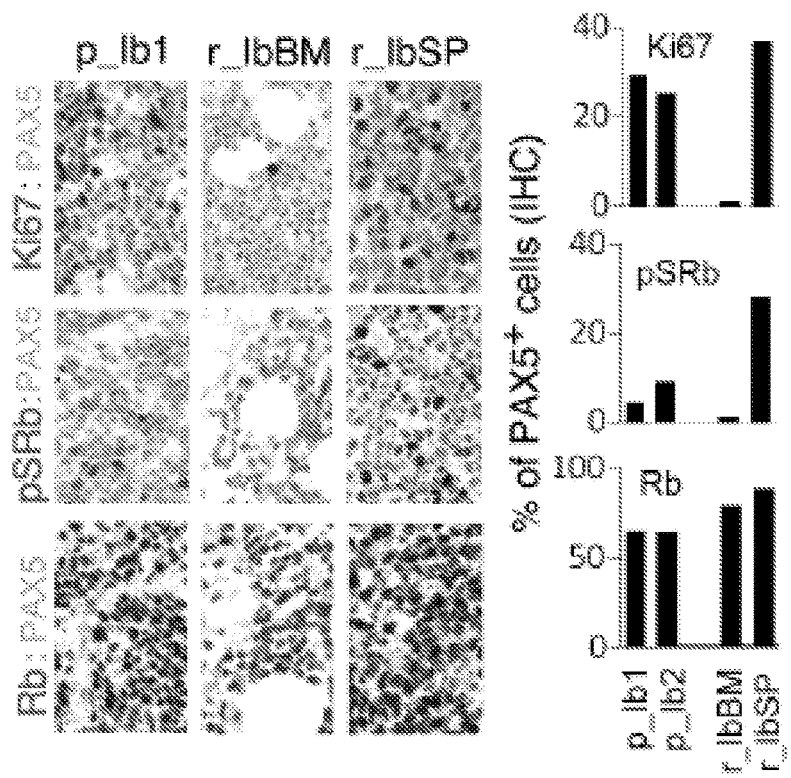
FIG. 2A-FIG. 2E exemplify characteristics of MCL cells at ibrutinib relapse.
Figure 2B:
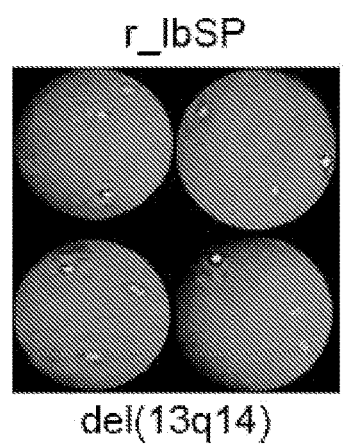

Unrestrained tumor cell proliferation is characteristic of relapse from ibrutinib in both MCL and CLL. Progression of the MCL patient under study was associated with massive splenomegaly and mild lymphadenopathy, indicating a tissue-specificity. To investigate the underpinning mechanism(s), we first evaluated the proliferation of MCL cells in situ in serial biopsies by immunohistochemistry (IHC) (FIG. 2A). More MCL cells (Pax 5+) were cycling (Ki67+) in the spleen at relapse than in the lymph nodes before ibrutinib therapy (p_Ib1), apparently due to accelerated cell cycle progression through early G1 given the >3-fold increase in CDK4/CDK6-specific phosphorylation of Rb (pSRb)(FIG. 2A). Despite the common C481S BTK mutation at relapse, however, bone marrow MCL cells rarely cycled or expressed pSRb (active CDK4) (FIG. 2A). Thus, MCL cells preferentially proliferate in the spleen and not in the bone marrow micro-environment at relapse, which may be facilitated by the selective increases in CCL3, CCL4, TNF and IL10 in splenic MCL cells in concert with CXCR4-CXCL12 autocrine signaling (FIG. 1E).

Figure 2C:
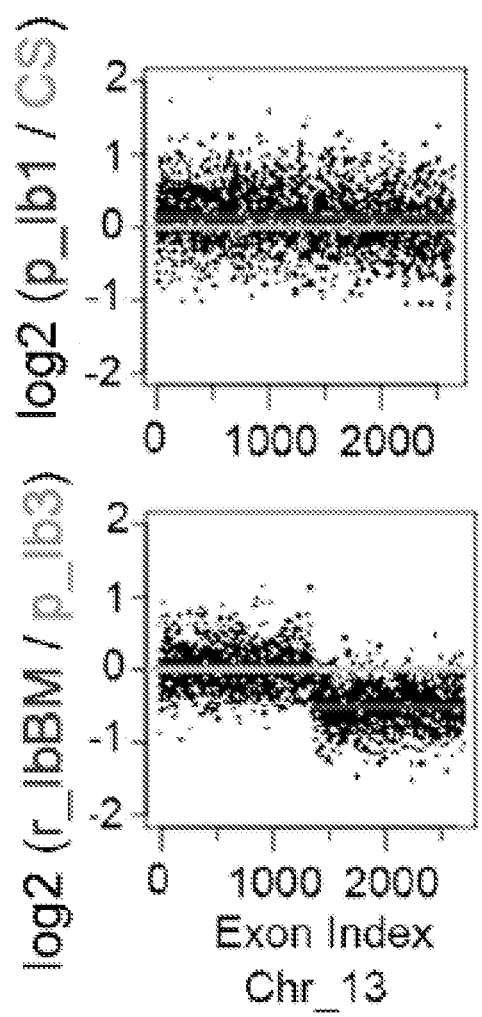
Figure 2D:
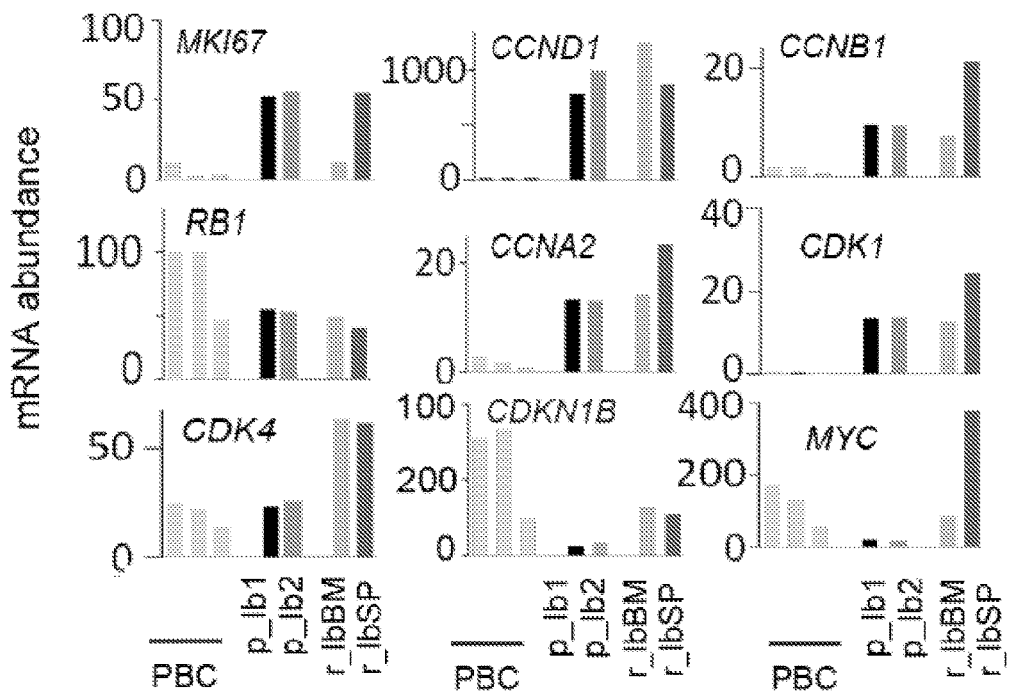
Figure 7A:
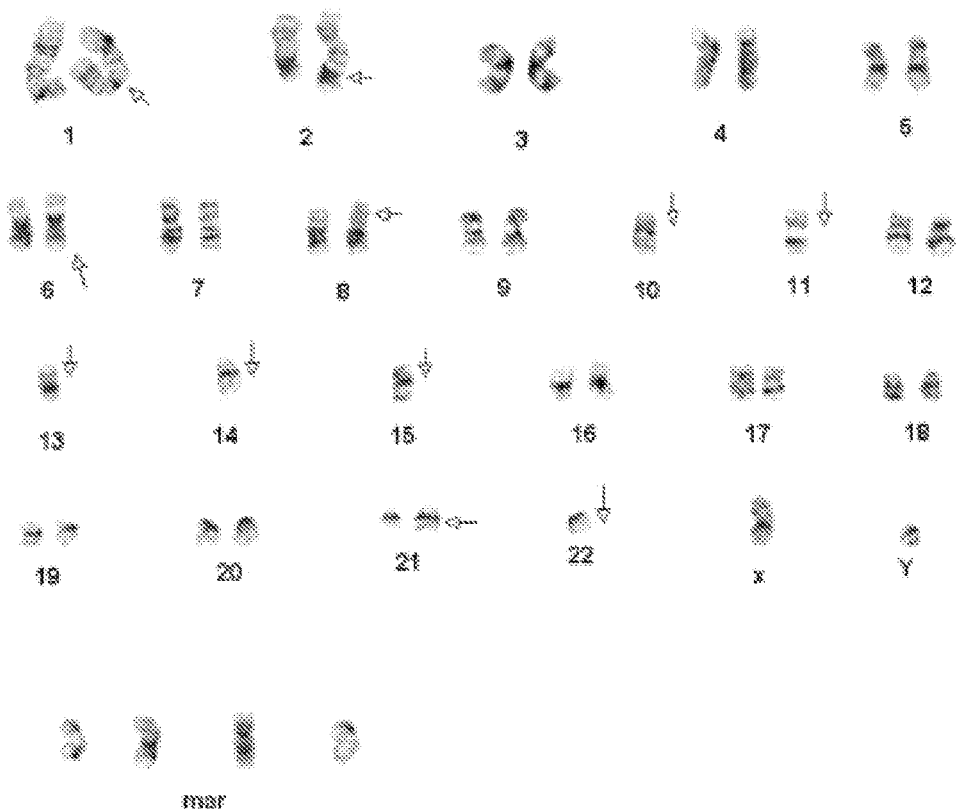
FIG. 7A-FIG. 7B exemplify karyotype and t(11; 14) FISH results in spleen MCL tissues at ibrutinib relapse.
Figure 7B:
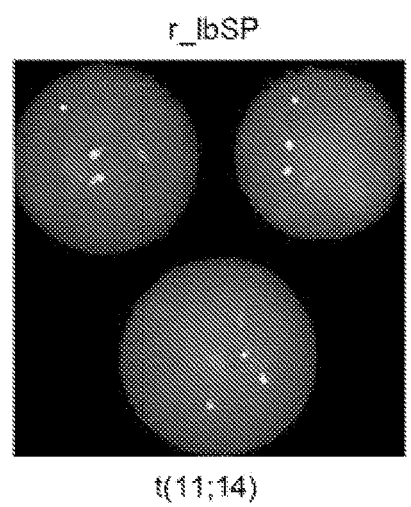
Figure 9:
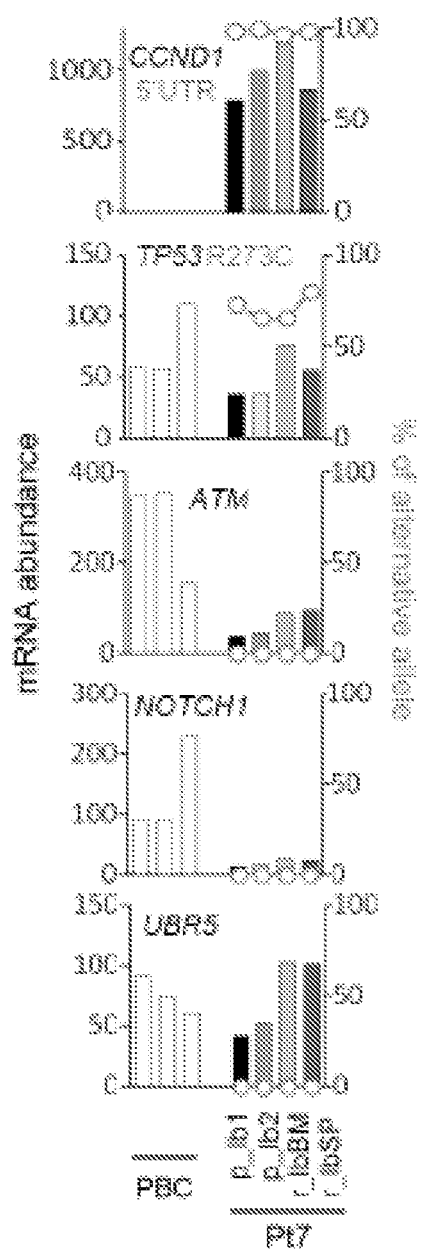
FIG. 9 exemplifies WTS analysis of mRNA abundance (bars) and SNVs (% of alternative allele, red line) in the coding and untranslated regions of genes commonly mutated in MCL (TP53 (p53), ATM, CCND1, NOTCH1, UBR5).

Cytogenetics analysis further revealed a complex karyotype in proliferating MCL cells in the spleen at relapse. Multiple numerical and structural abnormalities were observed, most notably the hemizygous deletion of chromosome 13q that encompasses the Rb gene (FIG. 7A). This was confirmed by FISH using a probe spanning the Rb locus on 13q14 (FIG. 7B), along with validation of the t(11:14) chromosomal translocation characteristic of MCL cells, also by FISH (FIG. 7B). Copy number variation (CNV) analysis of serial WES of purified MCL cells independently demonstrated the hemizygous deletion of 13q at relapse in the bone marrow MCL cells, and discovered two additional relapse-specific hemizygous deletions in 21q, which included the TRAPPC10 gene located at 21q22.3 (FIGS. 2C and 9). However, Rb expression was unabated at the mRNA (FIG. 2D) and protein levels (FIG. 2A) in MCL cells at relapse in both the bone marrow and the spleen, presumably by a compensatory mechanism. Relapse from Ibrutinib is thus associated with exacerbated genomic instability of MCL cells in the presence of sustained Rb expression.

Figure 2E:
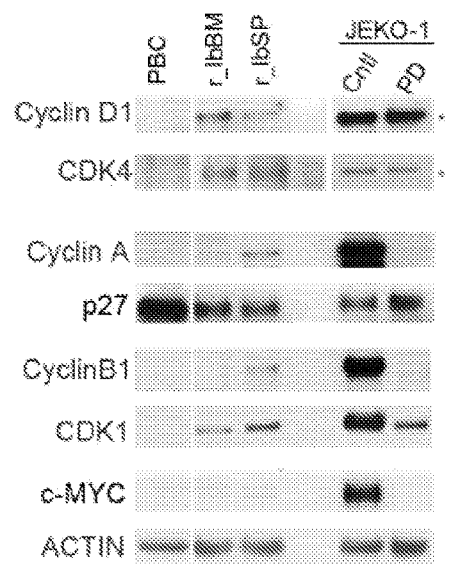

Further investigation of the tissue-specificity showed an increase in CDK4 mRNA and sustained expression of abundant Cyclin D1 mRNA at relapse. Cyclin A, Cyclin B1 and CDK1 mRNAs were expressed in MCL cells but not in PBCs, and selectively increased in resistant MCL cells in the spleen (FIG. 2D) in parallel with protein expression (FIG. 2E). Despite a striking increase in c-Myc mRNA in the splenic MCL cells, the c-Myc protein was undetectable, ruling out its role in the proliferation of resistant MCL cells. Together with the spleen-specific CDK4 phosphorylation of Rb (FIG. 2A), differential proliferation of resistant MCL cells in the spleen appears to be driven by upregulation of CDK4 in conjunction with differential expression of Cyclin A, Cyclin B and CDK1.

Prolonged Early G1 Arrest Sensitizes MCL Cells to Ibrutinib Via Synergic Induction of PIK3IP1

Selective targeting of CDK4 with PD 0332991 resulted in prolonged early G1 arrest (pG1) and a durable clinical response in recurrent MCL patients. Induction of pG1 by sustained CDK4/CDK6 inhibition was further shown to reprogram primary myeloma for bortezomib killing and primary MCL cells for PI3K inhibitor killing ex vivo. The increase in CDK4 and the maintenance of Rb expression in ibrutinib resistance suggests that timely inhibition of CDK4 may delay or prevent the emergence or expansion of resistant MCL cells through both cell cycle control and pG1 reprogramming that lowers the threshold of ibrutinib killing.

Figure 3A:
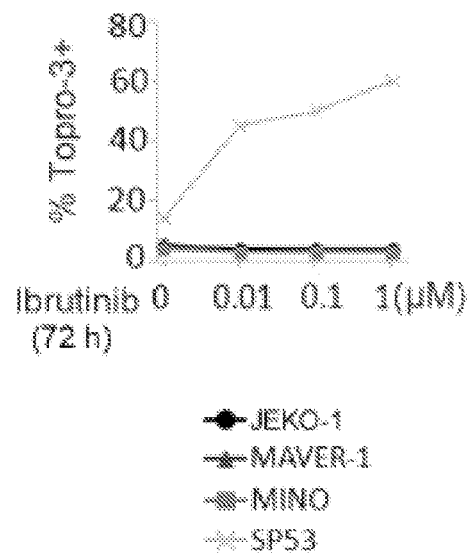
FIG. 3A-FIG. 3F exemplifies the effects of selective inhibition of CDK4 on MCL cells.
Figure 3B:
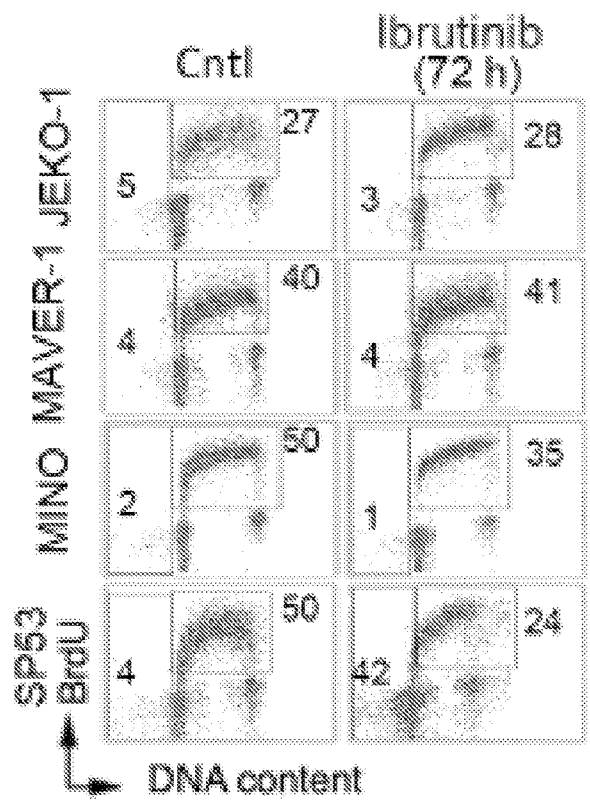
Figure 3C:
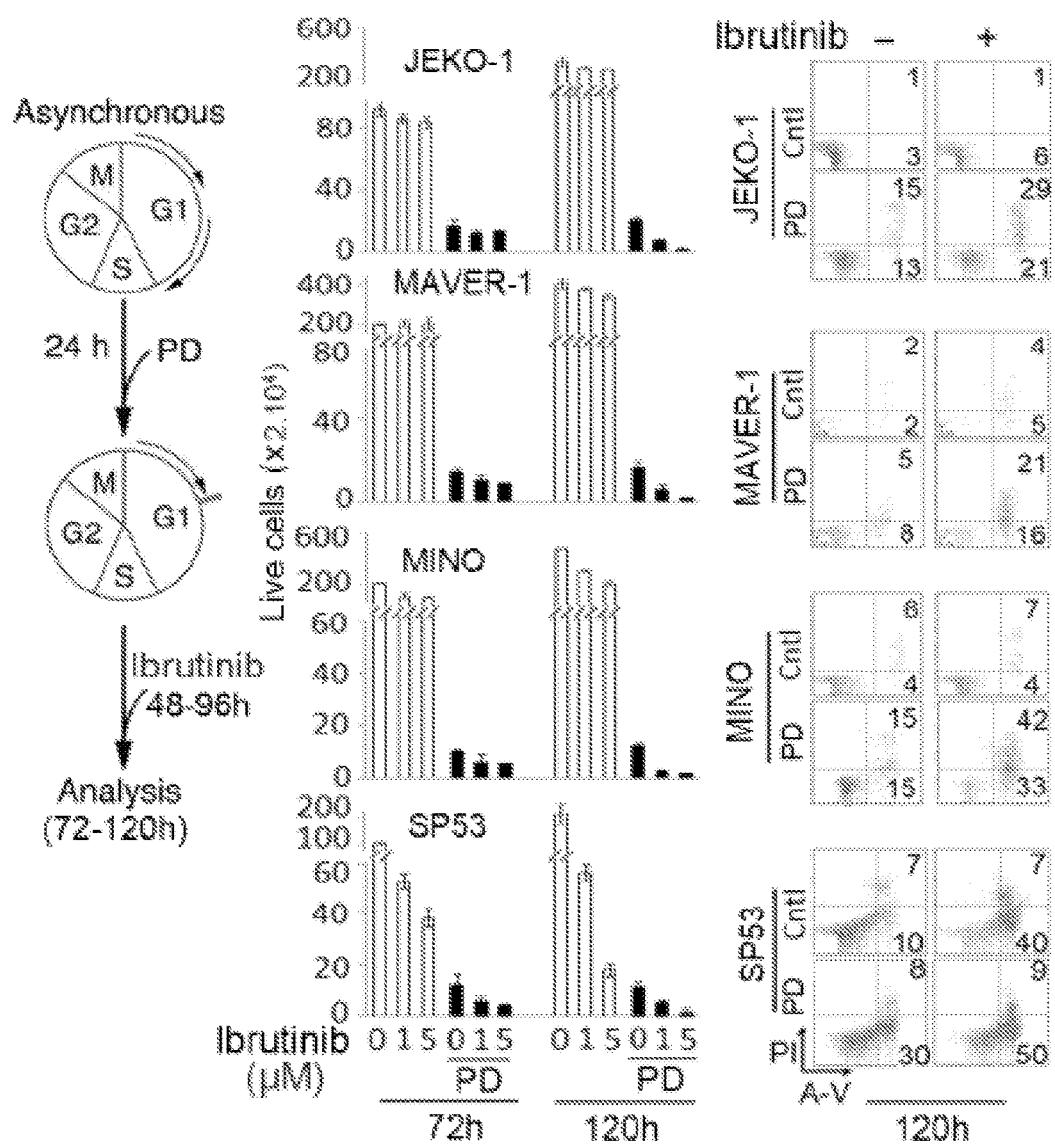

This hypothesis was tested in four Rb+MCL cell lines with graded ibrutinib sensitivity. First it was confirmed in JEKO-1 cells that inhibition of CDK4 by PD 0332991 led to pG1, which maintained the expression of cell cycle genes scheduled for early G1 (Cyclin D1 and CDK4), elevated the CDK inhibitor p27 protein through reduction of Skp-2 required for p27 degradation, and prevented the expression of cell cycle genes programmed for late G1 (Cyclin A) and G2/M (Cyclin B and CDK1) (FIG. 2E and data not shown). JEKO-1 and MAVER-1 cells were completely refractory to ibrutinib (FIG. 3A) even though they harbor no mutations in BTK or PLCγ2 (data not shown). Ibrutinib was not toxic to MINO cells while moderately inhibiting S phase entry based on BrdU pulsing/PI analysis, but potently induced apoptosis of SP53 cells, apparently at the G1-S transition as shown by the accumulation of sub 2N cells and reduction of S phase cells (FIG. 3A-B). Induction of pG1 by PD 0332991 not only prevented JEKO-1, MAVER-1 and MINO cells from replicating but also reprogrammed them for apoptosis (AnnexinV+/PI+) in response to Ibrutinib, leading to a striking 50-100 fold reduction of live cells compared with cells treated with ibrutinib alone by 96 hours (FIG. 3C). Although pG1 did not augment ibrutinib killing further in the highly sensitive SP53 cells, it significant reduced the number of live cells through cell cycle control (FIGS. 3A and C).

Figure 3D:
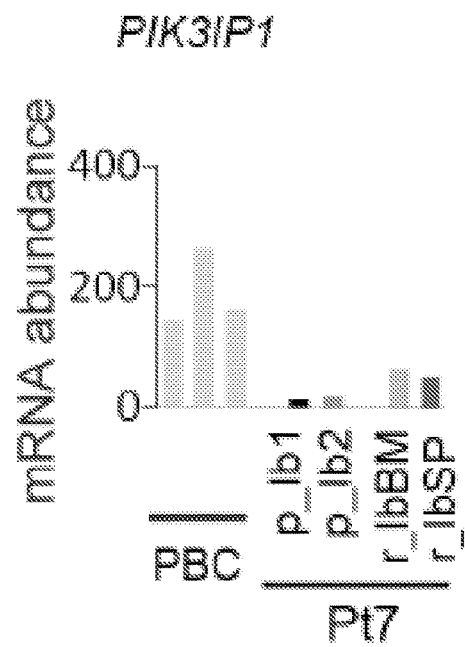
Figure 3E:
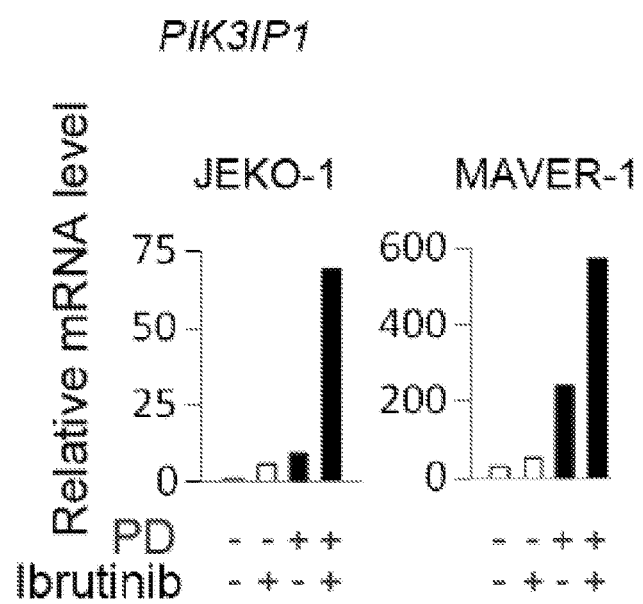
Figure 3F:
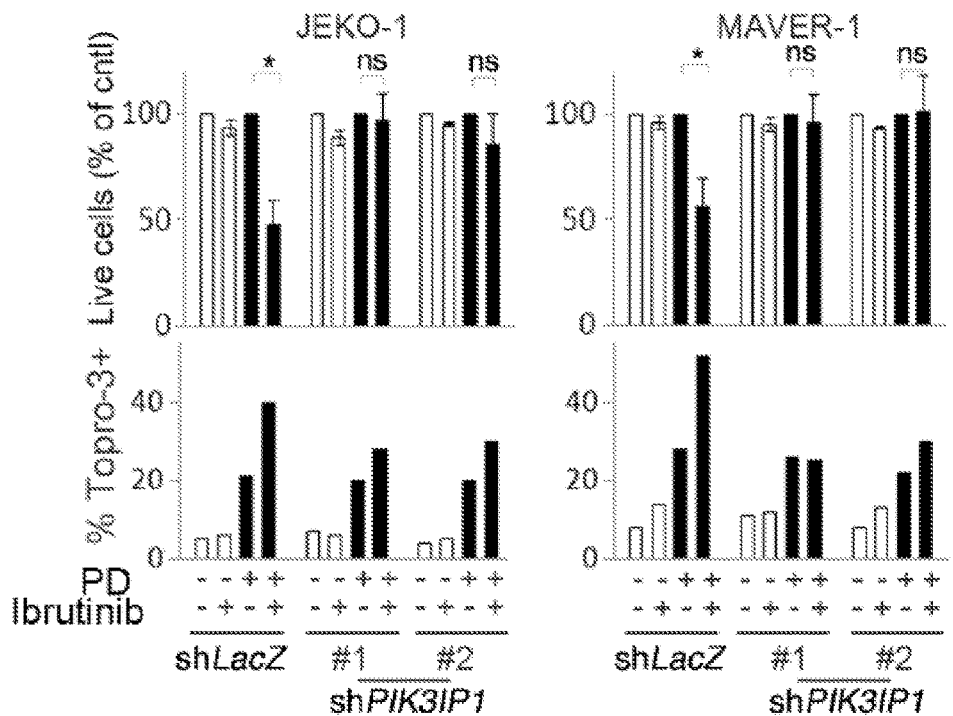

To investigate the mechanism for pG1 sensitization to ibrutinib killing, we turned to PIK3IP1, a negative regulator of PI3K that was suppressed in primary MCL cells and markedly induced in pG1 to enhance the killing by PI3K inhibitors. The abundance of PIK3IP1 mRNA in MCL cells in all serial biopsies was 10-30 folder lower compared with PBCs (FIG. 3D). It was modestly induced by ibrutinib and in pG1 alone, but dramatically induced (3050 fold) by ibrutinib in pG1 reprogrammed JEKO-1 and MAVER-1 cells (FIG. 3E). Knocking down PIK3IP1 by two independent shRNA-lentivirus constructs significantly blunted the enhancement of ibrutinib killing in pG1, but not the death induced in pG1 in JEKO-1 or MAVER-1 cells (FIG. 3F). Induction of prolonged early G1 arrest by selective inhibition of CDK4 with PD 0332991 therefore not only prevents refractory MCL cells from proliferating, but also reprograms them for ibrutinib killing through induction of PIK3IP1.

Figure 4A:
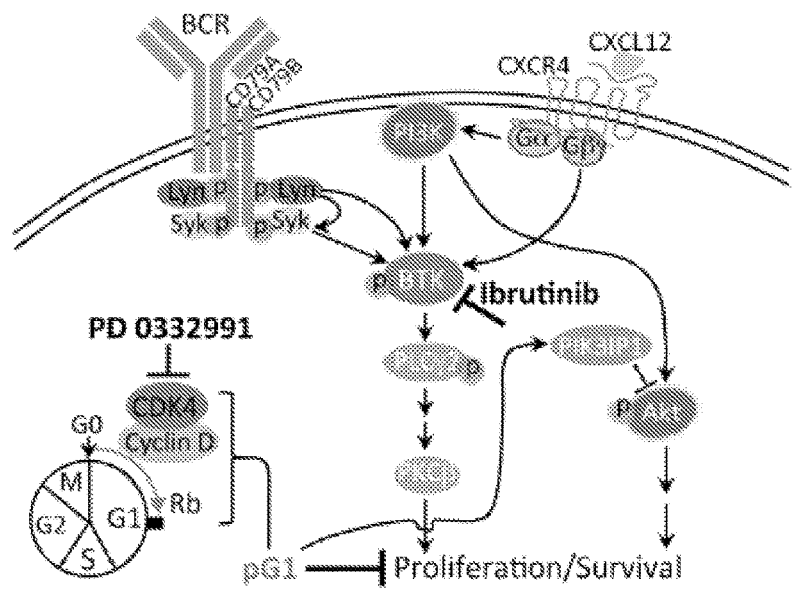
FIG. 4A-FIG. 4B exemplify cell signaling pathways.
Figure 4B:
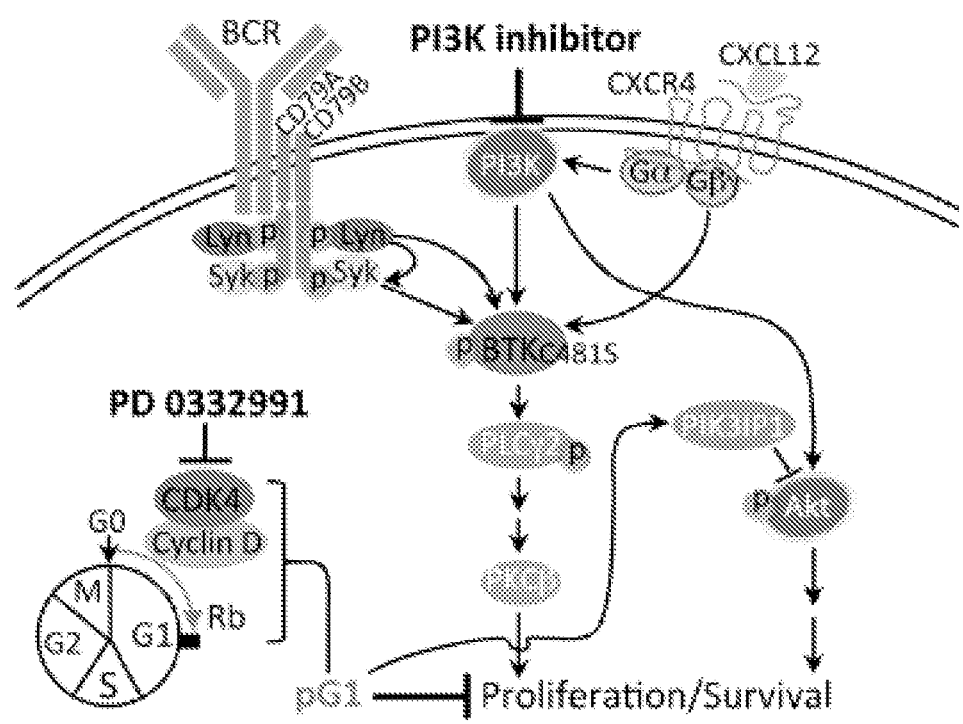

A schema for dual targeting of BTK with ibrutinib and CDK4 inhibitor with PD 0332991 in MCL cells is shown in FIG. 4A. In FIG. 4A, the schema illustrates MCL cells expressing wild-type BTK. The prolonged early $G_1$ arrest exceeded the scheduled early $G_1$ transit time (16-20 hours in MCL cells) by selective and sustained inhibition of CDK4. FIG. 4B shows the schema for overriding the C481S mutation in BTK by dual inhibition of CDK4 and PI3K.

FIG. 5 shows longitudinal integrative WES and WTS analysis of acquired resistance following a durable response in MCL harboring $BTK^{C481S}$. SNVs (1,291,421) were identified in MCL cells from serial biopsies of Patient (Pt) 1 before ibrutinib treatment (p_Ib1, p_Ib2) and after relapse from ibrutinib (r_IbBM, r_IbSP) by WTS using the Illumina platform and Genesifter (Geospiza). After exclusion of SNVs detected in PBC libraries, 44% (n=6,060) of the 13,776 SNVs were also detected by WES analysis. A threshold of 10x coverage was applied, which reduced the number of SNVs to 2,679. After exclusion of the germline SNVs present in the cheek swabs, 190 SNVs were specific to the MCL cells of this patient: 155 detected in UTRs and 35 in CDS, of which 16 were predicted to be damaging at the protein level by SIFT, PROVEAN, or PolyPhen-2. Among them, 5 were detected at increasing frequency in serial biopsies but only $BTK^{C481S}$ and $TRAPPC^{V600F}$ mutations were detected at relapse exclusively, and 11 were present in all biopsies.

Figure 6:
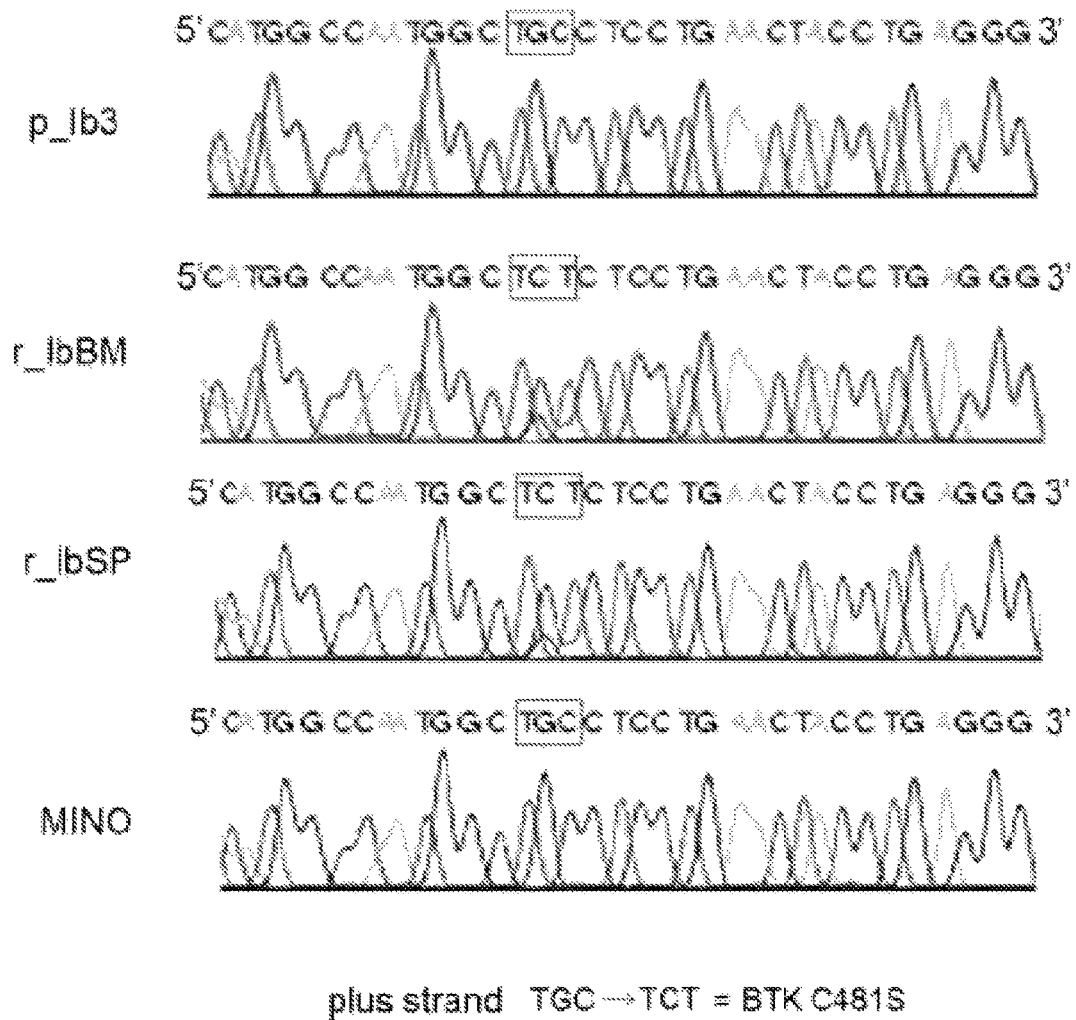
FIG. 6 exemplifies Sanger sequencing to detect identical dinucleotide substitutions (G1442C and C1443T), resulting in the C481S conservative mutation in BTK in the bone marrow and spleen biopsies after relapse (r_IbBM, r_IbSP), and the wild type sequences in the biopsy immediately before ibrutinib treatment (p_Ib3) and in the MCL MINO cell line.

FIG. 6 illustrates Sanger sequencing to detect identical dinucleotide substitutions (G1442C and C1443T), resulting in the C481S conservative mutation in BTK in the bone marrow and spleen biopsies after relapse (r_IbBM, r_IbSP), and the wild type sequences in the biopsy immediately before ibrutinib treatment (p_Ib3) and in the MCL MINO cell line.

FIG. 7 exemplifies karyotype and t(11; 14) FISH results in spleen MCL tissues at ibrutinib relapse. FIG. 7A exemplifies a complex karyotype with multiple numerical and structural abnormalities in nine of 10 evaluated metaphase cells from the spleen at relapse (r_IbSP). The clonal abnormalities include additional chromosomal material of unknown origin on 1q, 2q, 8p, and 21q, interstitial deletion of 6q, monosomy of chromosomes 2, 10, 11, 13, 14, 15, and 3-7 marker chromosomes. FIG. 7B exemplifies a representative image of a fluorescence in situ hybridization assay using spectrum labeled LSI CCND1 probe and spectrum labeled LSI IGH probe. The two fusion signals exemplify the presence of a reciprocal t(11; 14) translocation. The signals exemplify the normal CCND1 and IGH alleles respectively.

Figure 8A:
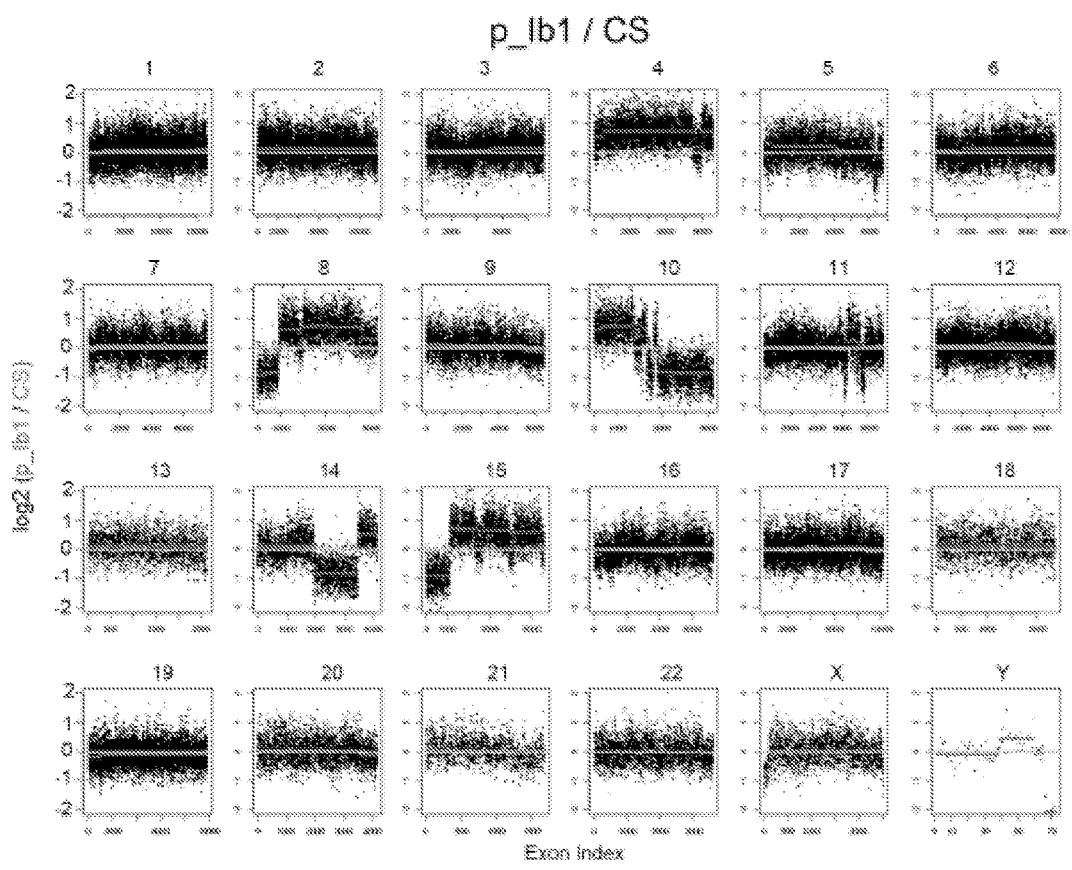
FIG. 8A-FIG. 8C exemplify biopsy analyses of spleen MCL tissues at ibrutinib relapse.
Figure 8B:
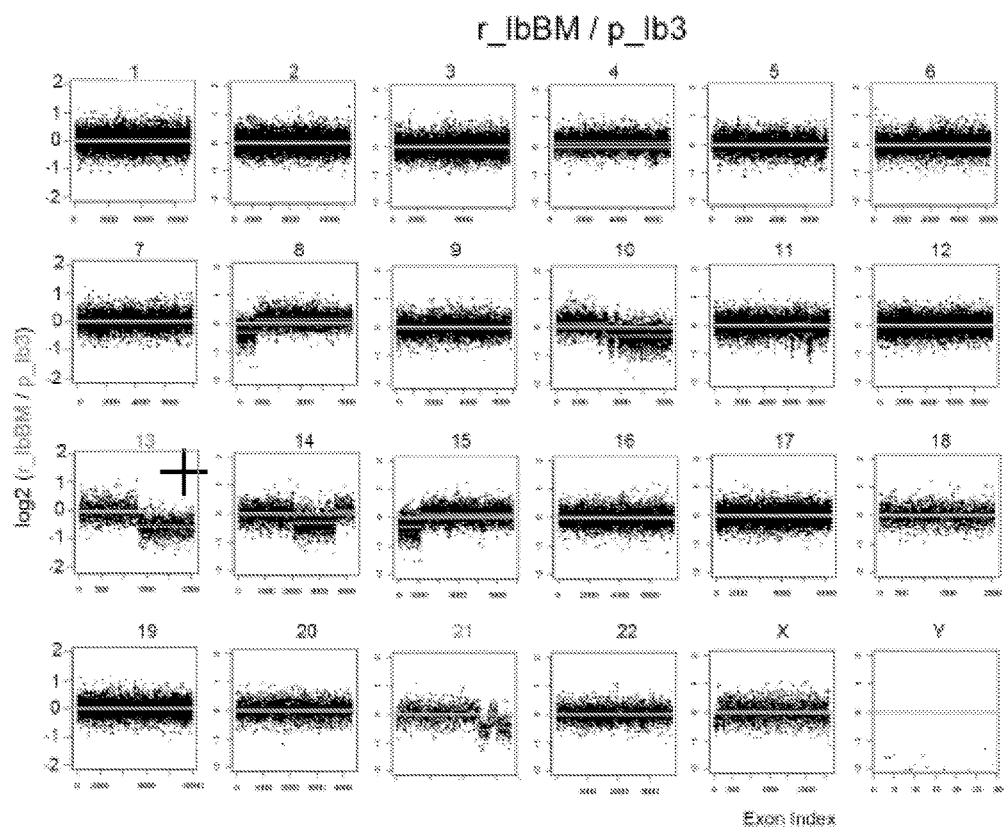
Figure 8C:
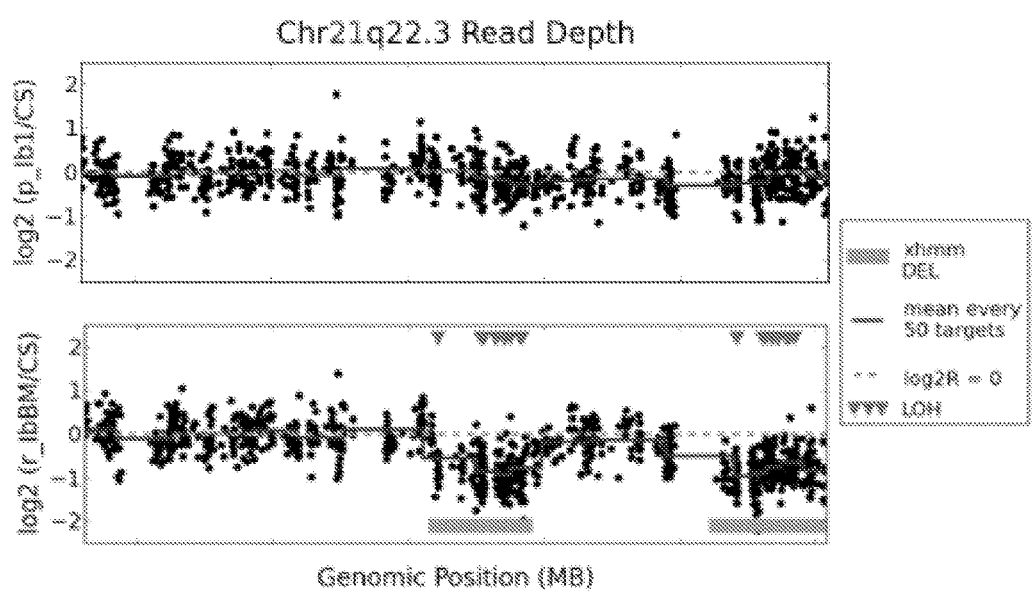

FIG. 8 exemplifies biopsy analyses of spleen MCL tissues at ibrutinib relapse. FIG. 8A exemplifies a Copy Number Variation (CNV) of WES data before Ibrutinib treatment (p_Ib1). FIG. 8B exemplifies a Copy Number Variation (CNV) of WES data after ibrutinib relapse (r_IbBM). FIG. 8C exemplifies a Copy Number Variation (CNV) of WES data after Ibrutinib relapse (r_IbBM) of Chr21q22.3.

FIG. 9 exemplifies WTS analysis of mRNA abundance (bars) and SNVs (% of alternative allele, red line) in the coding and untranslated regions of genes commonly mutated in MCL (TP53 (p53), ATM, CCND1, NOTCH1, UBR5).

Example 2: Safety and Tolerability Study of Co-Administration of Ibrutinib and PD 0332991 in Mantle Cell Lymphoma (MCL)

Purpose: The primary objective of this trial is to evaluate the safety of Ibrutinib in combination with PD 0332991 in relapsed/refractory subjects with Mantle Cell Lymphoma (MCL).

Primary Outcome Measures:

The maximum tolerated dose (MTD) of PD 0332991 in combination with Ibrutinib is determined in patients with recurrent MCL.

The MTD is determined by occurrence of Dose Limiting Toxicities during the first cycle:

Eligibility:

18 years and older; both genders are eligible.

Inclusion Criteria:

Patients have histologically or cytologically confirmed mantle cell lymphoma as defined by the World Health Organization. All patients have either a demonstrated t(11; 14) by karyotype, fluorescent in-situ hybridization (FISH) or positive immunohistochemistry for cyclin D1.

Subjects have measurable disease, defined as at least one tumor mass of >1.5 cm in diameter.

Subjects have received at least one prior chemotherapy-containing regimen and at least one prior rituximab-containing regimen.

Subjects are ≥18 years of age with accessible disease, defined as at least one of the following:

Adenopathy accessible to core needle biopsy.

Bone marrow involvement.

Circulating lymphoma cells in the peripheral blood.

ECOG performance status≤2.

Patients have normal organ and marrow function as defined below within 14 days before enrollment: ANC≥750 cells/uL, platelets≥75,000 cells/uL, hemoglobin≥8.0 g/dL, total bilirubin≤1.5 times upper limit of normal, AST (SGOT)/ALT(SGPT)≤3 times upper limit of normal, and calculated creatinine clearance≥30 mL/min.

Agreement to use contraception during the study and for 30 days after the last dose of study drug if sexually active and able to bear children.

Willing and able to participate in all required evaluations and procedures in this study protocol including swallowing capsules without difficulty.

Ability to understand the purpose and risks of the study and provide signed and dated informed consent and authorization to use protected health information (in accordance with national and local subject privacy regulations).

Exclusion Criteria:

Patients who have had chemotherapy, radiotherapy, antibodies, or investigational agents within 4 weeks prior to entering the study unless progression has been documented while on treatment, or those who have not recovered from adverse events due to agents administered more than 4 weeks earlier. Patients may be receiving prednisone at a maximum dose of 10 mg/day orally, provided the dose has been stable during the prior two weeks before starting treatment.

Patients may not be receiving any other investigational agents.

Prior exposure to PD 0332991.

Peripheral neuropathy≥grade 2 (CTCAEv3.0) within 14 days before enrollment.

History of allergic reactions attributed to compounds of similar chemical or biologic composition to Ibrutinib.

Contraindication to serial core needle biopsies.

Known HIV infection.

Known malabsorption syndrome that may affect absorption of the drug.

Known or suspected CNS involvement.

Uncontrolled illness including, but not limited to, ongoing or active infection, symptomatic congestive heart failure, unstable angina pectoris, cardiac arrhythmia, or psychiatric illness/social situations that would limit compliance with study requirements.

Pregnant and lactating women are excluded from the study because the risks to an unborn fetus or potential risks in nursing infants are unknown. Confirmation that the subject is not pregnant must be established by a negative serum B-human chorionic gonadotropin (B-hCG) pregnancy test result obtained during screening. Pregnancy testing is not required for post-menopausal or surgically sterilized women.

QTc>470 msec.

Current use or anticipated need for food or drugs that are known potent CYP3A4 inhibitors, including their administration within 7-days prior to the first PD 0332991 dose (i.e. grapefruit juice, verapamil, ketoconazole, miconazole, itraconazole, posaconazole, erythromycin, clarithromycin, telithromycin, indinavir, saquinavir, ritonavir, nelfinavir, lopinavir, nefazodone, diltiazem, atazanavir, amprenavir, and fosamprenavir).

Current use or anticipated need for drugs that are known potent CYP3A4 inducers, including their administration within 14-days prior to the first PD 0332991 dose (i.e. carbamazepine, dexamethasone, felbamate, omeprazole, phenobarbital, phenytoin, primidone, rifabutin, rifampin, and St. John's Wort).

Myocardial infarction within 6 months prior to enrollment or has New York Heart Association (NYHA) Class III or IV heart failure (see Appendix 7), uncontrolled angina, severe uncontrolled ventricular arrhythmias, or electrocardiographic evidence of acute ischemia or active conduction system abnormalities. Prior to study entry, any ECG abnormality at Screening has to be documented by the investigator as not medically relevant.

Diagnosed or treated for another malignancy within 3 years of enrollment, with the exception of complete resection of basal cell carcinoma or squamous cell carcinoma of the skin, an in situ malignancy, or low-risk prostate cancer after curative therapy.

What is claimed is:

1. A pharmaceutical combination comprising:
   (a) a therapeutically-effective amount of Ibrutinib;
   (b) a therapeutically-effective amount of palbociclib; and
   (c) a pharmaceutically-acceptable excipient.

2. A composition comprising:
   (a) a therapeutically-effective amount of Ibrutinib; and
   (b) a therapeutically-effective amount of palbociclib.

3. The composition of claim 2, wherein Ibrutinib and the palbociclib are in a unified dosage form or in separate dosage forms.

4. A method comprising administering to an individual a combination of (a) a therapeutically-effective amount of Ibrutinib, and (b) a therapeutically-effective amount of palbociclib for treating a B cell proliferative disorder in an individual in need thereof.

5. The method of claim 4, wherein the B cell proliferative disorder is characterized by a plurality of cells having a C481S mutation in a BTK polypeptide.

6. The method of claim 4, wherein the B cell proliferative disorder is characterized by a plurality of cells having an elevated level of CDK4 expression.

7. The method of claim 6, wherein the elevated level of CDK4 expression is an increased level of CDK4 expression.

8. The method of claim 6, wherein the increased level of CDK4 expression is an increased protein expression.

9. The method of claim 6, wherein the increased level of CDK4 expression is an increased gene expression.

10. The method of claim 4, wherein the B cell proliferative disorder is characterized by a plurality of cell having a t(11; 14)(q13; q32) chromosomal translocation.

11. The method of claim 4, wherein the B cell proliferative disorder is refractory to Ibrutinib or relapsed following treatment with Ibrutinib.

12. The method of claim 4, wherein the B cell proliferative disorder is a lymphoma.

13. The method of claim 4, wherein the B cell proliferative disorder is a non-Hodgkins lymphoma.

14. The method of claim 4, wherein the B cell proliferative disorder is mantle cell lymphoma, chronic lymphocytic leukemia (CLL), small lymphocytic lymphoma (SLL), diffuse large B-cell lymphoma (DLBCL), activated B-cell diffuse large B-cell lymphoma (ABC-DLBCL), germinal center diffuse large B-cell lymphoma (GCB DLBCL), double-hit (DH) DLBCL, primary mediastinal B-cell lymphoma (PMBL), Burkitt's lymphoma, follicular lymphoma, immunoblastic large cell lymphoma, precursor B-lymphoblastic lymphoma, precursor B-cell acute lymphoblastic leukemia, hairy cell leukemia B cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mediastinal (thymic) large B cell lymphoma, intravascular large B cell lymphoma, primary effusion lymphoma, or lymphomatoid granulomatosis.

15. The method of claim 4, wherein the B cell proliferative disorder is an ibrutinib-resistant B cell proliferative disorder.

16. The method of claim 4, wherein Ibrutinib and the palbociclib are administered concurrently, simultaneously or separately.

17. The method of claim 4, further comprising administering an additional therapeutic agent.

18. A method comprising administering to an individual a combination of (a) a therapeutically-effective amount of Ibrutinib, and (b) a therapeutically-effective amount of palbociclib for treating a mantle cell lymphoma in an individual in need thereof.

19. The method of claim 18, wherein the mantle cell lymphoma is an ibrutinib-resistant mantle cell lymphoma.

20. The method of claim 18, wherein the mantle cell lymphoma is an ibrutinib-resistant mantle cell lymphoma.

\* \* \* \* \*